(12) United States Patent
Murray et al.

(10) Patent No.: US 8,907,031 B2
(45) Date of Patent: Dec. 9, 2014

(54) IMINO CARBENE COMPOUNDS AND DERIVATIVES, AND CATALYST COMPOSITIONS MADE THEREFROM

(75) Inventors: Rex E. Murray, Peoria, IL (US); LeGrande Mancel Slaughter, Stillwater, OK (US); Dipesh Prema, Kamloops (CA); Jinhui Chen, Chandler, AZ (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 157 days.

(21) Appl. No.: 13/442,903

(22) Filed: Apr. 10, 2012

(65) Prior Publication Data

US 2012/0271018 A1    Oct. 25, 2012

Related U.S. Application Data

(60) Provisional application No. 61/477,281, filed on Apr. 20, 2011.

(51) Int. Cl.
  *C08F 4/76* (2006.01)
  *C08F 4/64* (2006.01)
(52) U.S. Cl.
  USPC .............................. 526/172; 526/161; 556/51
(58) Field of Classification Search
  USPC ............................. 556/51; 526/172, 161, 51
  See application file for complete search history.

(56) References Cited

U.S. PATENT DOCUMENTS

| | | | |
|---|---|---|---|
| 3,242,099 A | 3/1966 | Manyik | |
| 3,248,179 A | 4/1966 | Norwood | |
| 4,060,480 A | 11/1977 | Reed | |
| 4,452,910 A | 6/1984 | Hopkins | |
| 4,501,885 A | 2/1985 | Sherk | |
| 4,588,790 A | 5/1986 | Jenkins | |
| 4,794,096 A | 12/1988 | Ewen | |
| 4,808,561 A | 2/1989 | Welborn | |
| 5,352,749 A | 10/1994 | DeChellis | |
| 5,376,611 A | 12/1994 | Shveima | |
| 5,436,304 A | 7/1995 | Griffin | |
| 5,455,314 A | 10/1995 | Burns | |
| 5,565,175 A | 10/1996 | Hottovy | |
| 5,575,979 A | 11/1996 | Hanson | |
| 5,576,259 A | 11/1996 | Hasegawa | |
| 5,739,220 A | 4/1998 | Shamshoum et al. | |
| 5,807,938 A | 9/1998 | Kaneko | |
| 5,919,983 A | 7/1999 | Rosen | |
| 6,096,676 A | 8/2000 | Murray | |
| 6,103,657 A | 8/2000 | Murray | |

(Continued)

FOREIGN PATENT DOCUMENTS

| | | |
|---|---|---|
| WO | WO 00/01739 | 1/2000 |
| WO | WO 00/78826 | 12/2000 |

(Continued)

OTHER PUBLICATIONS

Bol et al. Organometallics, 1992, 11, 1981-1983.*

(Continued)

*Primary Examiner* — Rip A. Lee

(74) *Attorney, Agent, or Firm* — Merchant & Gould

(57) ABSTRACT

The present invention provides imino carbene compounds and their derivatives, catalyst compositions containing these compounds in combination with an activator, and polymerization processes using these catalyst compositions to polymerize one or more olefins.

20 Claims, 16 Drawing Sheets

(56) References Cited

U.S. PATENT DOCUMENTS

| | | | |
|---|---|---|---|
| 6,107,230 | A | 8/2000 | McDaniel |
| 6,165,929 | A | 12/2000 | McDaniel |
| 6,239,235 | B1 | 5/2001 | Hottovy |
| 6,262,191 | B1 | 7/2001 | Hottovy |
| 6,294,494 | B1 | 9/2001 | McDaniel |
| 6,300,271 | B1 | 10/2001 | McDaniel |
| 6,316,553 | B1 | 11/2001 | McDaniel |
| 6,355,594 | B1 | 3/2002 | McDaniel |
| 6,376,415 | B1 | 4/2002 | McDaniel |
| 6,388,017 | B1 | 5/2002 | McDaniel |
| 6,391,816 | B1 | 5/2002 | McDaniel |
| 6,395,666 | B1 | 5/2002 | McDaniel |
| 6,524,987 | B1 | 2/2003 | Collins |
| 6,548,441 | B1 | 4/2003 | McDaniel |
| 6,548,442 | B1 | 4/2003 | Collins |
| 6,576,583 | B1 | 6/2003 | McDaniel |
| 6,613,712 | B1 | 9/2003 | McDaniel |
| 6,613,851 | B1 | 9/2003 | Jens et al. |
| 6,632,894 | B1 | 10/2003 | McDaniel |
| 6,667,274 | B1 | 12/2003 | Hawley |
| 6,750,302 | B1 | 6/2004 | McDaniel |
| 6,833,415 | B2 | 12/2004 | Kendrick |
| 7,037,987 | B2 | 5/2006 | Goodall et al. |
| 7,078,362 | B2 | 7/2006 | Nagy |
| 7,098,278 | B2 | 8/2006 | Goodall et al. |
| 7,256,296 | B2 | 8/2007 | Diamond et al. |
| 7,387,980 | B2 | 6/2008 | Diamond et al. |
| 2004/0059070 | A1 | 3/2004 | Whitte et al. |
| 2010/0076167 | A1 | 3/2010 | McDaniel et al. |

FOREIGN PATENT DOCUMENTS

| | | |
|---|---|---|
| WO | WO 02/49758 | 6/2002 |
| WO | WO 2011/156921 A2 | 12/2011 |
| WO | WO 2011/156921 A3 | 12/2011 |

OTHER PUBLICATIONS

Pinnavaia, T. J., "Intercalated Clay Catalysts," Science, vol. 220, Issue 4595, (1983), pp. 365-371.

Thomas, J. M., "Sheet Silicate Intercalates: New Agents for Unusual Chemical Conversions," Intercalation Chemistry (S. Whittington and A. Jacobson, Eds.), Academic Press, Inc., Ch. 3, (1982), pp. 55-99.

Li, et al., "Coordination Copolymerization of Severely Encumbered Isoalkenes with Ethylene: Enhanced Enchainment Mediated by Binuclear Catalysts and Cocatalysts," J. Am. Chem. Soc., 2005, 127, pp. 14756-14768.

*Modern Plastics Encyclopedia*, Mid-Nov. 1995 Issue, vol. 72, No. 12, 3 pages.

*Film Extrusion Manual—Process, Materials, Properties*, TAPPI Press, 1992, 16 pages.

Frøseth, M., et al., "Synthesis and characterization of novel Pd(II) and Pt(II) complexes with 5-ring chelating iminoylcarbene ligands," *J. Organometallic Chem.*, 2005, 690, 6125-6132.

Warkentin, John, "2,5-Dihydro-1,3,4-oxadiazoles and Bis(heteroatom-substituted)carbenes," Accounts of Chemical Research, vol. 42, No. 1, Jan. 2009, pp. 205-212.

Murray, et al, "Pyridyl-Imine Derived Olefm Polymerization Catalysts," Proceedings Published 2002 by the American Chemical Society, p. 294.

DeWaele, et al., "Synthesis of Hafnium and Zirconium Imino—Amido Complexes from Bis-imine Ligands. A New Family of Olefin Polymerization Catalysts," *Organometallics* 2007, 26, pp. 3896-3899.

Arduengo, III, Anthony, "Looking for Stable Carbenes: The Difficulty in Starting Anew," Accounts of Chemical Research, vol. 32, No. 11, 1999, pp. 913-921.

Bol et al., Unexpected Carbon—Carbon Coupling Between Organic Cyanides and an Isopropyl β-Carbon in a Hafnium Ene Diamide Complex, *Organometallics* 1992, 11, pp. 1981-1983.

Poyatos, et al, Complexes with Poly(N-heterocyclic carbene) Ligands: Structural Features and Catalytic Applications, *Chemical Reviews*, 2009, 109, pp. 3677-3707.

Hu, et al, "The Zirconium Benzyl Mediated C-N Bond Cleavage of an Amino-Linked N-Heterocyclic Carbene," *Organometallics* 2010, vol. 29, No. 3, pp. 516-518.

Badaj, et al, "Synthesis and Structural Characterization of Nickel(II) Complexes with Imino-N-heterocyclic Carbene Heteroditopic Ligands," *Organometallics*, 2012, vol. 31, pp. 1103-1111.

Larocque, et al, "New stable aryl-substituted acyclic imino-$N$-heterocyclic carbine: synthesis, characterization and coordination to early transition metals†," *Dalton Transactions*, 2011, 40, pp. 12705-12712.

Thagfi, et al., "Synthesis and Structural Characterization of the First Copper(I) Complexes with Bis(imino)-N-heterocyclic Carbene NCN Pincer Ligands," *Organmetallics*, 2010, 29, pp. 3133-3138.

Hawley's Condensed Chemical Dictionary, 11th Ed., John Wiley & Sons, 1995, 3 pages.

Cotton et al., Advanced Inorganic Chemistry, 6th Ed., Wiley-Interscience, 1999, 4 pages.

Spencer et al., entitled "Synthesis and Reactivity of Zirconium and Hafnium Complexes Incorporating Chelating Diamido-N-Heterocyclic-Carbene Ligands," *Journal of Organometallic Chemistry* 690 (2005), pp. 5788-5803.

McGuinness, David entitled Alkene Oligomerisation and Polymerisation with Metal-NHC Based Catalysts, published in *Dalton Transactions*, (2009), pp. 6915-6923.

Wanniarachchi et al., entitled "An Unusually Static, Sterically Hindered Silver Bis(N-heterocyclic carbine) Complex and Its Use in Transmetalation," published in *Organometallics*, vol. 23, No. 25, (2004), pp. 5881-5884.

Ahlemann et al., entitled "Preparation and Reactions of 2,4,6-tris(trifluoromethyl) Phenylamine," published in the *Journal of Fluorine Chemistry* 87 (1998), pp. 87-90.

Stanlake, et al., entitled, "Rare-Earth Amidate Complexes. Easily Accessed Initiators for ε-Caprolactone Ring-Opening Polymerization," published in *Inorganic Chemistry Article* (2008), vol. 47, pp. 8062-8068.

Sanmartin, et al., entitled "Synthesis and Biological Evaluation of New Symmetrical Derivatives as Cytotoxic Agents and Apoptosis Inducers," published in *Bioorganic & Medicinal Chemistry*, vol. 13 (2005), pp. 2031-2044.

Small, et al., entitled "Highly Active Iron and Cobalt Catalysts for the Polymerization of Ethylene," published in *J. Am. Chem. Soc.* 1998, 120, pp. 4049-4050.

Hachiya, et al., entitled "Stereodivergent Synthesis of β-Lactams Using Thermal Rearrangement of Aminocyclobutenones," published in *Organic Letters*, 2009, vol. 11, No. 15, pp. 3266-3268.

Challis et al., entitled "Some Amines and Amides Derived from Vanillin," 1947, pp. 613-618.

Coleman, et al., entitled Silver(I) Complex of a New Imino-N-heterocyclic Carbene and Ligand Transfer to Palladium(II) and Rhodium(I) †, published in *Dalton Transactions*, (2003), pp. 2917-2922.

Jarrahpour et al., entitled "Synthesis of Structurally Diverse 2-Azetidinones via Staudinger Reaction on a Solid Support," published in *The Chemical Society of Japan*, vol. 84, No. 3, (2011), pp. 320-327.

Mohamed et al., entitled "Synthesis and Biological Activity of Some 3-Heterocyclyl-4-Hydroxy-6-Methyl-2 (1$H$)-Quinolones," published in the Indian Journal of Chemistry, vol. 34B, Jan. 1995, pp. 21-26.

Britovsek et al., entitled "Novel Olefin Polymerization Catalysts Based on Iron and Cobalt," published in *Chem Commun.*, 1998, pp. 849-850.

Douthwaite et al., entitled "The Synthesis of a di-$N$-Heterocyclic Carbene-Amido Complex of Palladium(II)†," published in *Chem, Commun.*, 2004, pp. 698-699.

Larocque et al., entitled "Coordination Chemistry of Bidentate and Tridentate N-Aryl-Substituted Imino-N-Heterocyclic Carbene Ligands," presented at the Inorganic Discussion Weekend 2012 Abstract, Poster No. 44, York University, 4700 Keele Street, Toronto, ON M3J 1P3. 1 page.

\* cited by examiner

IMINO CARBENE COMPOUNDS AND DERIVATIVES, AND CATALYST COMPOSITIONS MADE THEREFROM

REFERENCE TO RELATED APPLICATION

This application claims the benefit of U.S. Provisional Application Ser. No. 61/477,281, filed on Apr. 20, 2011, the disclosure of which is incorporated herein by reference in its entirety.

BACKGROUND OF THE INVENTION

The present invention relates generally to the field of olefin polymerization catalysis, catalyst compositions, methods for the polymerization and copolymerization of olefins, and polyolefins. More specifically, this invention relates to imino carbene compounds and their derivatives, and catalyst compositions employing such compounds.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

The present invention discloses imino carbene compounds and compounds derived from imino carbene compounds. These imino carbene compounds and their derivatives can be used in catalyst systems for the polymerization of olefins and for other catalytic processes.

According to an aspect of the present invention, imino carbene compounds having the following formula are disclosed:

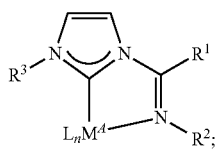

(I)

or a partially saturated or saturated version thereof;
wherein:
$M^A$ is a transition metal;
$R^1$, $R^2$, and $R^3$ are independently a substituent comprising atoms selected from the group consisting of H and Group 13 to 17 elements, and optionally two of $R^1$, $R^2$, and $R^3$ are connected to form a cyclic moiety;
each L is independently a ligand comprising atoms selected from the group consisting of H and Group 13 to 17 elements, and optionally two or more L ligands are connected to form a cyclic moiety; and
n is 2, 3 or 4.

According to another aspect of the present invention, tridentate bis(imino) carbene compounds having the following formula are disclosed:

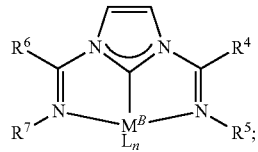

(II)

or a partially saturated or saturated version thereof;
wherein:
$M^B$ is a transition metal;
$R^4$, $R^5$, $R^6$, and $R^7$ are independently a substituent comprising atoms selected from the group consisting of H and Group 13 to 17 elements, and optionally two of $R^4$, $R^5$, $R^6$, and $R^7$ are connected to form a cyclic moiety;
each L is independently a ligand comprising atoms selected from the group consisting of H and Group 13 to 17 elements, and optionally two or more L ligands are connected to form a cyclic moiety; and
n is 1, 2, or 3.

According to another aspect of the present invention, bridged imino carbene compounds having the following formula are disclosed:

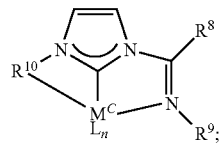

(III)

or a partially saturated or saturated version thereof;
wherein:
$M^C$ is a transition metal;
$R^8$, $R^9$ and $R^{10}$ are independently a substituent comprising atoms selected from the group consisting of H and Group 13 to 17 elements, and optionally two of $R^8$, $R^9$ and $R^{10}$ are connected to form a cyclic moiety;
each L is independently a ligand comprising atoms selected from the group consisting of H and Group 13 to 17 elements, and optionally two or more L ligands are connected to form a cyclic moiety; and
n is 1, 2, or 3.

According to another aspect of the present invention, dimer compounds having the following formula are disclosed:

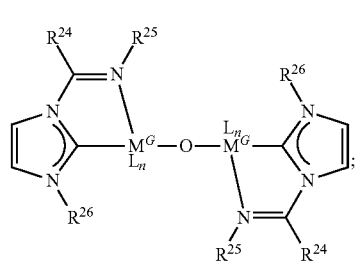

(VII)

or a partially saturated or saturated version thereof;
wherein:
each $M^G$ is a transition metal;
each $R^{24}$, $R^{25}$, and $R^{26}$ is independently a substituent comprising atoms selected from the group consisting of H and Group 13 to 17 elements, and optionally two of $R^{24}$, $R^{25}$, and $R^{26}$ are connected to form a cyclic moiety;

each L is independently a ligand comprising atoms selected from the group consisting of H and Group 13 to 17 elements, and optionally two or more L ligands are connected to form a cyclic moiety; and each n is independently 1, 2, or 3.

According to another aspect of the present invention, bis-carbene compounds having the following formula are disclosed:

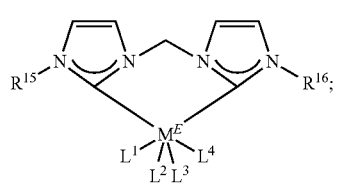

(V)

or a partially saturated or saturated version thereof;
wherein:

$M^E$ is Ti, Zr, or Hf;

$R^{15}$ and $R^{16}$ are independently a substituent comprising atoms selected from the group consisting of H and Group 13 to 17 elements, and optionally $R^{15}$ and $R^{16}$ are connected to form a cyclic moiety; and $L^1$, $L^2$, $L^3$, and $L^4$ are independently a ligand comprising atoms selected from the group consisting of H and Group 13 to 17 elements, and optionally two or more of $L^1$, $L^2$, $L^3$; and $L^4$ ligands are connected to form a cyclic moiety.

According to another aspect of the present invention, imino-enediamide compounds having the following formula are disclosed:

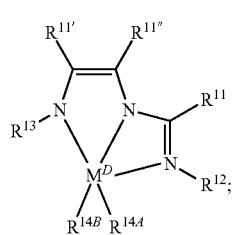

(IV)

or a partially saturated or saturated version thereof;
wherein:

$M^D$ is a transition metal;

$R^{11'}$, $R^{11''}$, $R^{11'''}$, $R^{12}$, and $R^{13}$ are independently a substituent comprising atoms selected from the group consisting of H and Group 13 to 17 elements, and optionally two of $R^{11'}$, $R^{11''}$, $R^{11'''}$, $R^{12}$, and $R^{13}$ are connected to form a cyclic moiety; and $R^{14A}$ and $R^{14B}$ are independently H, F, Cl, Br, I, or a hydrocarbyl, hydrocarbyloxide, hydrocarbylamino, hydrocarbylsilyl, or halogenated hydrocarbyl group, any of which having up to 48 carbon atoms.

The present invention also incorporates and encompasses derivatives of imino carbene ligands in which the imine nitrogen has been converted to an anionic group (e.g., such as an amide) after coordination to the metal. This can occur, for example, by attack of alkyl, hydrocarbyl, or hydride groups, either external or initially bound to the same metal, at the imine carbon. In addition, this invention incorporates derivatives in which the carbene moiety has been converted to an anionic or dianionic group by similar reactions (e.g., see formula (IV)). These reactions, which convert the imino carbene into one or more anionic forms, can occur prior to or during treatment with activators in catalyst compositions and polymerization reactions.

Catalyst compositions containing imino carbene compounds and/or their derivatives also are provided by the present invention. For instance, the catalyst composition can comprise at least one activator and a compound having formula (I), a compound having formula (II), a compound having formula (III), a compound having formula (IV), a compound having formula (V), and/or a compound having formula (VII).

The present invention also contemplates an olefin polymerization process, and this process can comprise contacting a catalyst composition with an olefin monomer and optionally an olefin comonomer under polymerization conditions to produce an olefin polymer. The catalyst composition can comprise an activator and one or more of the compounds disclosed herein, i.e., a compound having formula (I), a compound having formula (II), a compound having formula (III), a compound having formula (IV), a compound having formula (V), a compound having formula (VII), or combinations thereof.

Olefin homopolymers, copolymers, terpolymers, and the like, can be produced using the catalyst compositions and methods for olefin polymerization disclosed herein, and these polymers can be used to produce various articles of manufacture.

DEFINITIONS

Figure 1:
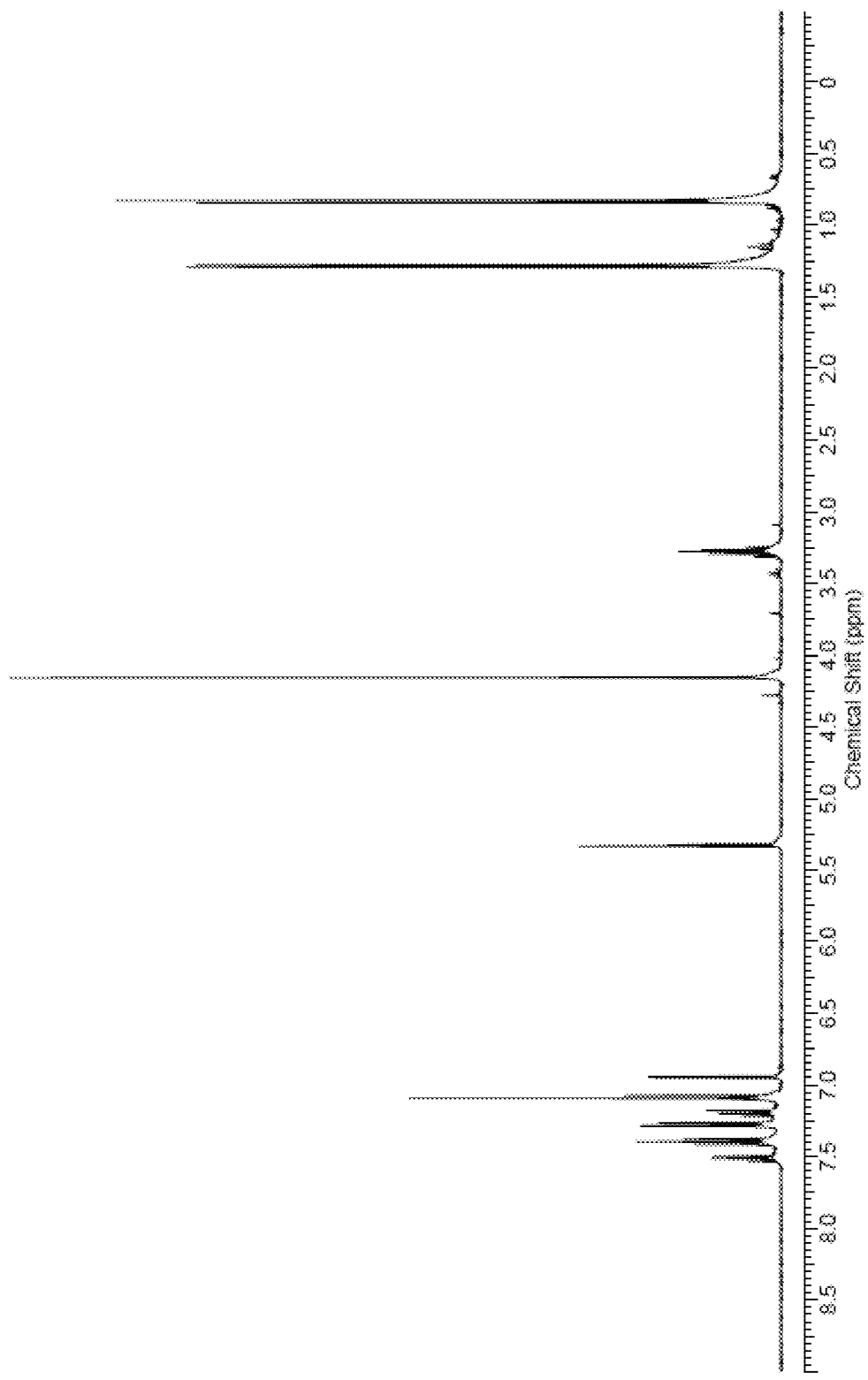
FIG. 1 presents a $^1$H NMR spectrum of Zr-complex 3 of Example 3.

To define more clearly the terms used herein, the following definitions are provided. To the extent that any definition or usage provided by any document incorporated herein by reference conflicts with the definition or usage provided herein, the definition or usage provided herein controls.

"Hydrocarbyl" is used herein to specify a hydrocarbon radical group that includes, but is not limited to, aryl, alkyl, cycloalkyl, alkenyl, cycloalkenyl, cycloalkadienyl, alkynyl, aralkyl, aralkenyl, aralkynyl, and the like, and includes all substituted, unsubstituted, linear, and/or branched derivatives thereof. Unless otherwise specified, the hydrocarbyl groups of this invention typically comprise up to 36 carbon atoms. In other aspects, hydrocarbyl groups can have up to 24 carbon atoms, for instance, up to 18 carbon atoms, up to 12 carbon atoms, up to 10 carbon atoms, up to 8 carbon atoms, or up to 6 carbon atoms. A hydrocarbyloxide group, therefore, is used generically to include both alkoxide and aryloxide groups, and these groups can comprise up to about 36 carbon atoms, unless otherwise specified. Illustrative and non-limiting examples of alkoxide and aryloxide groups (i.e., hydrocarbyloxide groups) include methoxy, ethoxy, propoxy, butoxy, phenoxy, substituted phenoxy, and the like. The term hydrocarbylamino group is used generically to refer collectively to alkylamino, arylamino, dialkylamino, and diarylamino groups, and the like. Unless otherwise specified, the hydrocarbylamino groups of this invention comprise up to about 36 carbon atoms. Hydrocarbylsilyl groups include, but are not limited to, alkylsilyl groups, alkenylsilyl groups, arylsilyl groups, arylalkylsilyl groups, and the like, which have up to about 36 carbon atoms, unless otherwise specified. For example, illustrative hydrocarbylsilyl groups can include trimethylsilyl and phenyloctylsilyl: A halogenated hydrocarbyl group is meant to indicate a hydrocarbyl group having one or more halogen atoms replacing an equivalent number of hydrogen atoms in the hydrocarbyl group. The halogenated hydrocarbyl group often can be a halogenated alkyl group, a halogenated cycloalkyl group, a halogenated aryl group, or a halogenated aralkyl group. Representative and non-limiting halogenated hydrocarbyl groups include, but are not limited to, trifluoromethyl ($CF_3$), pentafluorophenyl, trifluoromethylphenyl (e.g., 4-trifluoromethylphenyl), and the like, which have up to about 36 carbon atoms, unless otherwise specified. These hydrocarbyloxide, hydrocarbylamino; hydrocarbylsilyl, and halogenated hydrocarbyl groups can have up to 24 carbon atoms; alternatively, up to 18 carbon atoms; alternatively, up to 12 carbon atoms; alternatively, up to 10 carbon atoms; or alternatively, up to 8 carbon atoms, in other aspects of the present invention.

Unless otherwise specified, alkyl groups and alkenyl groups described herein are intended to include all structural isomers, linear or branched, of a given moiety; for example, all enantiomers and all diastereomers are included within this definition. As an example, unless otherwise specified, the term propyl is meant to include n-propyl and iso-propyl, while the term butyl is meant to include n-butyl, iso-butyl, t-butyl, sec-butyl, and so forth. For instance, non-limiting examples of octyl isomers include 2-ethyl hexyl and neooctyl. Suitable examples of alkyl groups which can be employed in the present invention include, but are not limited to, methyl, ethyl, propyl, butyl, pentyl, hexyl, heptyl, octyl, nonyl, decyl, and the like. Illustrative examples of alkenyl groups within the scope of the present invention include, but are not limited to, ethenyl, propenyl, butenyl, pentenyl, hexenyl, heptenyl, octenyl, nonenyl, decenyl, and the like. The alkenyl group can be a terminal alkenyl group, but this is not a requirement. For instance, specific alkenyl group substituents can include, but are not limited to, 3-butenyl, 4-pentenyl, 5-hexenyl, 6-heptenyl, 7-octenyl, 3-methyl-3-butenyl, 4-methyl-3-pentenyl, 1,1-dimethyl-3-butenyl, 1,1-dimethyl-4-pentenyl, and the like.

In this disclosure, "aryl" is meant to include aryl and arylalkyl groups, and these include, but are not limited to, phenyl, alkyl-substituted phenyl, naphthyl, alkyl-substituted naphthyl, phenyl-substituted alkyl, naphthyl-substituted alkyl, and the like. Hence, non-limiting examples of such "aryl" moieties that can be used in the present invention include phenyl, tolyl, benzyl, dimethylphenyl (e.g., 2,6-dimethylphenyl), trimethylphenyl (e.g., 2,4,6-trimethylphenyl), phenylethyl, phenylpropyl, phenylbutyl, 2-propyl-phenylethyl, 2,6-diisopropylphenyl, and the like. Unless otherwise specified, any substituted aryl moiety used herein is meant to include all regioisomers; for example, the term tolyl is meant to include any possible substituent position, that is, ortho, meta, or para.

The term "polymer" is used herein generically to include olefin homopolymers, copolymers, terpolymers, and so forth. A copolymer is derived from an olefin monomer and one olefin comonomer, while a terpolymer is derived from an olefin monomer and two olefin comonomers. Accordingly, "polymer" encompasses copolymers, terpolymers, etc., derived from any olefin monomer and comonomer(s) disclosed herein. Similarly, an ethylene polymer would include ethylene homopolymers, ethylene copolymers, ethylene terpolymers, and the like. As an example, an olefin copolymer, such as an ethylene copolymer, can be derived from ethylene and a comonomer, such as 1-butene, 1-hexene, or 1-octene. If the monomer and comonomer were ethylene and 1-hexene, respectively, the resulting polymer would be categorized an as ethylene/1-hexene copolymer.

In like manner, the scope of the term "polymerization" includes homopolymerization, copolymerization, terpolymerization, etc. Therefore, a copolymerization process would involve contacting one olefin monomer (e.g., ethylene) and one olefin comonomer (e.g., 1-hexene) to produce a copolymer.

The term "imino carbene compound/derivative" is used herein to refer to, collectively, any of the compounds disclosed herein having formula (I), having formula (II), having formula (III), having formula (IV), having formula (IV-A), having formula (IV-B), having formula (V), or having formula (VII). Moreover, this includes partially saturated or saturated versions of any of these compounds.

The term "co-catalyst" is used generally herein to refer to organoaluminum compounds that can constitute one component of a catalyst composition. Additionally, "co-catalyst" can refer to other components of a catalyst composition including, but not limited to, aluminoxanes, organoboron or organoborate compounds, and ionizing ionic compounds, as disclosed herein, when used in addition to an activator-support. The term "co-catalyst" is used regardless of the actual function of the compound or any chemical mechanism by which the compound may operate. In one aspect of this invention, the term "co-catalyst" is used to distinguish that component of the catalyst composition from the imino carbene compound/derivative.

The terms "chemically-treated solid oxide," "activator-support," "treated solid oxide compound," and the like, are used herein to indicate a solid, inorganic oxide of relatively high porosity, which can exhibit Lewis acidic or Brønsted acidic behavior, and which has been treated with an electron-withdrawing component, typically an anion, and which is calcined. The electron-withdrawing component is typically an electron-withdrawing anion source compound. Thus, the chemically-treated solid oxide can comprise a calcined contact product of at least one solid oxide with at least one electron-withdrawing anion source compound. Typically, the chemically-treated solid oxide comprises at least one acidic solid oxide compound. The terms "support" and "activator-support" are not used to imply these components are inert, and such components should not be construed as an inert component of the catalyst composition. The activator-support of the present invention can be a chemically-treated solid oxide. The term "activator," as used herein, refers generally to a substance that is capable of converting an imino carbene compound/derivative into a catalyst that can polymerize olefins, or converting a contact product of an imino carbene compound/derivative and a component that provides an activatable ligand (e.g., an alkyl, a hydride) to the imino carbene compound/derivative, when the imino carbene compound/derivative does not already comprise such a ligand, into a catalyst that can polymerize olefins. This term is used regardless of the actual activating mechanism. Illustrative activators include activator-supports, aluminoxanes, organoboron or organoborate compounds, ionizing ionic compounds, and the like. Aluminoxanes, organoboron or organoborate compounds, and ionizing ionic compounds generally are referred to as activators if used in a catalyst composition in which an activator-support is not present. If the catalyst composition contains an activator-support, then the aluminoxane, organoboron or organoborate, and ionizing ionic materials are typically referred to as co-catalysts.

The term "fluoroorgano boron compound" is used herein with its ordinary meaning to refer to neutral compounds of the form $BY_3$. The term "fluoroorgano borate compound" also has its usual meaning to refer to the monoanionic salts of a fluoroorgano boron compound of the form $[cation]^+[BY_4]^-$, where Y represents a fluorinated organic group. Materials of these types are generally and collectively referred to as "organoboron or organoborate compounds."

The terms "catalyst composition," "catalyst mixture," "catalyst system," and the like, do not depend upon the actual product or composition resulting from the contact or reaction of the initial components of the claimed catalyst composition/mixture/system, the nature of the active catalytic site, or the fate of the co-catalyst, the imino carbene compound/derivative, any olefin monomer used to prepare a precontacted mixture, or the activator (e.g., activator-support), after combining these components. Therefore, the terms "catalyst composition," "catalyst mixture," "catalyst system," and the like, encompass the initial starting components of the composition, as well as whatever product(s) may result from contacting these initial starting components, and this is inclusive of both heterogeneous and homogenous catalyst systems or compositions.

The term "contact product" is used herein to describe compositions wherein the components are contacted together in any order, in any manner, and for any length of time. For example, the components can be contacted by blending or mixing. Further, contacting of any component can occur in the presence or absence of any other component of the compositions described herein. Combining additional materials or components can be done by any suitable method. Further, the term "contact product" includes mixtures, blends, solutions, slurries, reaction products, and the like, or combinations thereof. Although "contact product" can include reaction products, it is not required for the respective components to react with one another. Similarly, the term "contacting" is used herein to refer to materials which may be blended, mixed, slurried, dissolved, reacted, treated, or otherwise contacted in some other manner.

The term "precontacted" mixture is used herein to describe a first mixture of catalyst components that are contacted for a first period of time prior to the first mixture being used to form a "postcontacted" or second mixture of catalyst components that are contacted for a second period of time. Typically, the precontacted mixture describes a mixture of imino carbene compound/derivative (one or more than one), olefin monomer (or monomers), and organoaluminum compound (or compounds), before this mixture is contacted with an activator-support(s) and optional additionl organoaluminum compound. Thus, precontacted describes components that are used to contact each other, but prior to contacting the components in the second, postcontacted mixture. Accordingly, this invention may occasionally distinguish between a component used to prepare the precontacted mixture and that component after the mixture has been prepared. For example, according to this description, it is possible for the precontacted organoaluminum compound, once it is contacted with the imino carbene compound/derivative and the olefin monomer, to have reacted to form at least one different chemical compound, formulation, or structure from the distinct organoaluminum compound used to prepare the precontacted mixture. In this case, the precontacted organoaluminum compound or component is described as comprising an organoaluminum compound that was used to prepare the precontacted mixture.

Additionally, the precontacted mixture can describe a mixture of imino carbene compound(s)/derivative(s) and organoaluminum compound(s), prior to contacting this mixture with an activator-support(s). This precontacted mixture also can describe a mixture of imino carbene compound(s)/derivative(s), olefin monomer(s), and activator-support(s), before this mixture is contacted with an organoaluminum co-catalyst compound or compounds.

Similarly, the term "postcontacted" mixture is used herein to describe a second mixture of catalyst components that are contacted for a second period of time, and one constituent of which is the "precontacted" or first mixture of catalyst components that were contacted for a first period of time. Typically, the term "postcontacted" mixture is used herein to describe the mixture of imino carbene compound(s)/derivative(s), olefin monomer(s), organoaluminum compound(s), and activator-support(s) formed from contacting the precontacted mixture of a portion of these components with any additional components added to make up the postcontacted mixture. Often, the activator-support comprises a chemically-treated solid oxide. For instance, the additional component added to make up the postcontacted mixture can be a chemically-treated solid oxide (one or more than one), and optionally, can include an organoaluminum compound which is the same as or different from the organoaluminum compound used to prepare the precontacted mixture, as described herein. Accordingly, this invention may also occasionally distinguish between a component used to prepare the postcontacted mixture and that component after the mixture has been prepared.

Although any methods, devices, and materials similar or equivalent to those described herein can be used in the practice or testing of the invention, the typical methods, devices and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

For any particular compound disclosed herein, any general or specific structure presented also encompasses all conformational isomers, regioisomers, and stereoisomers that may arise from a particular set of substituents, unless stated otherwise. Similarly, unless stated otherwise, the general or specific structure also encompasses all enantiomers, diastereomers, and other optical isomers whether in enantiomeric or racemic forms, as well as mixtures of stereoisomers, as would be recognized by a skilled artisan.

Applicants disclose several types of ranges in the present invention. These include, but are not limited to, a range of number of atoms, a range of weight ratios, a range of molar ratios, a range of surface areas, a range of pore volumes, a range of catalyst activities, and so forth. When Applicants disclose or claim a range of any type, Applicants' intent is to disclose or claim individually each possible number that such a range could reasonably encompass, including end points of the range as well as any sub-ranges and combinations of sub-ranges encompassed therein. For example, when the Applicants disclose or claim a chemical moiety having a certain number of carbon atoms, Applicants' intent is to disclose or claim individually every possible number that such a range could encompass, consistent with the disclosure herein. For example, the disclosure that a moiety is a $C_1$ to $C_{18}$ hydrocarbyl group, or in alternative language a hydrocarbyl group having up to 18 carbon atoms, as used herein, refers to a moiety that can be selected independently from a hydrocarbyl group having 1, 2, 3, 4, 5, 6, 7, 8, 9, 10, 11, 12, 13, 14, 15, 16, 17, or 18 carbon atoms, as well as any range between these two numbers (for example, a $C_1$ to $C_8$ hydrocarbyl group), and also including any combination of ranges between these two numbers (for example, a $C_2$ to $C_4$ and a $C_{12}$ to $C_{16}$ hydrocarbyl group).

Similarly, another representative example follows for the weight ratio of an organoaluminum compound to an activator-support in a catalyst composition provided in one aspect of this invention. By a disclosure that the weight ratio of the organoaluminum compound to the activator-support can be in a range from about 3:1 to about 1:100, Applicants intend to recite that the weight ratio can be about 3:1, about 2:1, about 1:1, about 1:2, about 1:3, about 1:4, about 1:5, about 1:10, about 1:20, about 1:30, about 1:40, about 1:50, about 1:60, about 1:70, about 1:80, about 1:90, or about 1:100. Additionally, the weight ratio of the organoaluminum compound to the activator-support can be within any range from about 3:1 to about 1:100 (for example, from about 1:1 to about 1:50), and this also includes any combination of ranges between about 3:1 to about 1:100 (for example, the weight ratio is in a range from about 2:1 to about 1:2, or from about 1:5 to about 1:25). Likewise, all other ranges disclosed herein should be interpreted in a manner similar to these two examples.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants may be unaware of at the time of the filing of the application.

The terms "a," "an," "the," etc., are intended to include plural alternatives, e.g., at least one, unless otherwise specified. For instance, the disclosure of "an activator-support" or "an imino carbene compound/derivative" is meant to encompass one, or mixtures or combinations of more than one, activator-support or imino carbene compound/derivative, respectively.

While compositions and methods are described in terms of "comprising" various components or steps, the compositions and methods can also "consist essentially of" or "consist of" the various components or steps. For example, a catalyst composition of the present invention can comprise; alternatively, can consist essentially of or alternatively, can consist of (i) an imino carbene compound/derivative, and (ii) an activator.

Throughout this disclosure, these abbreviations are used: Me—methyl, Ph—phenyl; and t-Bu—tert-butyl or t-butyl.

DETAILED DESCRIPTION OF THE INVENTION

The present invention is directed generally to imino carbene compounds and their derivatives, methods for synthesizing these compounds, catalyst compositions containing these compounds, methods for preparing catalyst compositions, methods for using the catalyst compositions to polymerize olefins, the polymer resins produced using such catalyst compositions, and articles produced using these polymer resins.

Imino Carbene Compounds

Imino carbene compounds of the present invention can have the following structural formula:

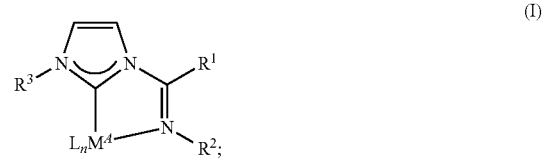

(I)

or a partially saturated or saturated version thereof;
wherein:
$M^4$ is a transition metal;
$R^1$, $R^2$, and $R^3$ are independently a substituent comprising atoms selected from the group consisting of H and Group 13 to 17 elements, and optionally two of $R^1$, $R^2$, and $R^3$ are connected to form a cyclic moiety;
each L is independently a ligand comprising atoms selected from the group consisting of H and Group 13 to 17 elements, and optionally two or more L ligands are connected to form a cyclic moiety; and
n is 2, 3 or 4.

Unless otherwise specified, formula (I) above, any other structural formulas disclosed herein (e.g., formula (II), formula (III), formula (IV), formula (IV-A), formula (IV-B), formula (V), and formula (VII)), and any species or compound disclosed herein are not designed to show stereochemistry or isomeric positioning of the different moieties (e.g., these formulas are not intended to display cis or trans isomers, or R or S diastereoisomers), although such compounds are contemplated and encompassed by these formulas and/or structures.

In formula (I), $M^4$ is a transition metal. For instance, $M^4$ can be a Group 3, 4, 5, or 6 transition metal, such as Sc, Y, Ti, Zr, Hf, V, Nb, Ta, Cr, and Mo, among others. In another aspect of this invention, $M^4$ is Ti, Zr, or Hf. In other aspects, $M^4$ is Ti, or $M^4$ is Zr, or $M^4$ is Hf.

R¹, R², and R³ are independently a substituent comprising atoms selected from the group consisting of H and Group 13 to 17 elements, and optionally two of R¹, R², and R³ are connected to form a cyclic moiety. Thus, R¹, R², and R³ can comprise atoms including, but not limited to, H, B, Al, C, Si, N, P, O, S, F, Cl, Br, I, and combinations thereof. According to one aspect of this invention, R¹, R², and R³ independently can contain up to 50 non-hydrogen atoms. According to another aspect, R¹, R², and R³ independently can contain up to 25 non-hydrogen atoms; alternatively, up to 15 non-hydrogen atoms; or alternatively, up to 10 non-hydrogen atoms.

Optionally, two of R¹, R², and R³ are connected to form a cyclic group, often having up to 36 carbon atoms, up to 24 carbon atoms, up to 18 carbon atoms, or up to 12 carbon atoms. In addition to carbon atoms, additional heteroatoms, such as nitrogen, oxygen, or sulfur, can be present in the ring system.

In another aspect of this invention, R¹, R², and R³ can be independently selected from the group consisting of H, halogen, alkyl, substituted alkyl, heteroalkyl, aryl, substituted aryl, heteroaryl, alkoxy, aryloxy, silyl, boryl, phosphino, amino, alkylthio, arylthio, hydrocarbyl, substituted hydrocarbyl, heteroatom-containing hydrocarbyl, a group having formula (Ia), and combinations thereof. In this aspect, R¹, R², and R³ independently can have up to 48 carbon atoms, up to 36 carbon atoms, up to 24 carbon atoms, up to 18 carbon atoms, up to 12 carbon atoms, or up to 6 carbon atoms. Formula (Ia) is

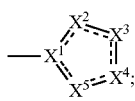

wherein:
X¹ is N, P, or —C($R^A$)$_p$—;
X², X³, and X⁴ are independently O, S, —C($R^A$)$_q$—, —N($R^A$)$_p$—, —P($R^A$)$_p$—, —N($R^B$)—, —P($R^B$)—, or —C($R^B$)($R^A$)$_q$—;
X⁵ is O, S, or —N($R^A$)$_p$—;
at least one, but no more than three, of X¹, X², X³, and X⁴ is C or —C($R^A$)$_q$—, respectively;
each p is 0 or 1 and each q is 1 or 2;
each $R^A$ is independently H, halogen, nitro, alkyl, substituted alkyl, heteroalkyl, aryl, heteroaryl, alkoxy, aryloxy, silyl, boryl, phosphino, amino, alkylthio, arylthio, or combinations thereof;
each $R^B$ is aryl, substituted aryl, or heteroaryl; and
optionally any combination of two or more of R¹, R², R³, $R^A$ and/or $R^B$ are joined together to form one or more optionally substituted fused ring systems.

In yet another aspect of this invention, R¹, R², and R³ are independently H, or a hydrocarbyl group, hydrocarbyloxide group, hydrocarbylamino group, hydrocarbylsilyl group, or halogenated hydrocarbyl group, any of which having up to 36 carbon atoms; alternatively, having up to 24 carbon atoms; or alternatively, having up to 18 carbon atoms. In some aspects, R¹, R², and R³ are independently H or a hydrocarbyl or halogenated hydrocarbyl group having up to 18 carbon atoms, while in other aspects, R¹, R², and R³ are independently H or an alkyl or aryl group having up to 18 carbon atoms. In yet another aspect, R¹, R², and R³ independently can be methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, benzyl, tolyl, 2,6-dimethylphenyl, 2,6-diisopropylphenyl, 2,4,6-trimethylphenyl, trifluoromethyl, pentafluorophenyl, or 4-trifluoromethylphenyl, and the like.

It is contemplated that R¹, R², and R³ are independently Me, t-Bu, Ph, CH₂-Ph, 2,4,6-trimethylphenyl, 2,6-dimethylphenyl, 2,6-diisopropylphenyl, trifluoromethyl, pentafluorophenyl, or 4-trifluoromethylphenyl in one aspect of this invention. In another aspect, R¹ is Ph, CH₂-Ph, 2,4,6-trimethylphenyl, 2,6-dimethylphenyl, or 2,6-diisopropylphenyl. Additionally or alternatively, R² can be Ph, CH₂-Ph, 2,4,6-trimethylphenyl, 2,6-dimethylphenyl, or 2,6-diisopropylphenyl. Additionally or alternatively, R³ can be Me, t-Bu, Ph, CH₂-Ph, 2,4,6-trimethylphenyl, 2,6-dimethylphenyl, or 2,6-diisopropylphenyl. In a further aspect, R³ is Me, t-Bu, or Ph; alternatively, R³ is Me; alternatively, R³ is t-Bu; or alternatively, R³ is Ph.

In accordance with another aspect of this invention, at least one of R¹, R², and R³ contains up to 50 non-hydrogen atoms and has one of the following structures:

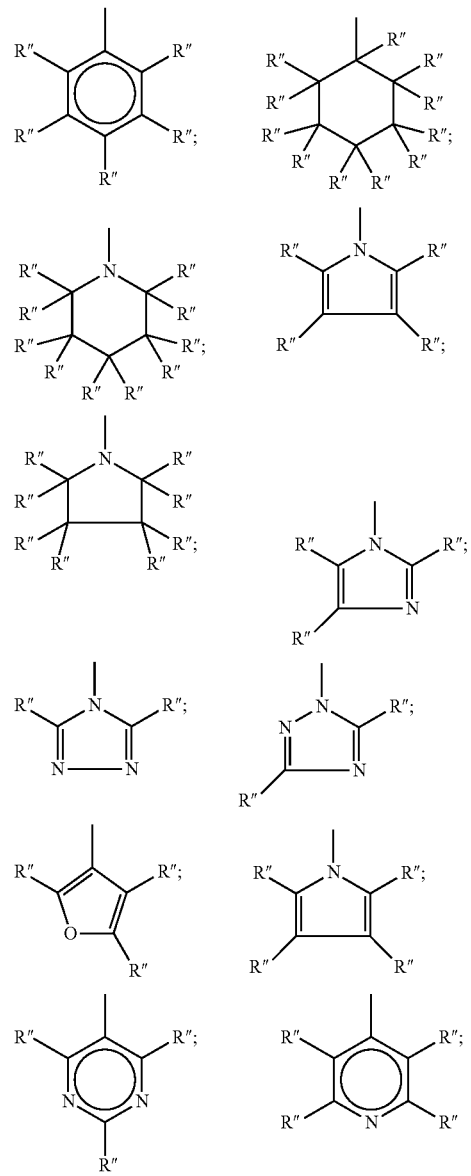

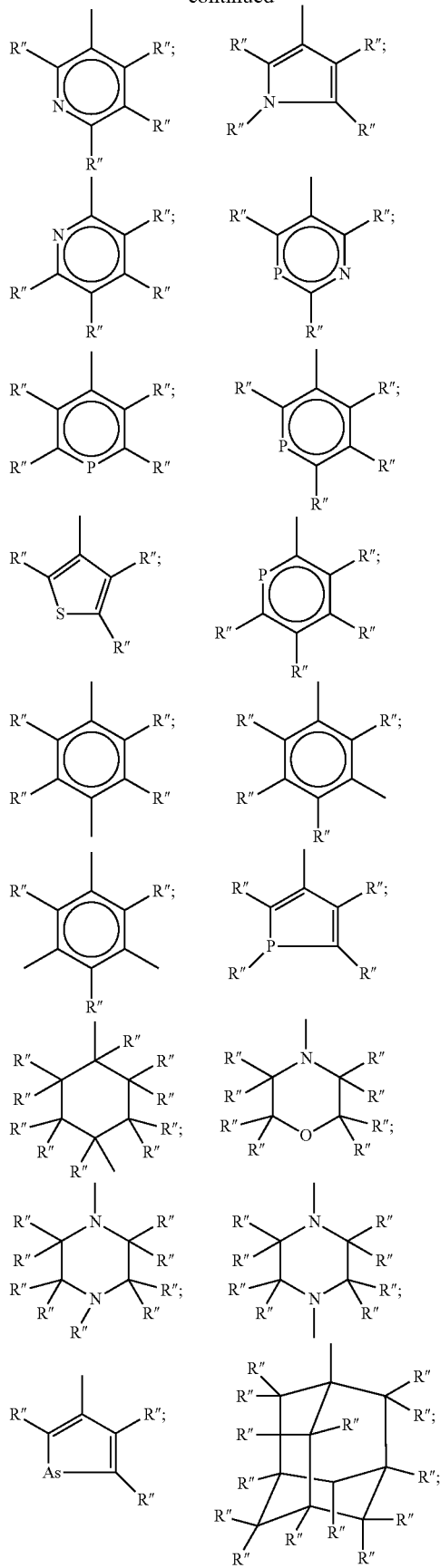
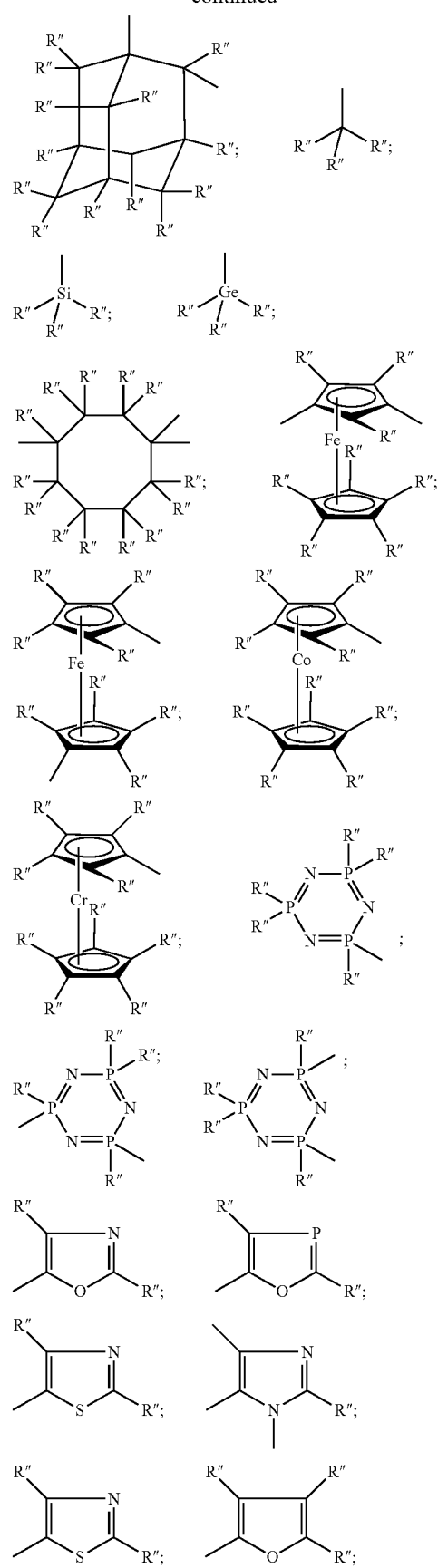

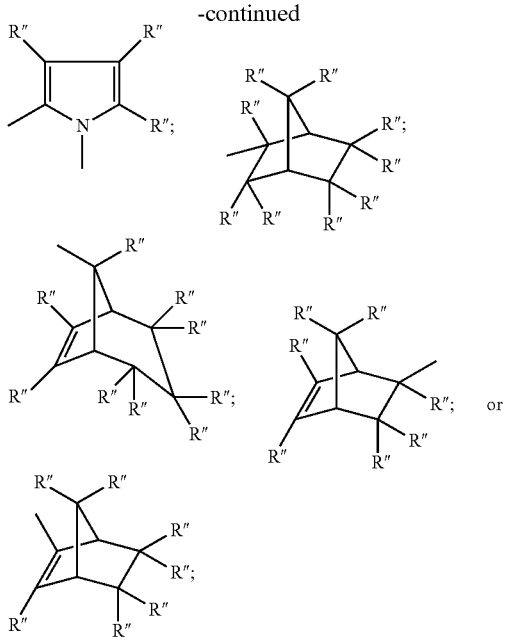

wherein each R" is independently H, a halogen, a halogen-containing group, or an alkyl, aryl, cycloalkyl, or heterocyclic group. Generally, R" has up to 18 carbon atoms, up to 12 carbon atoms, up to 8 carbon atoms, up to 6 carbon atoms, or up to 3 carbon atoms, in various aspects of this invention.

Each L in formula (I) is independently a ligand comprising atoms selected from the group consisting of H and Group 13 to 17 elements. Each L, therefore, can comprise atoms including, but not limited to, H, B, Al, C, Si, N, P, O, S, F, Cl, Br, I, and combinations thereof. According to one aspect of this invention, each L independently can contain up to 25 non-hydrogen atoms. In another aspect, each L independently can contain up to 18 non-hydrogen atoms or, alternatively, up to 12 non-hydrogen atoms. In yet another aspect, each L independently can contain up to 8 non-hydrogen atoms. These ligands may be covalently bonded to $M^A$, or ionically bonded to $M^A$.

Optionally, two or more L ligands can be connected to form a cyclic group, often having up to 36 carbon atoms, up to 24 carbon atoms, up to 18 carbon atoms, or up to 12 carbon atoms. Cyclic groups include cycloalkyl and cycloalkenyl moieties and such moieties can include, but are not limited to, cyclopentyl, cyclopentenyl, cyclohexyl, cyclohexenyl, and the like. Cyclic groups also include heterocyclic groups. Heteroatom-substituted cyclic groups can be formed with nitrogen, oxygen, or sulfur heteroatoms, for example. While these heterocyclic groups can have up to 12 or 18 or 24 or 36 carbons atoms, the heterocyclic groups can be 3-membered, 4-membered, 5-membered, 6-membered, or 7-membered groups in some aspects of this invention.

In one aspect, each L is independently F, Cl, Br, I, methyl, benzyl, phenyl, H, $BH_4$, $OBR_2$, or $SO_3R$, wherein R is an alkyl or aryl group, or a hydrocarbyloxide group, hydrocarbylamino group, hydrocarbylsilyl group, or halogenated hydrocarbyl group. The hydrocarbyloxide group, hydrocarbylamino group, hydrocarbylsilyl group, halogenated hydrocarbyl group, and R can have up to 18 carbon atoms; alternatively, up to 12 carbon atoms; or alternatively, up to 8 carbon atoms. In another aspect, each L independently can be F, Cl, Br, I, or a hydrocarbyl or halogenated hydrocarbyl group having up to 18 carbon atoms, for instance, up to 12 carbon atoms. In yet another aspect, each L independently can be F, Cl, Br, I, methyl, benzyl, or phenyl. In still another aspect, each L can be Cl.

In some aspects disclosed herein, each L independently can be H, halogen, alkyl, substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, or sulphate. In these and other aspects, each L independently can have up to 18 carbon atoms, or up to 12 carbon atoms, or up to 8 carbon atoms, or up to 6 carbon atoms.

In formula (I), n is 2, 3 or 4. According to one aspect of this invention, n is 2. In another aspect, n is 3. In yet another aspect, n is 4.

Tridentate Bis(imino) Carbene Compounds

Tridentate bis(imino) carbene compounds of the present invention can have the following structural formula:

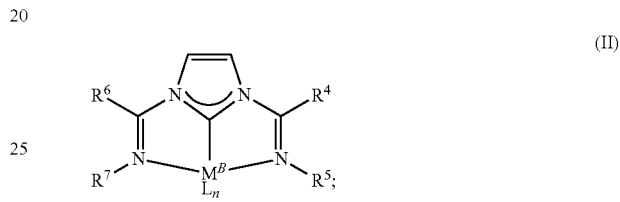

(II)

or a partially saturated or saturated version thereof;
wherein:
$M^B$ is a transition metal;
$R^4$, $R^5$, $R^6$, and $R^7$ are independently a substituent comprising atoms selected from the group consisting of H and Group 13 to 17 elements, and optionally two of $R^4$, $R^5$, $R^6$, and $R^7$ are connected to form a cyclic moiety;
each L is independently a ligand comprising atoms selected from the group consisting of H and Group 13 to 17 elements, and optionally two or more L ligands are connected to form a cyclic moiety; and
n is 1, 2, or 3.

In formula (II), $M^B$ is a transition metal. For instance, $M^B$ can be a Group 3, 4, 5, or 6 transition metal, such as Sc, Y, Ti, Zr, Hf, V, Nb, Ta, Cr, and Mo, among others. In another aspect of this invention, $M^B$ is Ti, Zr, or Hf. In other aspects, $M^B$ is Ti, or $M^B$ is Zr, or $M^B$ is Hf.

$R^4$, $R^5$, $R^6$, and $R^7$ are independently a substituent comprising atoms selected from the group consisting of H and Group 13 to 17 elements, and optionally two of $R^4$, $R^5$, $R^6$, and $R^7$ are connected to form a cyclic moiety. Thus, $R^4$, $R^5$, $R^6$, and $R^7$ can comprise atoms including, but not limited to, H, B, Al, C, Si, N, P, O, S, F, Cl, Br, I, and combinations thereof. According to one aspect of this invention, $R^4$, $R^5$, $R^6$, and $R^7$ independently can contain up to 50 non-hydrogen atoms. According to another aspect, $R^4$, $R^5$, $R^6$, and $R^7$ independently can contain up to 25 non-hydrogen atoms; alternatively, up to 15 non-hydrogen atoms; or alternatively, up to 10 non-hydrogen atoms.

Optionally, two of $R^4$, $R^5$, $R^6$, and $R^7$ are connected to form a cyclic group, often having up to 36 carbon atoms, up to 24 carbon atoms, up to 18 carbon atoms, or up to 12 carbon atoms. In addition to carbon atoms, additional heteroatoms, such as nitrogen, oxygen, or sulfur, can be present in the ring system.

In another aspect of this invention, $R^4$, $R^5$, $R^6$, and $R^7$ can be independently selected from the group consisting of H, halogen, alkyl, substituted alkyl, heteroalkyl, aryl, substituted aryl, heteroaryl, alkoxy, aryloxy, silyl, boryl, phosphino, amino, alkylthio, arylthio, hydrocarbyl, substituted hydrocarbyl, heteroatom-containing hydrocarbyl, a group having formula (IIa), and combinations thereof. In this aspect, $R^4$, $R^5$, $R^6$, and $R^7$ independently can have up to 48 carbon atoms, up to 36 carbon atoms, up to 24 carbon atoms, up to 18 carbon atoms, up to 12 carbon atoms, or up to 6 carbon atoms. Formula (IIa) is

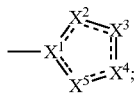

wherein:

$X^1$ is N, P, or —$C(R^A)_p$;

$X^2$, $X^3$, and $X^4$ are independently O, S, —$C(R^A)_q$—, —$N(R^A)_p$—, —$P(R^A)_p$—, —$N(R^B)$—, —$P(R^B)$—, or —$C(R^{13})(R^A)_q$—;

$X^5$ is O, S, or —$N(R^A)_p$—;

at least one, but no more than three, of $X^1$, $X^2$, $X^3$, and $X^4$ is C or —$C(R^A)_q$—, respectively;

each p is 0 or 1 and each q is 1 or 2;

each $R^A$ is independently H, halogen, nitro, alkyl, substituted alkyl, heteroalkyl, aryl, heteroaryl, alkoxy, aryloxy, silyl, boryl, phosphino, amino, alkylthio, arylthio, or combinations thereof;

each $R^B$ is aryl, substituted aryl, or heteroaryl; and optionally any combination of two or more of $R^4$, $R^5$, $R^6$, $R^7$, $R^A$ and/or $R^B$ are joined together to form one or more optionally substituted fused ring systems.

In yet another aspect of this invention, $R^4$, $R^5$, $R^6$, and $R^7$ are independently H, or a hydrocarbyl group, hydrocarbyloxide group, hydrocarbylamino group, hydrocarbylsilyl group, or halogenated hydrocarbyl group, any of which having up to 36 carbon atoms; alternatively, having up to 24 carbon atoms; or alternatively, having up to 18 carbon atoms. In some aspects, $R^4$, $R^5$, $R^6$, and $R^7$ are independently H or a hydrocarbyl or halogenated hydrocarbyl group having up to 18 carbon atoms, while in other aspects, $R^4$, $R^5$, $R^6$, and $R^7$ are independently H or an alkyl or aryl group having up to 18 carbon atoms. In yet another aspect, $R^4$, $R^5$, $R^6$, and $R^7$ independently can be methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, benzyl, tolyl, 2,6-dimethylphenyl, 2,6-diisopropylphenyl, 2,4,6-trimethylphenyl, trifluoromethyl, pentafluorophenyl, or 4-trifluoromethylphenyl, and the like.

It is contemplated that $R^4$, $R^5$, $R^6$, and $R^7$ are independently Me, t-Bu, Ph, CH$_2$-Ph, 2,4,6-trimethylphenyl, 2,6-dimethylphenyl, 2,6-diisopropylphenyl, trifluoromethyl, pentafluorophenyl, or 4-trifluoromethylphenyl in one aspect of this invention. In another aspect, $R^4$ is Ph, CH$_2$-Ph, 2,4,6-trimethylphenyl, 2,6-dimethylphenyl, or 2,6-diisopropylphenyl. Additionally or alternatively, $R^6$ can be Ph, CH$_2$-Ph, trimethylphenyl, 2,6-dimethylphenyl, or 2,6-diisopropylphenyl. Additionally or alternatively, $R^5$ can be Me, t-Bu, Ph, or CH$_2$-Ph. Additionally or alternatively, $R^7$ can be Me, t-Bu, Ph, or CH$_2$-Ph.

In accordance with another aspect of this invention, at least one of $R^4$, $R^5$, $R^6$, and $R^7$ contains up to 50 non-hydrogen atoms and has one of the following structures:

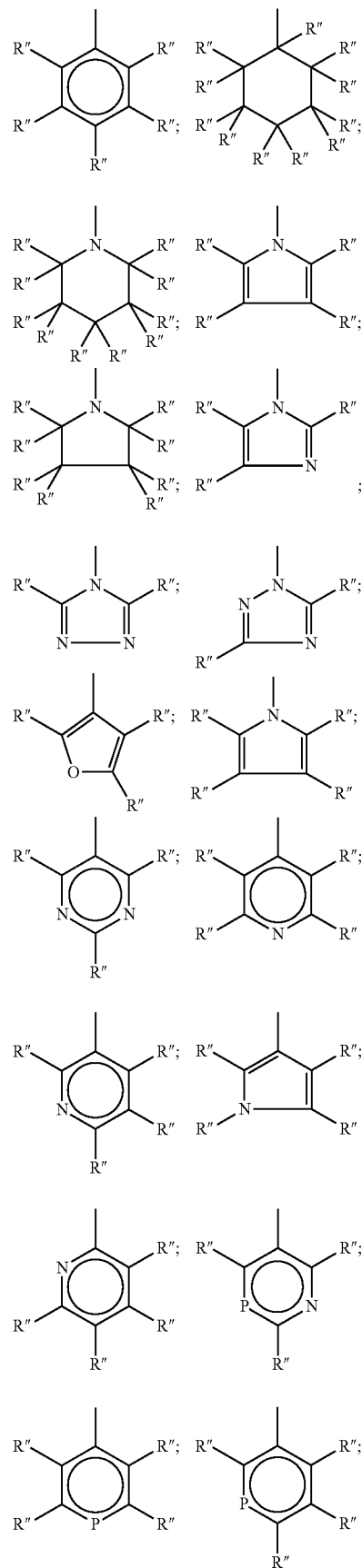

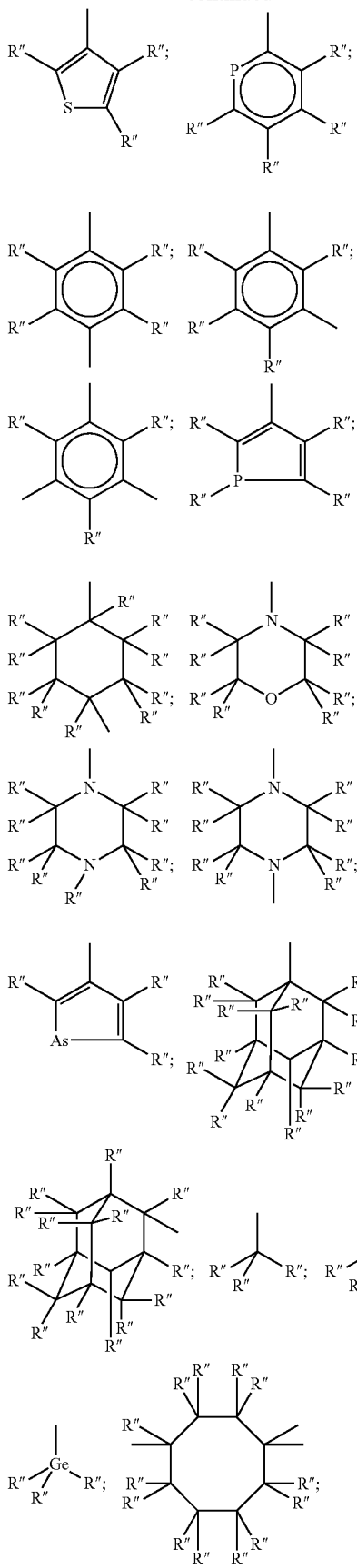
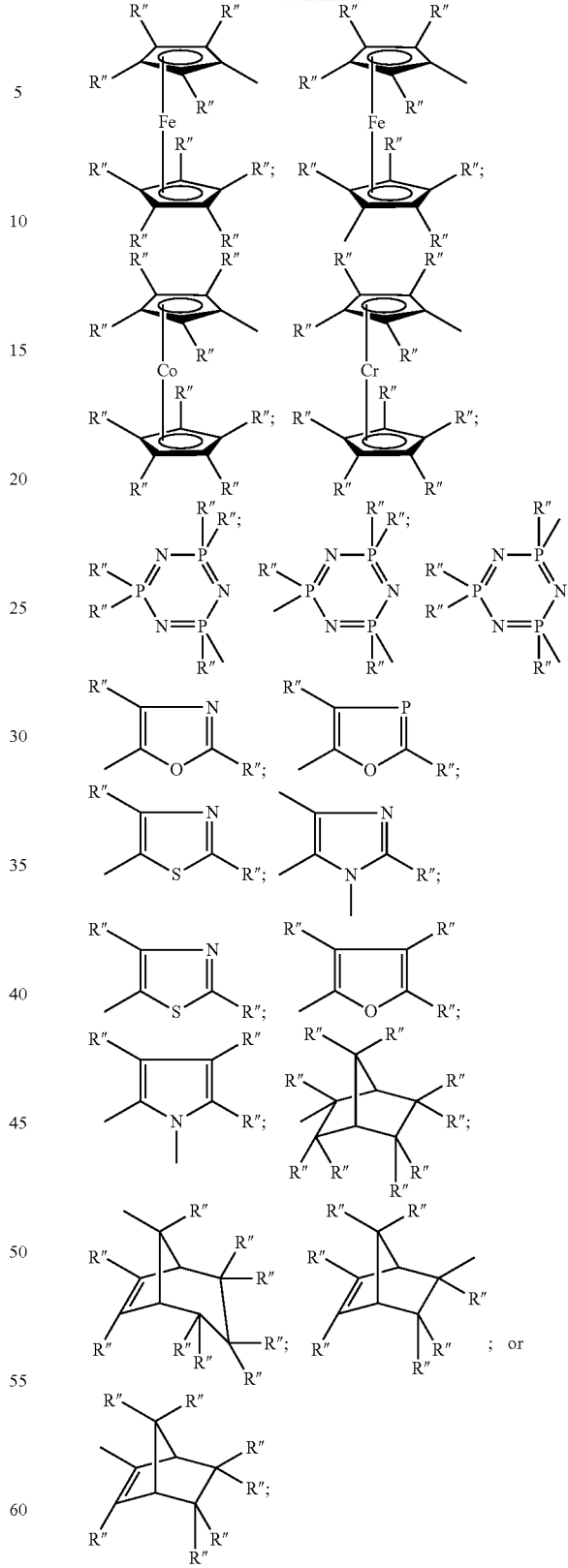
wherein each R″ is independently H, a halogen, a halogen-containing group, or an alkyl, aryl, cycloalkyl, or heterocyclic group. Generally, R″ has up to 18 carbon atoms, up to 12 carbon atoms, up to 8 carbon atoms, up to 6 carbon atoms, or up to 3 carbon atoms, in various aspects of this invention.

Each L in formula (II) is independently a ligand comprising atoms selected from the group consisting of H and Group 13 to 17 elements. Each L, therefore, can comprise atoms including, but not limited to, H, B, Al, C, Si, N, P, O, S, F, Cl, Br, I, and combinations thereof. According to one aspect of this invention, each L independently can contain up to 25 non-hydrogen atoms. In another aspect, each L independently can contain up to 18 non-hydrogen atoms or, alternatively, up to 12 non-hydrogen atoms. In yet another aspect, each L independently can contain up to 8 non-hydrogen atoms. These ligands may be covalently bonded to $M^B$, or ionically bonded to $M^B$.

Optionally, two or more L ligands can be connected to form a cyclic group, often having up to 36 carbon atoms, up to 24 carbon atoms, up to 18 carbon atoms, or up to 12 carbon atoms. Cyclic groups include cycloalkyl and cycloalkenyl moieties and such moieties can include, but are not limited to, cyclopentyl, cyclopentenyl, cyclohexyl, cyclohexenyl, and the like. Cyclic groups also include heterocyclic groups. Heteroatom-substituted cyclic groups can be formed with nitrogen, oxygen, or sulfur heteroatoms, for example. While these heterocyclic groups can have up to 12 or 18 or 24 or 36 carbons atoms, the heterocyclic groups can be 3-membered, 4-membered, 5-membered, 6-membered, or 7-membered groups in some aspects of this invention.

In one aspect, each L is independently F, Cl, Br, I, methyl, benzyl, phenyl, H, $BH_4$, $OBR_2$, or $SO_3R$, wherein R is an alkyl or aryl group, or a hydrocarbyloxide group, hydrocarbylamino group, hydrocarbylsilyl group, or halogenated hydrocarbyl group. The hydrocarbyloxide group, hydrocarbylamino group, hydrocarbylsilyl group, halogenated hydrocarbyl group, and R can have up to 18 carbon atoms; alternatively, up to 12 carbon atoms; or alternatively, up to 8 carbon atoms. In another aspect, each L independently can be F, Cl, Br, I, or a hydrocarbyl or halogenated hydrocarbyl group having up to 18 carbon atoms, for instance, up to 12 carbon atoms. In yet another aspect, each L independently can be F, Cl, Br, I, methyl, benzyl, or phenyl. In still another aspect, each L can be Cl.

In some aspects disclosed herein, each L independently can be H, halogen, alkyl, substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, or sulphate. In these and other aspects, each L independently can have up to 18 carbon atoms, or up to 12 carbon atoms, or up to 8 carbon atoms, or up to 6 carbon atoms.

In formula (II), n is 1, 2 or 3. According to one aspect of this invention, n is 1. In another aspect, n is 2. In yet another aspect, n is 3.

Bridged Imino Carbene Compounds

Bridged imino carbene compounds of the present invention can have the following structural formula:

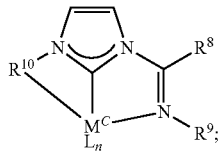
(III)

or a partially saturated or saturated version thereof;
wherein:
$M^C$ is a transition metal;
$R^8$, $R^9$ and $R^{10}$ are independently a substituent comprising atoms selected from the group consisting of H and Group 13 to 17 elements, and optionally two of $R^8$, $R^9$ and $R^{10}$ are connected to form a cyclic moiety;

each L is independently a ligand comprising atoms selected from the group consisting of H and Group 13 to 17 elements, and optionally two or more L ligands are connected to form a cyclic moiety; and n is 1, 2, or 3.

In formula (III), $M^C$ is a transition metal. For instance, $M^C$ can be a Group 3, 4, 5, or 6 transition metal, such as Sc, Y, Ti, Zr, Hf, V, Nb, Ta, Cr, and Mo, among others. In another aspect of this invention, $M^C$ is Ti, Zr, or Hf. In other aspects, $M^C$ is Ti, or $M^C$ is Zr, or $M^C$ is Hf.

$R^8$, $R^9$ and $R^{10}$ are independently a substituent comprising atoms selected from the group consisting of H and Group 13 to 17 elements, and optionally two of $R^8$, $R^9$ and $R^{10}$ are connected to form a cyclic moiety. Thus, $R^8$, $R^9$ and $R^{10}$ can comprise atoms including, but not limited to, H, B, Al, C, Si, N, P, O, S, F, Cl, Br, I, and combinations thereof. According to one aspect of this invention, $R^8$, $R^9$ and $R^{10}$ independently can contain up to 50 non-hydrogen atoms. According to another aspect, $R^8$, $R^9$ and $R^{10}$ independently can contain up to 25 non-hydrogen atoms; alternatively, up to 15 non-hydrogen atoms; or alternatively, up to 10 non-hydrogen atoms.

Optionally, two of $R^8$, $R^9$ and $R^{10}$ are connected to form a cyclic group, often having up to 36 carbon atoms, up to 24 carbon atoms, up to 18 carbon atoms, or up to 12 carbon atoms. In addition to carbon atoms, additional heteroatoms, such as nitrogen, oxygen, or sulfur, can be present in the ring system.

In another aspect of this invention, $R^8$ and $R^9$ can be independently selected from the group consisting of H, halogen, alkyl, substituted alkyl, heteroalkyl, aryl, substituted aryl, heteroaryl, alkoxy, aryloxy, silyl, boryl, phosphino, amino, alkylthio, arylthio, hydrocarbyl, substituted hydrocarbyl, heteroatom-containing hydrocarbyl, a group having formula (IIIa), and combinations thereof. In this aspect, $R^8$ and $R^9$ independently can have up to 48 carbon atoms, up to 36 carbon atoms, up to 24 carbon atoms, up to 18 carbon atoms, up to 12 carbon atoms, or up to 6 carbon atoms. Formula (IIIa) is

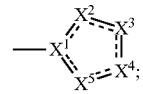

wherein:
$X^1$ is N, P, or —$C(R^A)_p$—;
$X^2$, $X^3$, and $X^4$ are independently O, S, —$C(R^A)_q$—, —$N(R^A)_p$—, —$P(R^A)_p$—, —$N(R^B)$—, —$P(R^B)$—, or —$C(R^B)(R^A)_q$—;
$X^5$ is O, S, or —$N(R^A)_p$—;
at least one, but no more than three, of $X^1$, $X^2$, $X^3$, and $X^4$ is C or —$C(R^A)_q$—, respectively;
each p is 0 or 1 and each q is 1 or 2;
each $R^A$ is independently H, halogen, nitro, alkyl, substituted alkyl, heteroalkyl, aryl, heteroaryl, alkoxy, aryloxy, silyl, boryl, phosphino, amino, alkylthio, arylthio, or combinations thereof;
each $R^B$ is aryl, substituted aryl, or heteroaryl; and
optionally any combination of two or more of $R^8$, $R^9$, $R^A$ and/or $R^B$ are joined together to form one or more optionally substituted fused ring systems.

In yet another aspect of this invention, $R^8$ and $R^9$ are independently H, or a hydrocarbyl group, hydrocarbyloxide group, hydrocarbylamino group, hydrocarbylsilyl group, or halogenated hydrocarbyl group, any of which having up to 36 carbon atoms; alternatively, having up to 24 carbon atoms; or alternatively, having up to 18 carbon atoms. In some aspects, $R^8$ and $R^9$ are independently H or a hydrocarbyl or halogenated hydrocarbyl group having up to 18 carbon atoms, while in other aspects, $R^8$ and $R^9$ are independently H or an alkyl or aryl group having up to 18 carbon atoms. In yet another aspect, $R^8$ and $R^9$ independently can be methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, benzyl, tolyl, 2,6-dimethylphenyl, 2,6-diisopropylphenyl, 2,4,6-trimethylphenyl, trifluoromethyl, pentafluorophenyl, or 4-trifluoromethylphenyl, and the like.

It is contemplated that $R^8$ and $R^9$ are independently Me, t-Bu, Ph, $CH_2$-Ph, 2,4,6-trimethylphenyl, 2,6-dimethylphenyl, 2,6-diisopropylphenyl, trifluoromethyl, pentafluorophenyl, or 4-trifluoromethylphenyl in one aspect of this invention. In another aspect, $R^8$ and $R^9$ independently can be Me, t-Bu, Ph, or $CH_2$-Ph. In these and other aspects, $R^{10}$ can be a heteroatom-containing hydrocarbyl group having up to 18 carbon atoms; alternatively, up to 12 carbon atoms; or alternatively, up to 8 carbon atoms. Further, $R^{10}$ can be a heteroaryl group or a saturated heterocyclic group having up to 12 carbon atoms in other aspects of this invention.

In accordance with another aspect, $R^{10}$ can be pyrrolidinyl, pyrrolinyl, furanyl, tetrahydrofuranyl, thiophenyl, imidazolyl, oxazolyl, thiazolyl, indolyl, pyridyl, pyrazinyl, isoxazolyl, pyrazolyl, pyrrolyl, isothiazolyl, oxadiazolyl, triazolyl, indolyl, carbazolyl, benzofuranyl, or benzothiophenyl, and the like. For instance, $R^{10}$ can be pyrrolidinyl or pyrrolinyl; alternatively, furanyl or tetrahydrofuranyl; alternatively, thiophenyl, imidazolyl, oxazolyl, thiazolyl, or indolyl; alternatively, pyridyl; alternatively, pyrazinyl; alternatively, isoxazolyl, pyrazolyl, pyrrolyl, or isothiazolyl; alternatively, oxadiazolyl, triazolyl, indolyl, carbazolyl; or alternatively, benzofuranyl or benzothiophenyl.

In accordance with another aspect of this invention, at least one of $R^8$, $R^9$, and $R^{10}$ contains up to 50 non-hydrogen atoms and has one of the following structures:

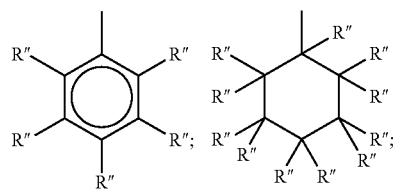

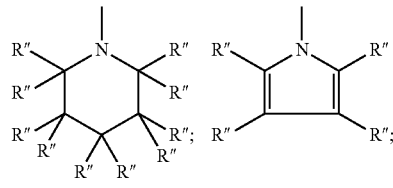

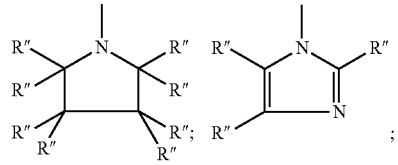

-continued

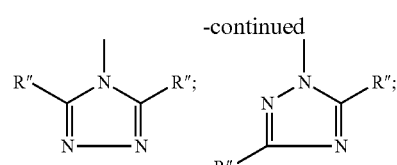

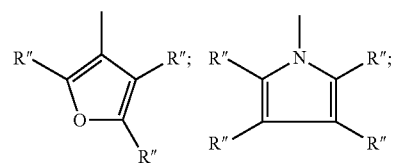

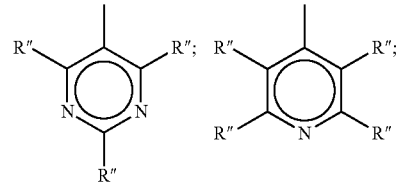

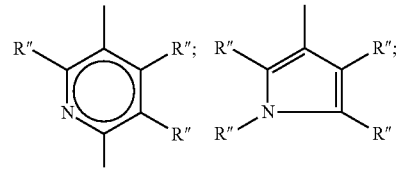

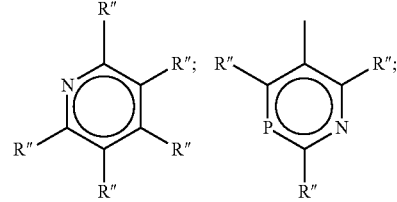

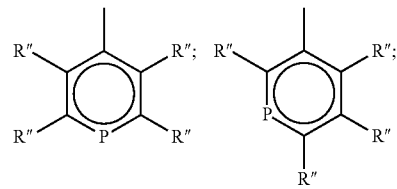

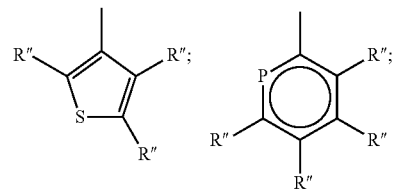

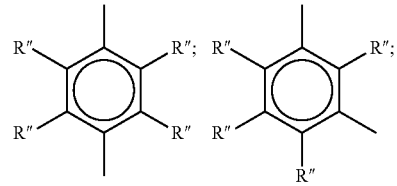

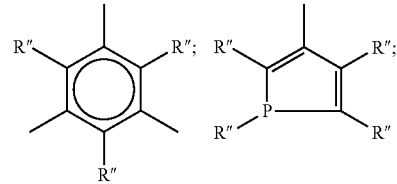

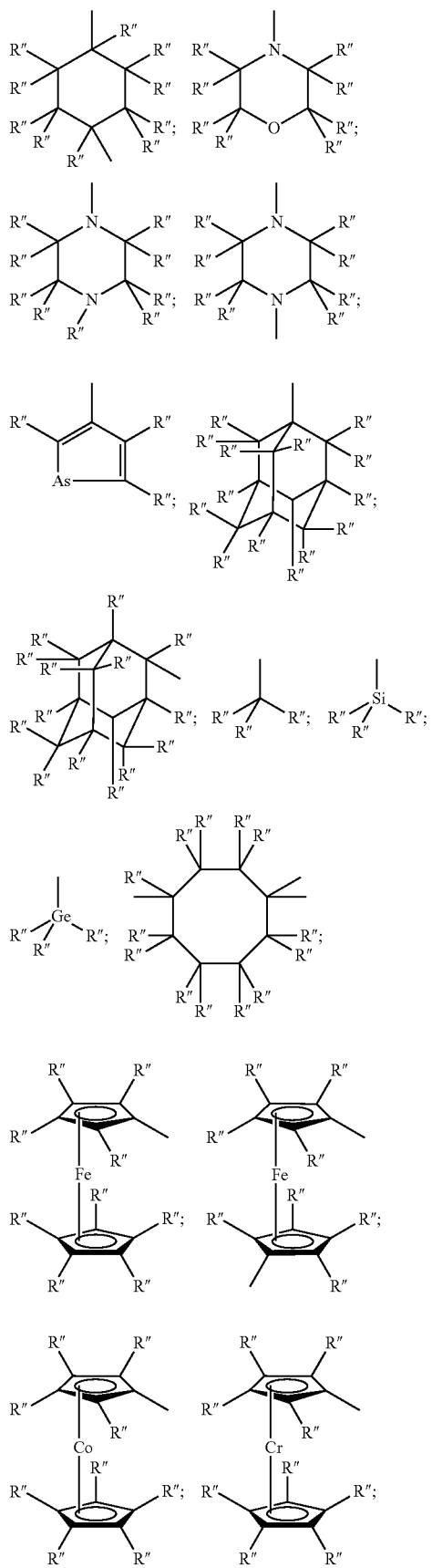
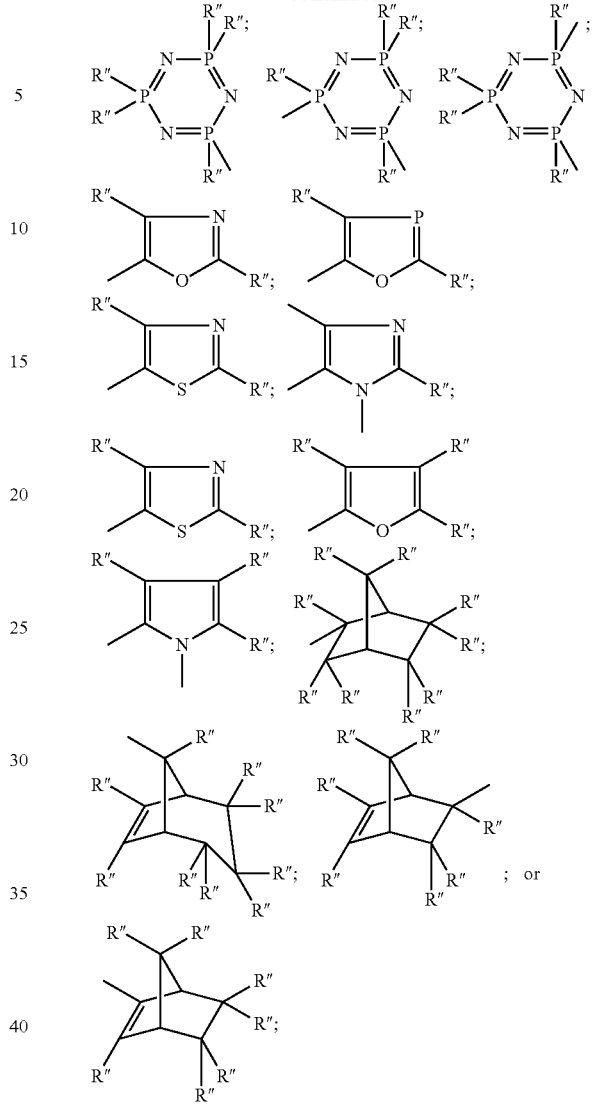

wherein each R″ is independently H, a halogen, a halogen-containing group, or an alkyl, aryl, cycloalkyl, or heterocyclic group. Generally, R″ has up to 18 carbon atoms, up to 12 carbon atoms, up to 8 carbon atoms, up to 6 carbon atoms, or up to 3 carbon atoms, in various aspects of this invention.

Each L in formula (III) is independently a ligand comprising atoms selected from the group consisting of H and Group 13 to 17 elements. Each L, therefore, can comprise atoms including, but not limited to, H, B, Al, C, Si, N, P, O, S, F, Cl, Br, I, and combinations thereof. According to one aspect of this invention, each L independently can contain up to 25 non-hydrogen atoms. In another aspect, each L independently can contain up to 18 non-hydrogen atoms or, alternatively, up to 12 non-hydrogen atoms. In yet another aspect, each L independently can contain up to 8 non-hydrogen atoms. These ligands may be covalently bonded to $M^C$, or ionically bonded to $M^C$.

Optionally, two or more L ligands can be connected to form a cyclic group, often having up to 36 carbon atoms, up to 24 carbon atoms, up to 18 carbon atoms, or up to 12 carbon atoms. Cyclic groups include cycloalkyl and cycloalkenyl moieties and such moieties can include, but are not limited to, cyclopentyl, cyclopentenyl, cyclohexyl, cyclohexenyl, and the like. Cyclic groups also include heterocyclic groups. Heteroatom-substituted cyclic groups can be formed with nitrogen, oxygen, or sulfur heteroatoms, for example. While these heterocyclic groups can have up to 12 or 18 or 24 or 36 carbons atoms, the heterocyclic groups can be 3-membered, 4-membered, 5-membered, 6-membered, or 7-membered groups in some aspects of this invention.

In one aspect, each L is independently F, Cl, Br, I, methyl, benzyl, phenyl, H, $BH_4$, $OBR_2$, or $SO_3R$, wherein R is an alkyl or aryl group, or a hydrocarbyloxide group, hydrocarbylamino group, hydrocarbylsilyl group, or halogenated hydrocarbyl group. The hydrocarbyloxide group, hydrocarbylamino group, hydrocarbylsilyl group, halogenated hydrocarbyl group, and R can have up to 18 carbon atoms; alternatively, up to 12 carbon atoms; or alternatively, up to 8 carbon atoms. In another aspect, each L independently can be F, Cl, Br, I, or a hydrocarbyl or halogenated hydrocarbyl group having up to 18 carbon atoms, for instance, up to 12 carbon atoms. In yet another aspect, each L independently can be F, Cl, Br, I, methyl, benzyl, or phenyl. In still another aspect, each L can be Cl.

In some aspects disclosed herein, each L independently can be H, halogen, alkyl, substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, or sulphate. In these and other aspects, each L independently can have up to 18 carbon atoms, or up to 12 carbon atoms, or up to 8 carbon atoms, or up to 6 carbon atoms.

In formula (III), n is 1, 2 or 3. According to one aspect of this invention, n is 1. In another aspect, n is 2. In yet another aspect, n is 3.

Dimer Compounds

Dimer compounds of the present invention can have the following structural formula:

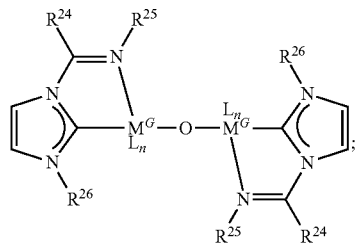

(VII)

or a partially saturated or saturated version thereof;
wherein:
each $M^G$ is independently a transition metal;
each $R^{24}$, $R^{25}$, and $R^{26}$ is independently a substituent comprising atoms selected from the group consisting of H and Group 13 to 17 elements, and optionally two of $R^{24}$, $R^{25}$, and $R^{26}$ are connected to form a cyclic moiety;
each L is independently a ligand comprising atoms selected from the group consisting of H and Group 13 to 17 elements, and optionally two or more L ligands are connected to form a cyclic moiety; and
each n is independently 1, 2, or 3.

In formula (VII), each $M^G$ is a transition metal. For instance, each $M^G$ can be a Group 3, 4, 5, or 6 transition metal, such as Sc, Y, Ti, Zr, Hf, V, Nb, Ta, Cr, and Mo, among others. In another aspect of this invention, each $M^G$ is Ti, Zr, or Hf. In other aspects, each $M^G$ is Ti, or each $M^G$ is Zr, or each $M^G$ is Hf.

Each $R^{24}$, $R^{25}$, and $R^{26}$ is independently a substituent comprising atoms selected from the group consisting of H and Group 13 to 17 elements, and optionally two of $R^{24}$, $R^{25}$, and $R^{26}$ are connected to form a cyclic moiety. Thus, $R^{24}$, $R^{25}$, and $R^{26}$ can comprise atoms including, but not limited to, H, B, Al, C, Si, N, P, O, S, F, Cl, Br, I, and combinations thereof. According to one aspect of this invention, each $R^{24}$, $R^{25}$, and $R^{26}$ independently can contain up to 50 non-hydrogen atoms. According to another aspect, each $R^{24}$, $R^{25}$, and $R^{26}$ independently can contain up to 25 non-hydrogen atoms; alternatively, up to 15 non-hydrogen atoms; or alternatively, up to 10 non-hydrogen atoms.

Optionally, two of $R^{24}$, $R^{25}$, and $R^{26}$ are connected to form a cyclic group, often having up to 36 carbon atoms, up to 24 carbon atoms, up to 18 carbon atoms, or up to 12 carbon atoms. In addition to carbon atoms, additional heteroatoms, such as nitrogen, oxygen, or sulfur, can be present in the ring system.

In another aspect of this invention, each $R^{24}$, $R^{25}$, and $R^{26}$ can be independently selected from the group consisting of H, halogen, alkyl, substituted alkyl, heteroalkyl, aryl, substituted aryl, heteroaryl, alkoxy, aryloxy, silyl, boryl, phosphino, amino, alkylthio, arylthio, hydrocarbyl, substituted hydrocarbyl, heteroatom-containing hydrocarbyl, a group having formula (VIIa), and combinations thereof. In this aspect, each $R^{24}$, $R^{25}$, and $R^{26}$ independently can have up to 48 carbon atoms, up to 36 carbon atoms, up to 24 carbon atoms, up to 18 carbon atoms, up to 12 carbon atoms, or up to 6 carbon atoms. Formula (VIIa) is

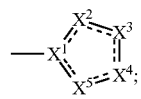

wherein:
$X^1$ is N, P, or —$C(R^A)_p$;
$X^2$, $X^3$, and $X^4$ are independently O, S, —$C(R^A)_q$—, —$N(R^A)_p$—, —$P(R^A)_p$—, —$N(R^B)$—, —$P(R^B)$—, or —$C(R^B)(R^A)_q$—;
$X^5$ is O, S, or —$N(R^A)_p$—;
at least one, but no more than three, of $X^1$, $X^2$, $X^3$, and $X^4$ is C or —$C(R^A)_q$—, respectively;
each p is 0 or 1 and each q is 1 or 2;
each $R^A$ is independently H, halogen, nitro, alkyl, substituted alkyl, heteroalkyl, aryl, heteroaryl, alkoxy, aryloxy, silyl, boryl, phosphino, amino, alkylthio, arylthio, or combinations thereof;
each $R^B$ is aryl, substituted aryl, or heteroaryl; and
optionally any combination of two or more of $R^{24}$, $R^{25}$, $R^{26}$, $R^A$ and/or $R^B$ are joined together to form one or more optionally substituted fused ring systems.

In yet another aspect of this invention, each $R^{24}$, $R^{25}$, and $R^{26}$ is independently H, or a hydrocarbyl group, hydrocarbyloxide group, hydrocarbylamino group, hydrocarbylsilyl group, or halogenated hydrocarbyl group, any of which having up to 36 carbon atoms; alternatively, having up to 24 carbon atoms; or alternatively, having up to 18 carbon atoms. In some aspects, each $R^{24}$, $R^{25}$, and $R^{26}$ is independently H or a hydrocarbyl or halogenated hydrocarbyl group having up to 18 carbon atoms, while in other aspects, each $R^{24}$, $R^{25}$, and $R^{26}$ is independently H or an alkyl or aryl group having up to 18 carbon atoms. In yet another aspect, each $R^{24}$, $R^{25}$, and $R^{26}$ independently can be methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, benzyl, tolyl, 2,6-dimethylphenyl, 2,6-diisopropylphenyl, 2,4,6-trimethylphenyl, trifluoromethyl, pentafluorophenyl, or 4-trifluoromethylphenyl, and the like.

It is contemplated that each $R^{24}$ and $R^{26}$ is independently Me, t-Bu, Ph, $CH_2$-Ph, 2,4,6-trimethylphenyl, 2,6-dimethylphenyl, 2,6-diisopropylphenyl, trifluoromethyl, pentafluorophenyl, or 4-trifluoromethylphenyl in one aspect of this invention. In another aspect, $R^{24}$ is Ph, $CH_2$-Ph, 2,4,6-trimethylphenyl, 2,6-dimethylphenyl, or 2,6-diisopropylphenyl. Additionally or alternatively, $R^{25}$ can be Ph, $CH_2$-Ph, 2,4,6-trimethylphenyl, 2,6-dimethylphenyl, or 2,6-diisopropylphenyl. Additionally or alternatively, $R^{26}$ can be Me, t-Bu, Ph, $CH_2$-Ph, 2,4,6-trimethylphenyl, 2,6-dimethylphenyl, or 2,6-diisopropylphenyl. In a further aspect, $R^{26}$ is Me, t-Bu, or Ph; alternatively, $R^{26}$ is Me; alternatively, $R^{26}$ is t-Bu; or alternatively, $R^{26}$ is Ph.

In accordance with another aspect of this invention, at least one of $R^{24}$, $R^{25}$, and $R^{26}$ contains up to 50 non-hydrogen atoms and has one of the following structures:

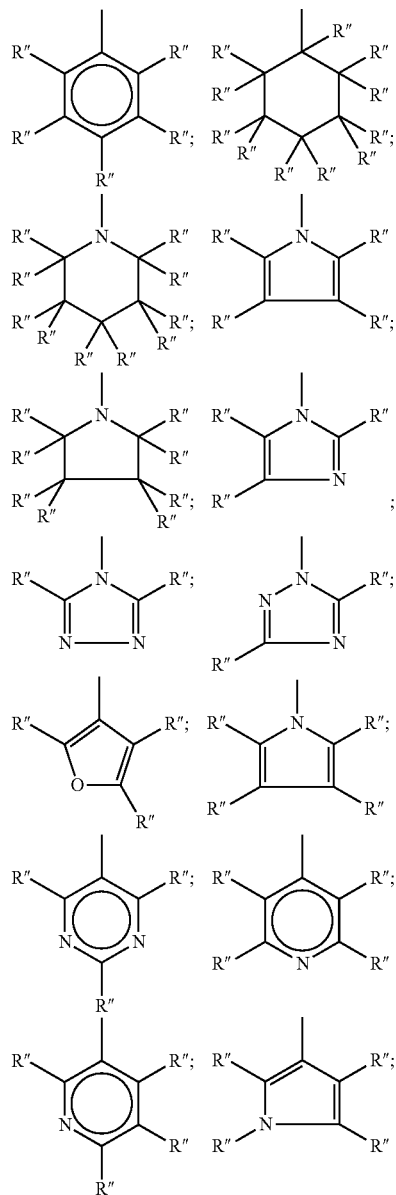

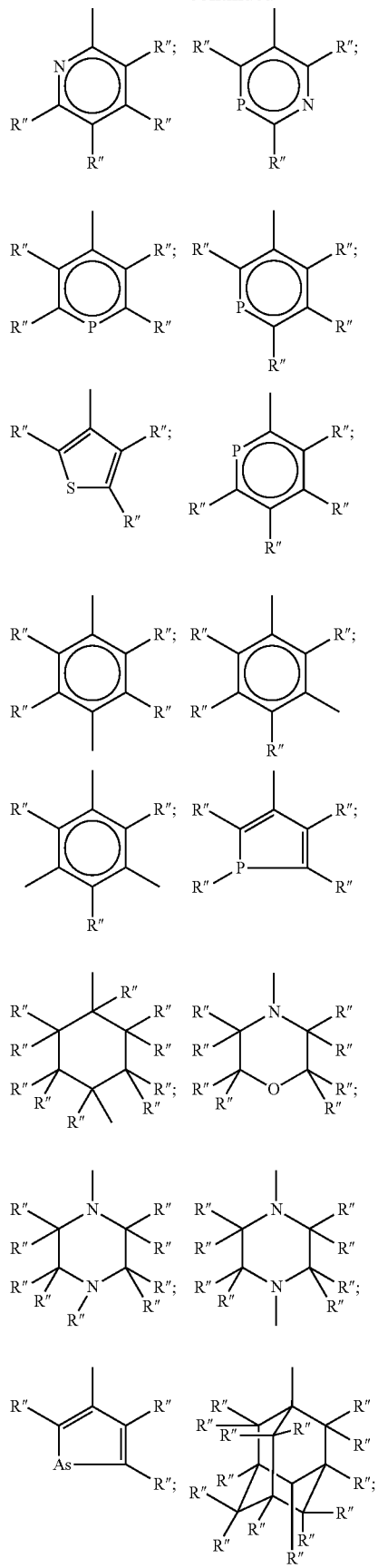

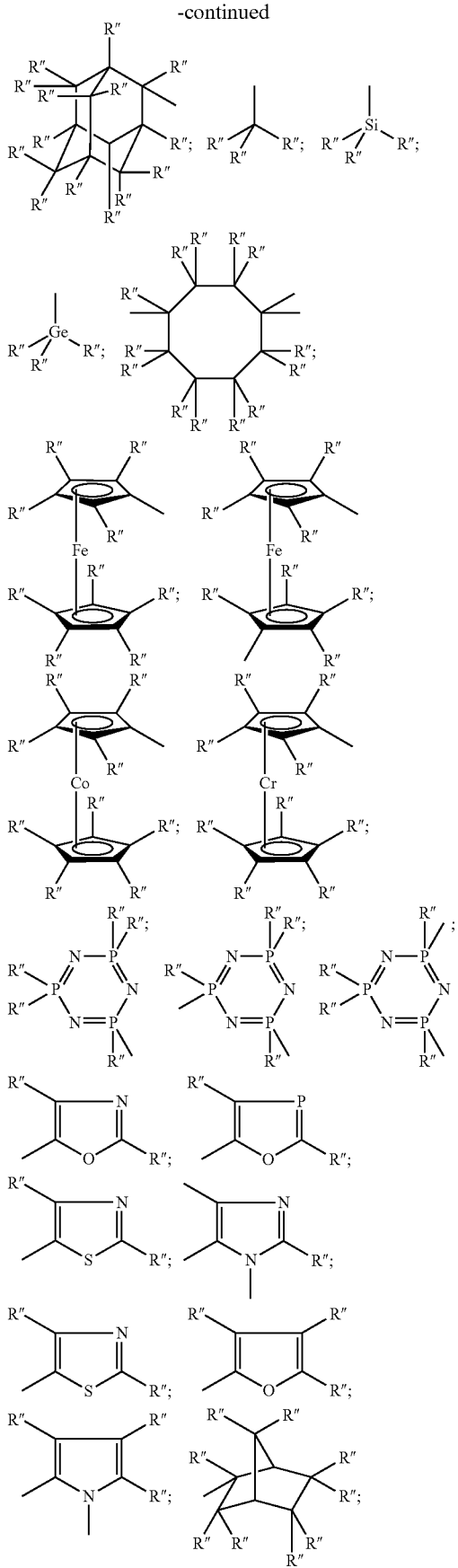

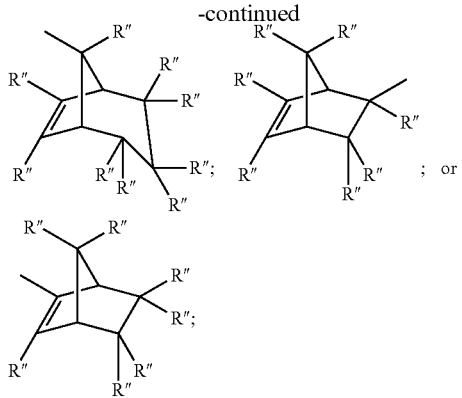

wherein each R" is independently H, a halogen, a halogen-containing group, or an alkyl, aryl, cycloalkyl, or heterocyclic group. Generally, R" has up to 18 carbon atoms, up to 12 carbon atoms, up to 8 carbon atoms, up to 6 carbon atoms, or up to 3 carbon atoms, in various aspects of this invention.

Each L in formula (VII) is independently a ligand comprising atoms selected from the group consisting of H and Group 13 to 17 elements. Each L, therefore, can comprise atoms including, but not limited to, H, B, Al, C, Si, N, P, O, S, F, Cl, Br, I, and combinations thereof. According to one aspect of this invention, each L independently can contain up to 25 non-hydrogen atoms. In another aspect, each L independently can contain up to 18 non-hydrogen atoms or, alternatively, up to 12 non-hydrogen atoms. In yet another aspect, each L independently can contain up to 8 non-hydrogen atoms. These ligands may be covalently bonded to $M^G$, or ionically bonded to $M^G$.

Optionally, two or more L ligands can be connected to form a cyclic group, often having up to 36 carbon atoms, up to 24 carbon atoms, up to 18 carbon atoms, or up to 12 carbon atoms. Cyclic groups include cycloalkyl and cycloalkenyl moieties and such moieties can include, but are not limited to, cyclopentyl, cyclopentenyl, cyclohexyl, cyclohexenyl, and the like. Cyclic groups also includes heterocyclic groups. Heteroatom-substituted cyclic groups can be formed with nitrogen, oxygen, or sulfur heteroatoms, for example. While these heterocyclic groups can have up to 12 or 18 or 24 or 36 carbons atoms, the heterocyclic groups can be 3-membered, 4-membered, 5-membered, 6-membered, or 7-membered groups in some aspects of this invention.

In one aspect, each L is independently F, Cl, Br, I, methyl, benzyl, phenyl, H, $BH_4$, $OBR_2$, or $SO_3R$, wherein R is an alkyl or aryl group, or a hydrocarbyloxide group, hydrocarbylamino group, hydrocarbylsilyl group, or halogenated hydrocarbyl group. The hydrocarbyloxide group, hydrocarbylamino group, hydrocarbylsilyl group, halogenated hydrocarbyl group, and R can have up to 18 carbon atoms; alternatively, up to 12 carbon atoms; or alternatively, up to 8 carbon atoms. In another aspect, each L independently can be F, Cl, Br, I, or a hydrocarbyl or halogenated hydrocarbyl group having up to 18 carbon atoms, for instance, up to 12 carbon atoms. In yet another aspect, each L independently can be F, Cl, Br, I, methyl, benzyl, or phenyl. In still another aspect, each L can be Cl.

In some aspects disclosed herein, each L independently can be H, halogen, alkyl, substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, or sulphate.

In these and other aspects, each L independently can have up to 18 carbon atoms, or up to 12 carbon atoms, or up to 8 carbon atoms, or up to 6 carbon atoms.

In formula (VII), each n is independently 1, 2 or 3. According to one aspect of this invention, each n is 1. In another aspect, each n is 2. In yet another aspect, each n is 3.

Bis-Carbene Compounds

Bis-carbene compounds of the present invention can have the following structural formula:

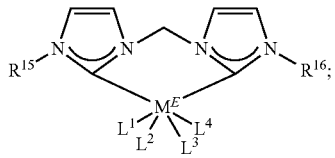

(V)

or a partially saturated or saturated version thereof;
wherein:
$M^E$ is Ti, Zr, or Hf;
$R^{15}$ and $R^{16}$ are independently a substituent comprising atoms selected from the group consisting of H and Group 13 to 17 elements, and optionally $R^{15}$ and $R^{16}$ are connected to form a cyclic moiety; and
$L^1$, $L^2$, $L^3$, and $L^4$ are independently a ligand comprising atoms selected from the group consisting of H and Group 13 to 17 elements, and optionally two or more of $L^1$, $L^2$, $L^3$, and $L^4$ ligands are connected to form a cyclic moiety.

In formula (V), $M^E$ is Ti, Zr, or Hf. In some aspects, $M^E$ is Ti; alternatively, $M^E$ is Zr; or alternatively, $M^E$ is Hf.

$R^{15}$ and $R^{16}$ are independently a substituent comprising atoms selected from the group consisting of H and Group 13 to 17 elements, and optionally $R^{15}$ and $R^{16}$ are connected to form a cyclic moiety. Thus, $R^{15}$ and $R^{16}$ can comprise atoms including, but not limited to, H, B, Al, C, Si, N, P, O, S, F, Cl, Br, I, and combinations thereof. According to one aspect of this invention, $R^{15}$ and $R^{16}$ independently can contain up to 50 non-hydrogen atoms. According to another aspect, $R^{15}$ and $R^{16}$ independently can contain up to 25 non-hydrogen atoms; alternatively, up to 15 non-hydrogen atoms; or alternatively, up to 10 non-hydrogen atoms.

Optionally, $R^{15}$ and $R^{16}$ are connected to form a cyclic group, often having up to 36 carbon atoms, up to 24 carbon atoms, up to 18 carbon atoms, or up to 12 carbon atoms. In addition to carbon atoms, additional heteroatoms, such as nitrogen, oxygen, or sulfur, can be present in the ring system.

In another aspect of this invention, $R^{15}$ and $R^{16}$ can be independently selected from the group consisting of H, halogen, alkyl, substituted alkyl, heteroalkyl, aryl, substituted aryl, heteroaryl, alkoxy, aryloxy, silyl, boryl, phosphino, amino, alkylthio, arylthio, hydrocarbyl, substituted hydrocarbyl, heteroatom-containing hydrocarbyl, a group having formula (Va), and combinations thereof. In this aspect, $R^{15}$ and $R^{16}$ independently can have up to 48 carbon atoms, up to 36 carbon atoms, up to 24 carbon atoms, up to 18 carbon atoms, up to 12 carbon atoms, or up to 6 carbon atoms. Formula (Va) is

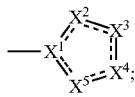

wherein:
$X^1$ is N, P, or —C($R^A$)$_p$—;
$X^2$, $X^3$, and $X^4$ are independently O, S, —C($R^A$)$_q$—, —N($R^A$)$_p$—, —P($R^A$)$_p$—, —N($R^B$)—, —P($R^B$)—, or —C($R^B$)($R^A$)$_q$—;
$X^5$ is O, S, or —N($R^A$)$_p$—;
at least one, but no more than three, of $X^1$, $X^2$, $X^3$, and $X^4$ is C or —C($R^A$)$_q$—, respectively;
each p is 0 or 1 and each q is 1 or 2;
each $R^A$ is independently H, halogen, nitro, alkyl, substituted alkyl, heteroalkyl, aryl, heteroaryl, alkoxy, aryloxy, silyl, boryl, phosphino, amino, alkylthio, arylthio, or combinations thereof;
each $R^B$ is aryl, substituted aryl, or heteroaryl; and
optionally any combination of two or more of $R^{15}$, $R^{16}$, $R^A$ and/or $R^B$ are joined together to form one or more optionally substituted fused ring systems.

In yet another aspect of this invention, $R^{15}$ and $R^{16}$ are independently H, or a hydrocarbyl group, hydrocarbyloxide group, hydrocarbylamino group, hydrocarbylsilyl group, or halogenated hydrocarbyl group, any of which having up to 36 carbon atoms; alternatively, having up to 24 carbon atoms; or alternatively, having up to 18 carbon atoms. In some aspects, $R^{15}$ and $R^{16}$ are independently H or a hydrocarbyl or halogenated hydrocarbyl group having up to 18 carbon atoms, while in other aspects, $R^{15}$ and $R^{16}$ are independently H or an alkyl or aryl group having up to 18 carbon atoms. In yet another aspect, $R^{15}$ and $R^{16}$ independently can be methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, benzyl, tolyl, 2,6-dimethylphenyl, 2,6-diisopropylphenyl, 2,4,6-trimethylphenyl, trifluoromethyl, pentafluorophenyl, or 4-trifluoromethyl-phenyl, and the like.

It is contemplated that $R^{15}$ and $R^{16}$ are independently Me, t-Bu, Ph, CH$_2$-Ph, 2,4,6-trimethylphenyl, 2,6-dimethylphenyl, 2,6-diisopropylphenyl, trifluoromethyl, pentafluorophenyl, or 4-trifluoromethylphenyl in one aspect of this invention. In another aspect, $R^{15}$ is Ph, CH$_2$-Ph, 2,4,6-trimethylphenyl, 2,6-dimethylphenyl, or 2,6-diisopropylphenyl. Alternatively, $R^{15}$ can be Me, t-Bu, or Ph. Additionally or alternatively, $R^{16}$ can be Ph, CH$_2$-Ph, 2,4,6-trimethylphenyl, 2,6-dimethylphenyl, or 2,6-diisopropylphenyl. Alternatively, $R^{16}$ can be Me, t-Bu, or Ph.

In accordance with another aspect of this invention, at least one of $R^{15}$ and $R^{16}$ contains up to 50 non-hydrogen atoms and has one of the following structures:

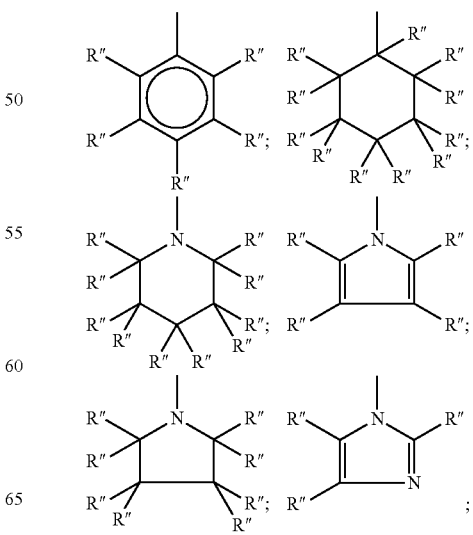

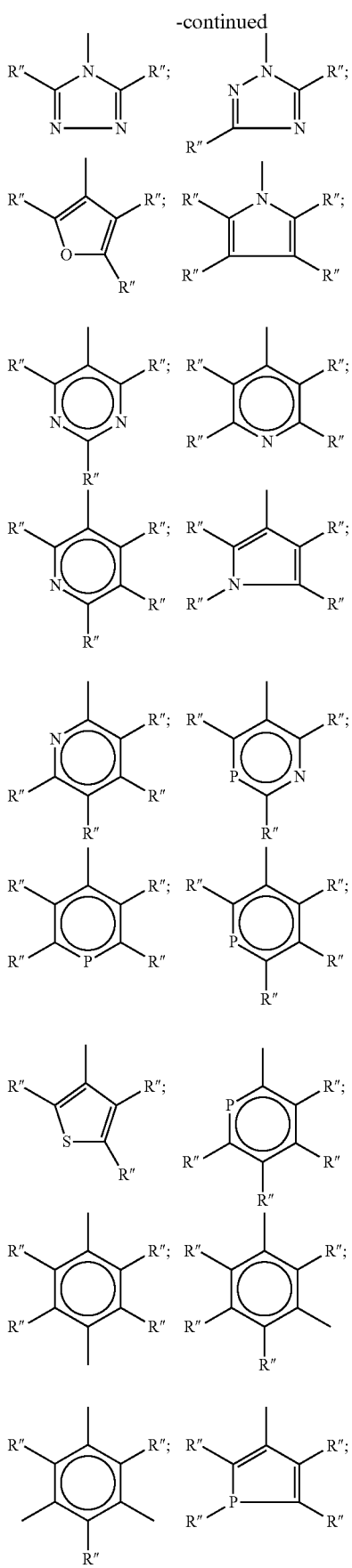
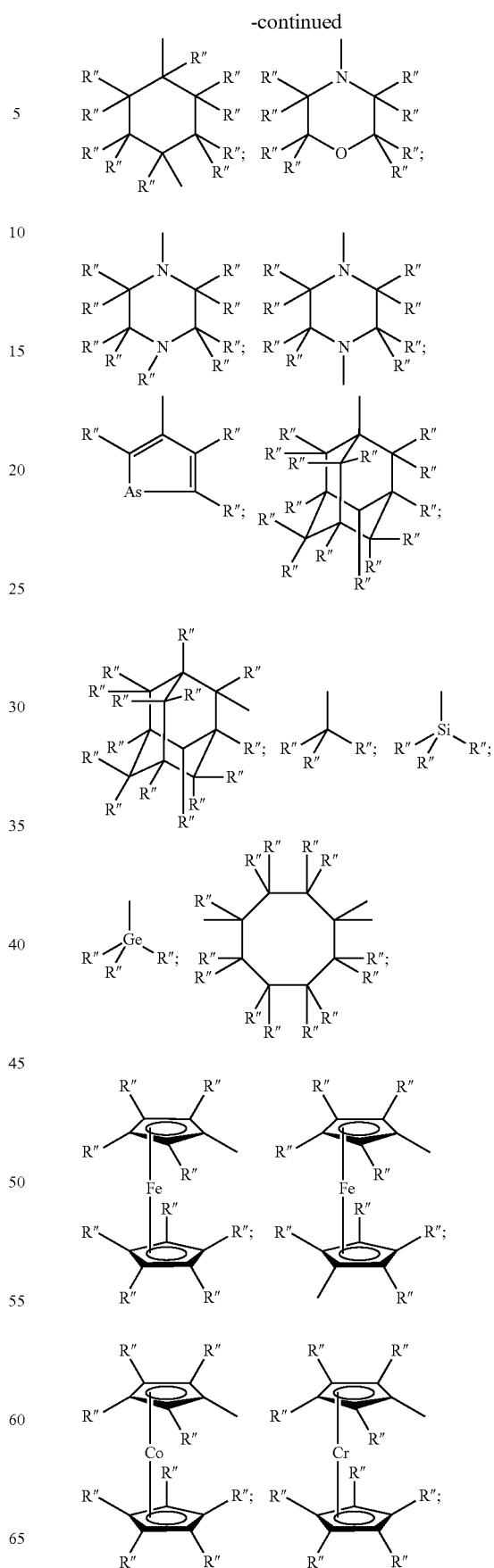

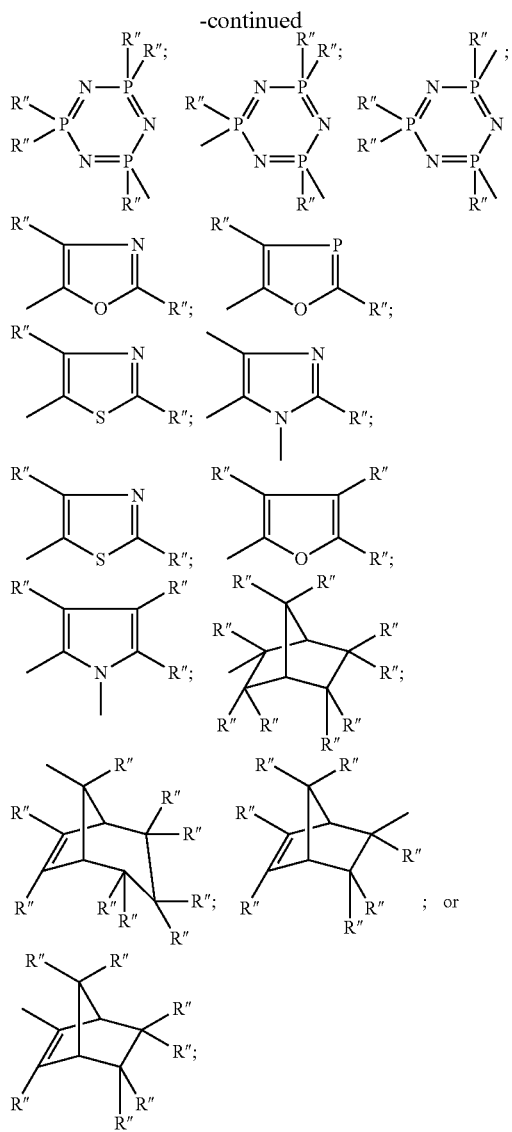

wherein each R″ is independently H, a halogen, a halogen-containing group, or an alkyl, aryl, cycloalkyl, or heterocyclic group. Generally, R″ has up to 18 carbon atoms, up to 12 carbon atoms, up to 8 carbon atoms, up to 6 carbon atoms, or up to 3 carbon atoms, in various aspects of this invention.

$L^1$, $L^2$, $L^3$, L and $L^4$ in formula (V) are independently a ligand comprising atoms selected from the group consisting of H and Group 13 to 17 elements. $L^1$, $L^2$, $L^3$, and $L^4$, therefore, can comprise atoms including, but not limited to, H, B, Al, C, Si, N, P, O, S, F, Cl, Br, I, and combinations thereof. According to one aspect of this invention, $L^1$, $L^2$, $L^3$, and $L^4$ independently can contain up to 25 non-hydrogen atoms. In another aspect, $L^1$, $L^2$, $L^3$, and $L^4$ independently can contain up to 18 non-hydrogen atoms or, alternatively, up to 12 non-hydrogen atoms. In yet another aspect, $L^1$, $L^2$, $L^3$, and $L^4$ independently can contain up to 8 non-hydrogen atoms. These ligands may be covalently bonded to $M^E$, or ionically bonded to $M^E$.

Optionally, two or more of $L^1$, $L^2$, $L^3$, and $L^4$ can be connected to form a cyclic group, often having up to 36 carbon atoms, up to 24 carbon atoms, up to 18 carbon atoms, or up to 12 carbon atoms. Cyclic groups include cycloalkyl and cycloalkenyl moieties and such moieties can include, but are not limited to, cyclopentyl, cyclopentenyl, cyclohexyl, cyclohexenyl, and the like. Cyclic groups also include heterocyclic groups. Heteroatom-substituted cyclic groups can be formed with nitrogen, oxygen, or sulfur heteroatoms, for example. While these heterocyclic groups can have up to 12 or 18 or 24 or 36 carbons atoms, the heterocyclic groups can be 3-membered, 4-membered, 5-membered, 6-membered, or 7-membered groups in some aspects of this invention.

In one aspect, $L^1$, $L^2$, $L^3$, and $L^4$ are independently F, Cl, Br, I, methyl, benzyl, phenyl, H, $BH_4$, $OBR_2$, or $SO_3R$, wherein R is an alkyl or aryl group, or a hydrocarbyloxide group, hydrocarbylamino group, hydrocarbylsilyl group, or halogenated hydrocarbyl group. The hydrocarbyloxide group, hydrocarbylamino group, hydrocarbylsilyl group, halogenated hydrocarbyl group, and R can have up to 18 carbon atoms; alternatively, up to 12 carbon atoms; or alternatively, up to 8 carbon atoms. In another aspect, $L^1$, $L^2$, $L^3$, and $L^4$ independently can be F, Cl, Br, I, or a hydrocarbyl or halogenated hydrocarbyl group having up to 18 carbon atoms, for instance, up to 12 carbon atoms. In yet another aspect, $L^1$, $L^2$, $L^3$, and $L^4$ independently can be F, Cl, Br, I, methyl, benzyl, or phenyl. In still another aspect, $L^1$, $L^2$, $L^3$, and $L^4$ can be Cl.

In some aspects disclosed herein, $L^1$, $L^2$, $L^3$, and $L^4$ independently can be H, halogen, alkyl, substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, or sulphate. In these and other aspects, $L^1$, $L^2$, $L^3$, and $L^4$ independently can have up to 18 carbon atoms, or up to 12 carbon atoms, or up to 8 carbon atoms, or up to 6 carbon atoms.

Imino-Enediamide Compounds

Imino-enediamide compounds of the present invention can have the following structural formula:

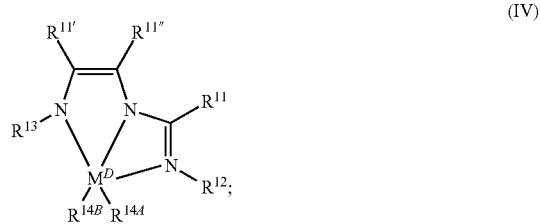

(IV)

or a partially saturated or saturated version thereof;
wherein:

$M^D$ is a transition metal;

$R^{11}$, $R^{11'}$, $R^{11''}$, $R^{12}$, and $R^{13}$ are independently a substituent comprising atoms selected from the group consisting of H and Group 13 to 17 elements, and optionally two of $R^{11}$, $R^{11'}$, $R^{11''}$, $R^{12}$, and $R^{13}$ are connected to form a cyclic moiety; and $R^{14A}$ and $R^{14B}$ are independently H, F, Cl, Br, I, or a hydrocarbyl, hydrocarbyloxide, hydrocarbylamino, hydrocarbylsilyl, or halogenated hydrocarbyl group, any of which having up to 48 carbon atoms.

In accordance with some aspects, the imino-enediamide compound can have formula (IV-A), or a partially saturated or saturated version thereof, while in accordance with other aspects, the imino-enediamide compound can have formula (IV-B), or a partially saturated or saturated version thereof:

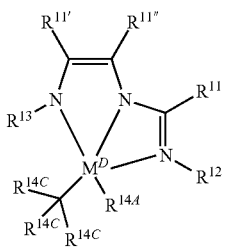

(IV-A)

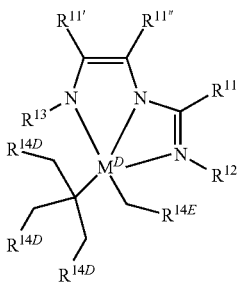

(IV-B)

In formula (IV), formula (IV-A), and formula (IV-B), $M^D$ is a transition metal. For instance, $M^D$ can be a Group 3, 4, 5, or 6 transition metal, such as Sc, Y, Ti, Zr, Hf, V, Nb, Ta, Cr, and Mo, among others. In another aspect of this invention, $M^D$ is Ti, Zr, or Hf. In other aspects, $M^D$ is Ti, or $M^D$ is Zr, or $M^D$ is Hf.

$R^{11}$, $R^{11'}$, $R^{11''}$, $R^{12}$, and $R^{13}$ are independently a substituent comprising atoms selected from the group consisting of H and Group 13 to 17 elements, and optionally two of $R^{11}$, $R^{11'}$, $R^{11''}$, $R^{12}$, and $R^{13}$ are connected to form a cyclic moiety. Thus, $R^{11}$, $R^{11'}$, $R^{11''}$, $R^{12}$, and $R^{13}$ can comprise atoms including, but not limited to, H, B, Al, C, Si, N, P, O, S, F, Cl, Br, I, and combinations thereof. According to one aspect of this invention, $R^{11}$, $R^{11'}$, $R^{11''}$, $R^{12}$, and $R^{13}$ independently can contain up to 50 non-hydrogen atoms. According to another aspect, $R^{11}$, $R^{11'}$, $R^{11''}$, $R^{12}$, and $R^{13}$ independently can contain up to 25 non-hydrogen atoms; alternatively, up to 15 non-hydrogen atoms; or alternatively, up to 10 non-hydrogen atoms.

Optionally, two of $R^{11}$, $R^{11'}$, $R^{11''}$, $R^{12}$, and $R^{13}$ are connected to form a cyclic group, often having up to 36 carbon atoms, up to 24 carbon atoms, up to 18 carbon atoms, or up to 12 carbon atoms. In addition to carbon atoms, additional heteroatoms, such as nitrogen, oxygen, or sulfur, can be present in the ring system.

In another aspect of this invention, $R^{11}$, $R^{11'}$, $R^{11''}$, $R^{12}$, and $R^{13}$ can be independently selected from the group consisting of H, halogen, alkyl, substituted alkyl, heteroalkyl, aryl, substituted aryl, heteroaryl, alkoxy, aryloxy, silyl, boryl, phosphino, amino, alkylthio, arylthio, hydrocarbyl, substituted hydrocarbyl, heteroatom-containing hydrocarbyl, a group having formula (IVa), and combinations thereof. In this aspect, $R^{11}$, $R^{11'}$, $R^{11''}$, $R^{12}$ and $R^{13}$ independently can have up to 48 carbon atoms, up to 36 carbon atoms, up to 24 carbon atoms, up to 18 carbon atoms, up to 12 carbon atoms, or up to 6 carbon atoms. Formula (IVa) is

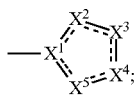

wherein:

$X^1$ is N, P, or —$C(R^A)_p$—;

$X^2$, $X^3$, and $X^4$ are independently O, S, —$C(R^A)_q$—, —$N(R^A)_p$—, —$P(R^A)_p$—, —$N(R^B)$—, —$P(R^B)$—, or —$C(R^B)(R^A)_q$—;

$X^5$ is O, S, or —$N(R^A)_p$—;

at least one, but no more than three, of $X^1$, $X^2$, $X^3$, and $X^4$ is C or —$C(R^A)_q$—, respectively;

each p is 0 or 1 and each q is 1 or 2;

each $R^A$ is independently H, halogen, nitro, alkyl, substituted alkyl, heteroalkyl, aryl, heteroaryl, alkoxy, aryloxy, silyl, boryl, phosphino, amino, alkylthio, arylthio, or combinations thereof;

each $R^B$ is aryl, substituted aryl, or heteroaryl; and optionally any combination of two or more of $R^{11}$, $R^{11'}$, $R^{11''}$, $R^{12}$, $R^{13}$, $R^A$ and/or $R^B$ are joined together to form one or more optionally substituted fused ring systems.

In yet another aspect of this invention, $R^{11}$, $R^{11'}$, $R^{11''}$, $R^{12}$, and $R^{13}$ are independently H, or a hydrocarbyl group, hydrocarbyloxide group, hydrocarbylamino group, hydrocarbylsilyl group, or halogenated hydrocarbyl group, any of which having up to 36 carbon atoms; alternatively, having up to 24 carbon atoms; or alternatively, having up to 18 carbon atoms. In some aspects, $R^{11}$, $R^{11'}$, $R^{11''}$, $R^{12}$, and $R^{13}$ are independently H or a hydrocarbyl or halogenated hydrocarbyl group having up to 18 carbon atoms, while in other aspects, $R^{11}$, $R^{11'}$, $R^{11''}$, $R^{12}$, and $R^{13}$ are independently H or an alkyl or aryl group having up to 18 carbon atoms. In yet another aspect, $R^{11}$, $R^{11'}$, $R^{11''}$, $R^{12}$, and $R^{13}$ independently can be H, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, benzyl, tolyl, 2,6-dimethylphenyl, 2,6-diisopropylphenyl, 2,4,6-trimethylphenyl, trifluoromethyl, pentafluorophenyl, or 4-trifluoromethylphenyl, and the like.

It is contemplated that $R^{11}$, $R^{11'}$, $R^{11''}$, $R^{12}$, and $R^{13}$ are independently H, Me, t-Bu, Ph, CH$_2$-Ph, 2,4,6-trimethylphenyl, 2,6-dimethylphenyl, 2,6-diisopropylphenyl, trifluoromethyl, pentafluorophenyl, 4-trifluoromethylphenyl, or trimethylsilyl, in one aspect of this invention. For instance, $R^{11'}$ and $R^{11''}$ can be H. In these and other aspects, $R^{11}$ can be Ph, CH$_2$-Ph, 2,4,6-trimethylphenyl, 2,6-dimethylphenyl, or 2,6-diisopropylphenyl. Additionally or alternatively, $R^{12}$ can be Ph, CH$_2$-Ph, 2,4,6-trimethylphenyl, 2,6-dimethylphenyl, or 2,6-diisopropylphenyl. Additionally or alternatively, $R^{13}$ can be Me, t-Bu, Ph, CH$_2$-Ph, 2,4,6-trimethylphenyl, 2,6-dimethylphenyl, or 2,6-diisopropylphenyl. In a further aspect, $R^{13}$ is Me, t-Bu, or Ph; alternatively, $R^{13}$ is Me; alternatively, $R^{13}$ is t-Bu; or alternatively, $R^{13}$ is Ph.

In accordance with another aspect of this invention, at least one of $R^{11}$, $R^{11'}$, $R^{11''}$, $R^{12}$, and $R^{13}$ contains up to 50 non-hydrogen atoms and has one of the following structures:

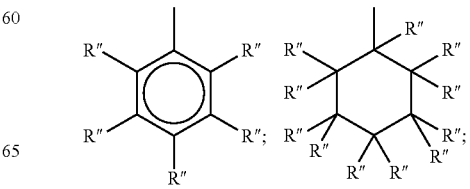

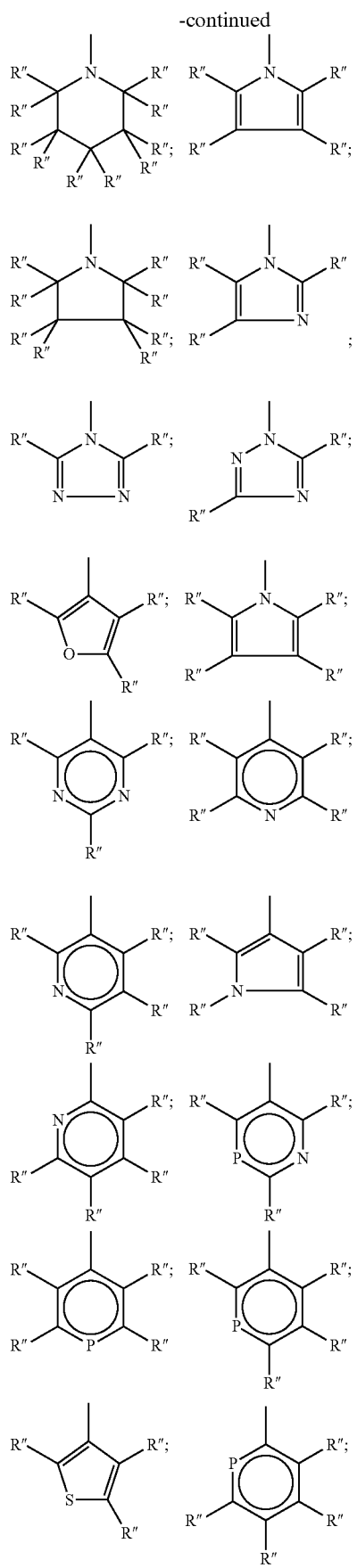
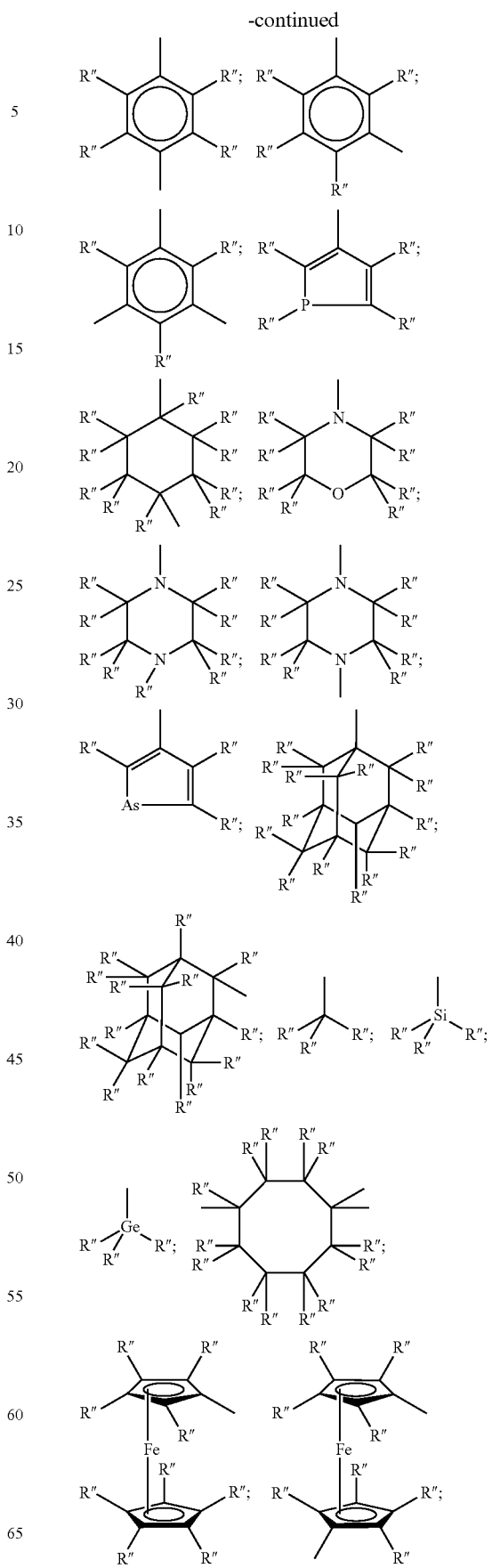

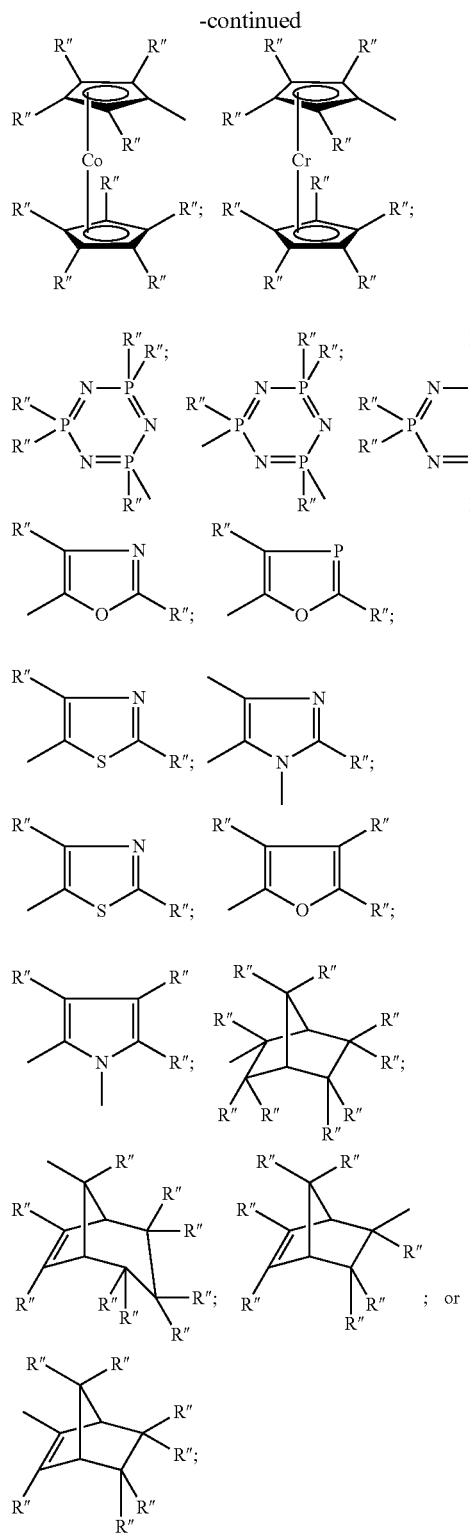

wherein each R″ is independently H, a halogen, a halogen-containing group, or an alkyl, aryl, cycloalkyl, or heterocyclic group. Generally, R″ has up to 18 carbon atoms, up to 12 carbon atoms, up to 8 carbon atoms, up to 6 carbon atoms, or up to 3 carbon atoms, in various aspects of this invention.

In another aspect, at least one of $R^{11}$, $R^{11'}$, $R^{11''}$, $R^{12}$, and $R^{13}$ has the following structure:

wherein:
$R^{108}$, $R^{109}$, $R^{110}$, and $R^{112}$ are independently H, F, Cl, Br, I, or a hydrocarbyl, hydrocarbyloxide, hydrocarbylamino, hydrocarbylsilyl, or halogenated hydrocarbyl group, any of which having up to 36 carbon atoms, up to 18 carbon atoms, up to 12 carbons atoms, or up to 6 carbon atoms. For instance, $R^{108}$, $R^{109}$, $R^{110}$, $R^{111}$, and $R^{112}$ independently can be H, Cl, methyl, ethyl, propyl, or butyl.

In formula (IV), $R^{14A}$ and $R^{14B}$ are independently H, F, Cl, Br, I, or a hydrocarbyl, hydrocarbyloxide, hydrocarbylamino, hydrocarbylsilyl, or halogenated hydrocarbyl group, any of which having up to 48 carbon atoms, up to 36 carbon atoms, up to 18 carbon atoms, up to 12 carbons atoms, or up to 8 carbon atoms. In one aspect, $R^{14A}$ and $R^{14B}$ are independently a hydrocarbyl or halogenated hydrocarbyl group having up to 48 carbon atoms; for instance, $R^{14A}$ and/or $R^{14B}$ independently can be methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, benzyl, tolyl, 2,6-dimethylphenyl, 2,6-diisopropylphenyl, 2,4,6-trimethylphenyl, trifluoromethyl, pentafluorophenyl, 4-trifluoromethylphenyl, —C(Ph)₃, or —C(CH₂-Ph)₃, and the like. In another aspect, $R^{14A}$ and $R^{14B}$ are independently a hydrocarbyloxide group having up to 48 carbon atoms, or up to 18 carbon atoms; alternatively, a hydrocarbylamino group having up to 48 carbon atoms, or up to 18 carbon atoms; or alternatively, a hydrocarbylsilyl group having up to 48 carbon atoms, or up to 18 carbon atoms. In yet another aspect, $R^{14A}$ and/or $R^{14B}$ can be H; alternatively, $R^{14A}$ and/or $R^{14B}$ independently can be F, Cl, Br, or I; alternatively, $R^{14A}$ and/or $R^{14B}$ can be trimethylsilyl; alternatively, $R^{14A}$ and/or $R^{14B}$ can be dimethylamino; alternatively, $R^{14A}$ and/or $R^{14B}$ can be Me; alternatively, $R^{14A}$ and/or $R^{14B}$ can be Ph; alternatively, $R^{14A}$ and/or $R^{14B}$ can be CH₂-Ph; alternatively, $R^{14A}$ and/or $R^{14B}$ can be —C(Ph)₃; or alternatively, $R^{14A}$ and/or $R^{14B}$ can be —C(CH₂-Ph)₃.

In some aspects, the imino-enediamide compound can have formula (IV-A), and $R^{14A}$ and $R^{14C}$ independently can be H, F, Cl, Br, I, or a hydrocarbyl, hydrocarbyloxide, hydrocarbylamino, hydrocarbylsilyl, or halogenated hydrocarbyl group, any of which having up to 15 carbon atoms, up to 12 carbon atoms, up to 10 carbon atoms, up to 8 carbons atoms, or up to 6 carbon atoms. In other aspects, $R^{14A}$ and $R^{14C}$ independently can be H, F, Cl, Br, I, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, benzyl, tolyl, 2,6-dimethylphenyl, 2,6-diisopropylphenyl, 2,4,6-trimethylphenyl, trifluoromethyl, pentafluorophenyl, or 4-trifluoromethylphenyl, and the like. In yet other aspects, $R^{14A}$ and/or $R^{14C}$ can be H; alternatively, $R^{14A}$ and/or $R^{14C}$ independently can be F, Cl, Br, or I; alternatively, $R^{14A}$ and/or $R^{14C}$ can be trimethylsilyl; alternatively, $R^{14A}$ and/or $R^{14C}$ can be dimethylamino; alternatively, $R^{14A}$ and/or $R^{14C}$ can be Me; alternatively, $R^{14A}$ and/or $R^{14C}$ can be Ph; or alternatively, $R^{14A}$ and/or $R^{14C}$ can be CH₂-Ph.

In accordance with certain aspects, the imino-enediamide compound can have formula (IV-B), and $R^{14D}$ and $R^{14E}$ independently can be H, F, Cl, Br, I, or a hydrocarbyl, hydrocarbyloxide, hydrocarbylamino, hydrocarbylsilyl, or halogenated hydrocarbyl group, any of which having up to 12 carbon atoms, up to 10 carbon atoms, up to 8 carbon atoms, or up to 6 carbon atoms. In another aspect, $R^{14D}$ and $R^{14E}$ independently can be H, F, Cl, Br, I, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, benzyl, tolyl, 2,6-dimethylphenyl, 2,6-diisopropylphenyl, 2,4,6-trimethylphenyl, trifluoromethyl, pentafluorophenyl, or 4-trifluoromethylphenyl, and the like. In yet another aspect, $R^{14D}$ and/or $R^{14E}$ can be H; alternatively, $R^{14D}$ and/or $R^{14E}$ independently can be F, Cl, Br, or I; alternatively, $R^{14D}$ and/or $R^{14E}$ can be trimethylsilyl; alternatively, $R^{14D}$ and/or $R^{14E}$ can be dimethylamino; alternatively, $R^{14D}$ and/or $R^{14E}$ can be Me; alternatively, $R^{14D}$ and/or $R^{14E}$ can be Ph; or alternatively, $R^{14D}$ and/or $R^{14E}$ can be $CH_2$-Ph.

Activator-Supports

The present invention encompasses various catalyst compositions containing an activator, which can be an activator-support. In one aspect, the activator-support comprises a chemically-treated solid oxide. Alternatively, the activator-support can comprise a clay mineral, a pillared clay, an exfoliated clay, an exfoliated clay gelled into another oxide matrix, a layered silicate mineral, a non-layered silicate mineral, a layered aluminosilicate mineral, a non-layered aluminosilicate mineral, or any combination thereof.

Generally, chemically-treated solid oxides exhibit enhanced acidity as compared to the corresponding untreated solid oxide compound. The chemically-treated solid oxide also functions as a catalyst activator as compared to the corresponding untreated solid oxide. While the chemically-treated solid oxide can activate the imino carbene compound/derivative in the absence of co-catalysts, it is not necessary to eliminate co-catalysts from the catalyst composition. The activation function of the activator-support is evident in the enhanced activity of catalyst composition as a whole, as compared to a catalyst composition containing the corresponding untreated solid oxide. However, it is believed that the chemically-treated solid oxide can function as an activator, even in the absence of an organoaluminum compound, aluminoxanes, organoboron or organoborate compounds, ionizing ionic compounds, and the like.

The chemically-treated solid oxide can comprise a solid oxide treated with an electron-withdrawing anion. While not intending to be bound by the following statement, it is believed that treatment of the solid oxide with an electron-withdrawing component augments or enhances the acidity of the oxide. Thus, either the activator-support exhibits Lewis or Brønsted acidity that is typically greater than the Lewis or Brønsted acid strength of the untreated solid oxide, or the activator-support has a greater number of acid sites than the untreated solid oxide, or both. One method to quantify the acidity of the chemically-treated and untreated solid oxide materials is by comparing the polymerization activities of the treated and untreated oxides under acid catalyzed reactions.

Chemically-treated solid oxides of this invention are formed generally from an inorganic solid oxide that exhibits Lewis acidic or Brønsted acidic behavior and has a relatively high porosity. The solid oxide is chemically-treated with an electron-withdrawing component, typically an electron-withdrawing anion, to form an activator-support.

According to one aspect of the present invention, the solid oxide used to prepare the chemically-treated solid oxide has a pore volume greater than about 0.1 cc/g. According to another aspect of the present invention, the solid oxide has a pore volume greater than about 0.5 cc/g. According to yet another aspect of the present invention, the solid oxide has a pore volume greater than about 1.0 cc/g.

In another aspect, the solid oxide has a surface area of from about 100 to about 1000 $m^2/g$. In yet another aspect, the solid oxide has a surface area of from about 200 to about 800 $m^2/g$. In still another aspect of the present invention, the solid oxide has a surface area of from about 250 to about 600 $m^2/g$.

The chemically-treated solid oxide can comprise a solid inorganic oxide comprising oxygen and one or more elements selected from Group 2, 3, 4, 5, 6, 7, 8, 9, 10, 11, 12, 13, 14, or 15 of the periodic table, or comprising oxygen and one or more elements selected from the lanthanide or actinide elements (See: Hawley's Condensed Chemical Dictionary, 11$^{th}$ Ed., John Wiley & Sons, 1995; Cotton, F. A., Wilkinson, G., Murillo, C. A., and Bochmann, M., Advanced Inorganic Chemistry, 6$^{th}$ Ed., Wiley-Interscience, 1999). For example, the inorganic oxide can comprise oxygen and an element, or elements, selected from Al, B, Be, Bi, Cd, Co, Cr, Cu, Fe, Ga, La, Mn, Mo, Ni, Sb, Si, Sn, Sr, Th, Ti, V, W, P, Y, Zn, and Zr.

Suitable examples of solid oxide materials or compounds that can be used to form the chemically-treated solid oxide include, but are not limited to, $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, and the like, including mixed oxides thereof, and combinations thereof. For example, the solid oxide can comprise silica, alumina, silica-alumina, silica-coated alumina, aluminum phosphate, aluminophosphate, heteropolytungstate, titania, zirconia, magnesia, boria, zinc oxide, mixed oxides thereof, or any combination thereof.

The solid oxide of this invention encompasses oxide materials such as alumina, "mixed oxide" compounds thereof such as silica-alumina, and combinations and mixtures thereof. The mixed oxide compounds such as silica-alumina can be single or multiple chemical phases with more than one metal combined with oxygen to form a solid oxide compound. Examples of mixed oxides that can be used in the activator-support of the present invention include, but are not limited to, silica-alumina, silica-titania, silica-zirconia, zeolites, various clay minerals, alumina-titania, alumina-zirconia, zinc-aluminate, alumina-boria, silica-boria, aluminophosphate-silica, titania-zirconia, and the like. The solid oxide of this invention also encompasses oxide materials such as silica-coated alumina, as described in U.S. Patent Publication No. 2010-0076167, the disclosure of which is incorporated herein by reference in its entirety.

The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect of the present invention, the electron-withdrawing component is an electron-withdrawing anion derived from a salt, an acid, or other compound, such as a volatile organic compound, that serves as a source or precursor for that anion. Examples of electron-withdrawing anions include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phosphotungstate, and the like, including mixtures and combinations thereof. In addition, other ionic or non-ionic compounds that serve as sources for these electron-withdrawing anions also can be employed in the present invention. It is contemplated that the electron-withdrawing anion can be, or can comprise, fluoride, chloride, bromide, phosphate, triflate, bisulfate, or sulfate, and the like, or any combination thereof, in some aspects of this invention. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, and the like, or any combination thereof.

Thus, for example, the activator-support (e.g., chemically-treated solid oxide) used in the catalyst compositions of the present invention can be, or can comprise, fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, or combinations thereof. In some aspects, the activator-support comprises fluorided alumina; alternatively, comprises chlorided alumina; alternatively, comprises sulfated alumina; alternatively, comprises fluorided silica-alumina; alternatively, comprises sulfated silica-alumina; alternatively, comprises fluorided silica-zirconia; alternatively, comprises chlorided silica-zirconia; or alternatively, comprises fluorided silica-coated alumina.

When the electron-withdrawing component comprises a salt of an electron-withdrawing anion, the counterion or cation of that salt can be selected from any cation that allows the salt to revert or decompose back to the acid during calcining. Factors that dictate the suitability of the particular salt to serve as a source for the electron-withdrawing anion include, but are not limited to, the solubility of the salt in the desired solvent, the lack of adverse reactivity of the cation, ion-pairing effects between the cation and anion, hygroscopic properties imparted to the salt by the cation, and the like, and thermal stability of the anion. Examples of suitable cations in the salt of the electron-withdrawing anion include, but are not limited to, ammonium, trialkyl ammonium, tetraalkyl ammonium, tetraalkyl phosphonium, $H^+$, $[H(OEt_2)_2]^+$, and the like.

Further, combinations of one or more different electron-withdrawing anions, in varying proportions, can be used to tailor the specific acidity of the activator-support to the desired level. Combinations of electron-withdrawing components can be contacted with the oxide material simultaneously or individually, and in any order that affords the desired chemically-treated solid oxide acidity. For example, one aspect of this invention is employing two or more electron-withdrawing anion source compounds in two or more separate contacting steps.

Thus, one example of such a process by which a chemically-treated solid oxide is prepared is as follows: a selected solid oxide, or combination of solid oxides, is contacted with a first electron-Withdrawing anion source compound to form a first mixture; this first mixture is calcined and then contacted with a second electron-withdrawing anion source compound to form a second mixture; the second mixture is then calcined to form a treated solid oxide. In such a process, the first and second electron-withdrawing anion source compounds can be either the same or different compounds.

According to another aspect of the present invention, the chemically-treated solid oxide comprises a solid inorganic oxide material, a mixed oxide material, or a combination of inorganic oxide materials, that is chemically-treated with an electron-withdrawing component, and optionally treated with a metal source, including metal salts, metal ions, or other metal-containing compounds. Non-limiting examples of the metal or metal ion include zinc, nickel, vanadium, titanium, silver, copper, gallium, tin, tungsten, molybdenum, zirconium, and the like, or combinations thereof. Examples of chemically-treated solid oxides that contain a metal or metal ion include, but are not limited to, chlorided zinc-impregnated alumina, fluorided titanium-impregnated alumina, fluorided zinc-impregnated alumina, chlorided zinc-impregnated silica-alumina, fluorided zinc-impregnated silica-alumina, sulfated zinc-impregnated alumina, chlorided zinc aluminate, fluorided zinc aluminate, sulfated zinc aluminate, silica-coated alumina treated with hexafluorotitanic acid, silica-coated alumina treated with zinc and then fluorided, and the like, or any combination thereof.

Any method of impregnating the solid oxide material with a metal can be used. The method by which the oxide is contacted with a metal source, typically a salt or metal-containing compound, can include, but is not limited to, gelling, co-gelling, impregnation of one compound onto another, and the like. If desired, the metal-containing compound is added to or impregnated into the solid oxide in solution form, and subsequently converted into the supported metal upon calcining. Accordingly, the solid inorganic oxide can further comprise a metal selected from zinc, titanium, nickel, vanadium, silver, copper, gallium, tin, tungsten, molybdenum, and the like, or combinations of these metals. For example, zinc is often used to impregnate the solid oxide because it can provide improved catalyst activity at a low cost.

The solid oxide can be treated with metal salts or metal-containing compounds before, after, or at the same time that the solid oxide is treated with the electron-withdrawing anion. Following any contacting method, the contacted mixture of solid compound, electron-withdrawing anion, and the metal ion is typically calcined. Alternatively, a solid oxide material, an electron-withdrawing anion source, and the metal salt or metal-containing compound are contacted and calcined simultaneously.

Various processes are used to form the chemically-treated solid oxide useful in the present invention. The chemically-treated solid oxide can comprise the contact product of one or more solid oxides with one or more electron-withdrawing anion sources. It is not required that the solid oxide be calcined prior to contacting the electron-withdrawing anion source. The contact product typically is calcined either during or after the solid oxide is contacted with the electron-withdrawing anion source. The solid oxide can be calcined or uncalcined. Various processes to prepare solid oxide activator-supports that can be employed in this invention have been reported. For example, such methods are described in U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, and 6,750,302, the disclosures of which are incorporated herein by reference in their entirety.

According to one aspect of the present invention, the solid oxide material is chemically-treated by contacting it with an electron-withdrawing component, typically an electron-withdrawing anion source. Further, the solid oxide material optionally is chemically treated with a metal ion, and then calcined to form a metal-containing or metal-impregnated chemically-treated solid oxide. According to another aspect of the present invention, the solid oxide material and electron-withdrawing anion source are contacted and calcined simultaneously.

The method by which the oxide is contacted with the electron-withdrawing component, typically a salt or an acid of an electron-withdrawing anion, can include, but is not limited to, gelling, co-gelling, impregnation of one compound onto another, and the like. Thus, following any contacting method, the contacted mixture of the solid oxide, electron-withdrawing anion, and optional metal ion, is calcined.

The solid oxide activator-support (i.e., chemically-treated solid oxide) thus can be produced by a process comprising:

1) contacting a solid oxide (or solid oxides) with an electron-withdrawing anion source compound (or compounds) to form a first mixture; and 2) calcining the first mixture to form the solid oxide activator-support.

According to another aspect of the present invention, the solid oxide activator-support (chemically-treated solid oxide) is produced by a process comprising:

1) contacting a solid oxide (or solid oxides) with a first electron-withdrawing anion source compound to form a first mixture;

2) calcining the first mixture to produce a calcined first mixture;

3) contacting the calcined first mixture with a second electron-withdrawing anion source compound to form a second mixture; and 4) calcining the second mixture to form the solid oxide activator-support.

According to yet another aspect of the present invention, the chemically-treated solid oxide is produced or formed by contacting the solid oxide with the electron-withdrawing anion source compound, where the solid oxide compound is calcined before, during, or after contacting the electron-withdrawing anion source, and where there is a substantial absence of aluminoxanes, organoboron or organoborate compounds, and ionizing ionic compounds.

Calcining of the treated solid oxide generally is conducted in an ambient atmosphere, typically in a dry ambient atmosphere, at a temperature from about 200° C. to about 900° C., and for a time of about 1 minute to about 100 hours. Calcining can be conducted at a temperature of from about 300° C. to about 800° C., or alternatively, at a temperature of from about 400° C. to about 700° C. Calcining can be conducted for about 30 minutes to about 50 hours, or for about 1 hour to about 15 hours. Thus, for example, calcining can be carried out for about 1 to about 10 hours at a temperature of from about 350° C. to about 550° C. Any suitable ambient atmosphere can be employed during calcining. Generally, calcining is conducted in an oxidizing atmosphere, such as air. Alternatively, an inert atmosphere, such as nitrogen or argon, or a reducing atmosphere, such as hydrogen or carbon monoxide, can be used.

According to one aspect of the present invention, the solid oxide material is treated with a source of halide ion, sulfate ion, or a combination of anions, optionally treated with a metal ion, and then calcined to provide the chemically-treated solid oxide in the form of a particulate solid. For example, the solid oxide material can be treated with a source of sulfate (termed a "sulfating agent"), a source of chloride ion (termed a "chloriding agent"), a source of fluoride ion (termed a "fluoriding agent"), or a combination thereof, and calcined to provide the solid oxide activator. Useful acidic activator-supports include, but are not limited to, bromided alumina, chlorided alumina, fluorided alumina, sulfated alumina, bromided silica-alumina, chlorided silica-alumina, fluorided silica-alumina, sulfated silica-alumina, bromided silica-zirconia, chlorided silica-zirconia, fluorided silica-zirconia, sulfated silica-zirconia, fluorided silica-titania, alumina treated with hexafluorotitanic acid, silica-coated alumina treated with hexafluorotitanic acid, silica-alumina treated with hexafluorozirconic acid, silica-alumina treated with trifluoroacetic acid, fluorided boria-alumina, silica treated with tetrafluoroboric acid, alumina treated with tetrafluoroboric acid, alumina treated with hexafluorophosphoric acid, a pillared clay, such as a pillared montmorillonite, optionally treated with fluoride, chloride, or sulfate; phosphated alumina or other aluminophosphates optionally treated with sulfate, fluoride, or chloride; or any combination of the above. Further, any of these activator-supports optionally can be treated with a metal ion.

The chemically-treated solid oxide can comprise a fluorided solid oxide in the form of a particulate solid. The fluorided solid oxide can be formed by contacting a solid oxide with a fluoriding agent. The fluoride ion can be added to the oxide by forming a slurry of the oxide in a suitable solvent such as alcohol or water including, but not limited to, the one to three carbon alcohols because of their volatility and low surface tension. Examples of suitable fluoriding agents include, but are not limited to, hydrofluoric acid (HF), ammonium fluoride ($NH_4F$), ammonium bifluoride ($NH_4HF_2$), ammonium tetrafluoroborate ($NH_4BF_4$), ammonium silicofluoride (hexafluorosilicate) (($NH_4$)$_2SiF_6$), ammonium hexafluorophosphate ($NH_4 PF_6$), hexafluorotitanic acid ($H_2TiF_6$), ammonium hexafluorotitanic acid (($NH_4$)$_2TiF_6$), hexafluorozirconic acid ($H_2ZrF_6$), $AlF_3$, $NH_4AlF_4$, analogs thereof, and combinations thereof. Triflic acid and ammonium triflate also can be employed. For example, ammonium bifluoride ($NH_4HF_2$) can be used as the fluoriding agent, due to its ease of use and availability.

If desired, the solid oxide is treated with a fluoriding agent during the calcining step. Any fluoriding agent capable of thoroughly contacting the solid oxide during the calcining step can be used. For example, in addition to those fluoriding agents described previously, volatile organic fluoriding agents can be used. Examples of volatile organic fluoriding agents useful in this aspect of the invention include, but are not limited to, freons, perfluorohexane, perfluorobenzene, fluoromethane, trifluoroethanol, and the like, and combinations thereof. Calcining temperatures generally must be high enough to decompose the compound and release fluoride. Gaseous hydrogen fluoride (HF) or fluorine ($F_2$) itself also can be used with the solid oxide if fluorided while calcining. Silicon tetrafluoride ($SiF_4$) and compounds containing tetrafluoroborate ($BF_4^-$) also can be employed. One convenient method of contacting the solid oxide with the fluoriding agent is to vaporize a fluoriding agent into a gas stream used to fluidize the solid oxide during calcination.

Similarly, in another aspect of this invention, the chemically-treated solid oxide comprises a chlorided solid oxide in the form of a particulate solid. The chlorided solid oxide is formed by contacting a solid oxide with a chloriding agent. The chloride ion can be added to the oxide by forming a slurry of the oxide in a suitable solvent. The solid oxide can be treated with a chloriding agent during the calcining step. Any chloriding agent capable of serving as a source of chloride and thoroughly contacting the oxide during the calcining step can be used, such as $SiCl_4$, $SiMe_2Cl_2$, $TiCl_4$, $BCl_3$, and the like, including mixtures thereof. Volatile organic chloriding agents can be used. Examples of suitable volatile organic chloriding agents include, but are not limited to, certain freons, perchlorobenzene, chloromethane, dichloromethane, chloroform, carbon tetrachloride, trichloroethanol, and the like, or any combination thereof. Gaseous hydrogen chloride or chlorine itself also can be used with the solid oxide during calcining. One convenient method of contacting the oxide with the chloriding agent is to vaporize a chloriding agent into a gas stream used to fluidize the solid oxide during calcination.

The amount of fluoride or chloride ion present before calcining the solid oxide generally is from about 1 to about 50% by weight, where the weight percent is based on the weight of the solid oxide, for example, silica-alumina, before calcining. According to another aspect of this invention, the amount of fluoride or chloride ion present before calcining the solid oxide is from about 1 to about 25% by weight, and according to another aspect of this invention, from about 2 to about 20% by weight. According to yet another aspect of this invention, the amount of fluoride or chloride ion present before calcining the solid oxide is from about 4 to about 10% by weight. Once impregnated with halide, the halided oxide can be dried by any suitable method including, but not limited to, suction filtration followed by evaporation, drying under vacuum, spray drying, and the like, although it is also possible to initiate the calcining step immediately without drying the impregnated solid oxide.

The silica-alumina used to prepare the treated silica-alumina typically has a pore volume greater than about 0.5 cc/g. According to one aspect of the present invention, the pore volume is greater than about 0.8 cc/g, and according to another aspect of the present invention, greater than about 1.0 cc/g. Further, the silica-alumina generally has a surface area greater than about 100 m$^2$/g. According to another aspect of this invention, the surface area is greater than about 250 m$^2$/g. In yet another aspect, the surface area is greater than about 350 m$^2$/g.

The silica-alumina utilized in the present invention typically has an alumina content from about 5 to about 95% by weight. According to one aspect of this invention, the alumina content of the silica-alumina is from about 5 to about 50%, or from about 8% to about 30%, alumina by weight. In another aspect, high alumina content silica-alumina compounds can employed, in which the alumina content of these silica-alumina compounds typically ranges from about 60% to about 90%, or from about 65% to about 80%, alumina by weight. According to yet another aspect of this invention, the solid oxide component comprises alumina without silica, and according to another aspect of this invention, the solid oxide component comprises silica without alumina.

The sulfated solid oxide comprises sulfate and a solid oxide component, such as alumina or silica-alumina, in the form of a particulate solid. Optionally, the sulfated oxide is treated further with a metal ion such that the calcined sulfated oxide comprises a metal. According to one aspect of the present invention, the sulfated solid oxide comprises sulfate and alumina. In some instances, the sulfated alumina is formed by a process wherein the alumina is treated with a sulfate source, for example, sulfuric acid or a sulfate salt such as ammonium sulfate. This process is generally performed by forming a slurry of the alumina in a suitable solvent, such as alcohol or water, in which the desired concentration of the sulfating agent has been added. Suitable organic solvents include, but are not limited to, the one to three carbon alcohols because of their volatility and low surface tension.

According to one aspect of this invention, the amount of sulfate ion present before calcining is from about 0.5 to about 100 parts by weight sulfate ion to about 100 parts by weight solid oxide. According to another aspect of this invention, the amount of sulfate ion present before calcining is from about 1 to about 50 parts by weight sulfate ion to about 100 parts by weight solid oxide, and according to still another aspect of this invention, from about 5 to about 30 parts by weight sulfate ion to about 100 parts by weight solid oxide. These weight ratios are based on the weight of the solid oxide before calcining. Once impregnated with sulfate, the sulfated oxide can be dried by any suitable method including, but not limited to, suction filtration followed by evaporation, drying under vacuum, spray drying, and the like, although it is also possible to initiate the calcining step immediately.

According to another aspect of the present invention, the activator-support used in preparing the catalyst compositions of this invention comprises an ion-exchangeable activator-support, including but not limited to silicate and aluminosilicate compounds or minerals, either with layered or non-layered structures, and combinations thereof. In another aspect of this invention, ion-exchangeable, layered aluminosilicates such as pillared clays are used as activator-supports. When the acidic activator-support comprises an ion-exchangeable activator-support, it can optionally be treated with at least one electron-withdrawing anion such as those disclosed herein, though typically the ion-exchangeable activator-support is not treated with an electron-withdrawing anion.

According to another aspect of the present invention, the activator-support of this invention comprises clay minerals having exchangeable cations and layers capable of expanding. Typical clay mineral activator-supports include, but are not limited to, ion-exchangeable, layered aluminosilicates such as pillared clays. Although the term "support" is used, it is not meant to be construed as an inert component of the catalyst composition, but rather is to be considered an active part of the catalyst composition, because of its intimate association with the imino carbene compound/derivative component.

According to another aspect of the present invention, the clay materials of this invention encompass materials either in their natural state or that have been treated with various ions by wetting, ion exchange, or pillaring. Typically, the clay material activator-support of this invention comprises clays that have been ion exchanged with large cations, including polynuclear, highly charged metal complex cations. However, the clay material activator-supports of this invention also encompass clays that have been ion exchanged with simple salts, including, but not limited to, salts of Al(III), Fe(II), Fe(III), and Zn(II) with ligands such as halide, acetate, sulfate, nitrate, or nitrite.

According to another aspect of the present invention, the activator-support comprises a pillared clay. The term "pillared clay" is used to refer to clay materials that have been ion exchanged with large, typically polynuclear, highly charged metal complex cations. Examples of such ions include, but are not limited to, Keggin ions which can have charges such as 7+, various polyoxometallates, and other large ions. Thus, the term pillaring refers to a simple exchange reaction in which the exchangeable cations of a clay material are replaced with large, highly charged ions, such as Keggin ions. These polymeric cations are then immobilized within the interlayers of the clay and when calcined are converted to metal oxide "pillars," effectively supporting the clay layers as column-like structures. Thus, once the clay is dried and calcined to produce the supporting pillars between clay layers, the expanded lattice structure is maintained and the porosity is enhanced. The resulting pores can vary in shape and size as a function of the pillaring material and the parent clay material used. Examples of pillaring and pillared clays are found in: T. J. Pinnavaia, *Science* 220 (4595), 365-371 (1983); J. M. Thomas, Intercalation Chemistry, (S. Whittington and A. Jacobson, eds.) Ch. 3, pp. 55-99, Academic Press, Inc., (1972); U.S. Pat. Nos. 4,452,910; 5,376,611; and 4,060,480; the disclosures of which are incorporated herein by reference in their entirety.

The pillaring process utilizes clay minerals having exchangeable cations and layers capable of expanding. Any pillared clay that can enhance the polymerization of olefins in the catalyst composition of the present invention can be used. Therefore, suitable clay minerals for pillaring include, but are not limited to, allophanes; smectites, both dioctahedral (Al) and tri-octahedral (Mg) and derivatives thereof such as montmorillonites (bentonites), nontronites, hectorites, or laponites; halloysites; vermiculites; micas; fluoromicas; chlorites;

mixed-layer clays; the fibrous clays including but not limited to sepiolites, attapulgites, and palygorskites; a serpentine clay; illite; laponite; saponite; and any combination thereof. In one aspect, the pillared clay activator-support comprises bentonite or montmorillonite. The principal component of bentonite is montmorillonite.

The pillared clay can be pretreated if desired. For example, a pillared bentonite is pretreated by drying at about 300° C. under an inert atmosphere, typically dry nitrogen, for about 3 hours, before being added to the polymerization reactor. Although an exemplary pretreatment is described herein, it should be understood that the preheating can be carried out at many other temperatures and times, including any combination of temperature and time steps, all of which are encompassed by this invention.

The activator-support used to prepare the catalyst compositions of the present invention can be combined with other inorganic support materials, including, but not limited to, zeolites, inorganic oxides, phosphated inorganic oxides, and the like. In one aspect, typical support materials that are used include, but are not limited to, silica, silica-alumina, alumina, titania, zirconia, magnesia, boria, thoria, aluminophosphate, aluminum phosphate, silica-titania, coprecipitated silica/titania, mixtures thereof, or any combination thereof.

According to another aspect of the present invention, one or more of the imino carbene compounds/derivatives can be precontacted with an olefin monomer and an organoaluminum compound for a first period of time prior to contacting this mixture with the activator-support. Once the precontacted mixture of the imino carbene compound/derivative, olefin monomer, and organoaluminum compound is contacted with the activator-support, the composition further comprising the activator-support is termed a "postcontacted" mixture. The postcontacted mixture can be allowed to remain in further contact for a second period of time prior to being charged into the reactor in which the polymerization process will be carried out.

According to yet another aspect of the present invention, one or more of the imino carbene compounds/derivatives can be precontacted with an olefin monomer and an activator-support for a first period of time prior to contacting this mixture with the organoaluminum compound. Once the precontacted mixture of the imino carbene compound/derivative, olefin monomer, and activator-support is contacted with the organoaluminum compound, the composition further comprising the organoaluminum is termed a "postcontacted" mixture. The postcontacted mixture can be allowed to remain in further contact for a second period of time prior to being introduced into the polymerization reactor.

Organoaluminum Compounds

In some aspects, catalyst compositions of the present invention can comprise one or more organoaluminum compounds. Such compounds can include, but are not limited to, compounds having the formula:

$$(R^C)_3Al;$$

where $R^C$ is an aliphatic group having from 1 to 10 carbon atoms. For example, $R^C$ can be methyl, ethyl, propyl, butyl, hexyl, or isobutyl.

Other organoaluminum compounds which can be used in catalyst compositions disclosed herein can include, but are not limited to, compounds having the formula:

$$Al(X^A)_m(X^B)_{3-m},$$

where $X^A$ is a hydrocarbyl; $X^B$ is an alkoxide or an aryloxide, a halide, or a hydride; and m is from 1 to 3, inclusive. Hydrocarbyl is used herein to specify a hydrocarbon radical group and includes, but is not limited to, aryl, alkyl, cycloalkyl, alkenyl, cycloalkenyl, cycloalkadienyl, alkynyl, aralkyl, aralkenyl, aralkynyl, and the like, and includes all substituted, unsubstituted, branched, linear, and/or heteroatom substituted derivatives thereof.

In one aspect, $X^A$ is a hydrocarbyl having from 1 to about 18 carbon atoms. In another aspect of the present invention, $X^A$ is an alkyl having from 1 to 10 carbon atoms. For example, $X^A$ can be methyl, ethyl, propyl, n-butyl, sec-butyl, isobutyl, or hexyl, and the like, in yet another aspect of the present invention.

According to one aspect of the present invention, $X^B$ is an alkoxide or an aryloxide, any one of which has from 1 to 18 carbon atoms, a halide, or a hydride. In another aspect of the present invention, $X^B$ is selected independently from fluorine and chlorine. In yet another aspect, $X^B$ is chlorine.

In the formula, $Al(X^A)_m(X^B)_{3-m}$, m is a number from 1 to 3, inclusive, and typically, m is 3. The value of m is not restricted to be an integer; therefore, this formula includes sesquihalide compounds or other organoaluminum cluster compounds.

Examples of organoaluminum compounds suitable for use in accordance with the present invention include, but are not limited to, trialkylaluminum compounds, dialkylaluminum halide compounds, dialkylaluminum alkoxide compounds, dialkylaluminum hydride compounds, and combinations thereof. Specific non-limiting examples of suitable organoaluminum compounds include trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum, diisobutylaluminum hydride, diethylaluminum ethoxide, diethylaluminum chloride, and the like, or combinations thereof.

The present invention contemplates a method of precontacting a imino carbene compound/derivative with an organoaluminum compound and an olefin monomer to form a precontacted mixture, prior to contacting this precontacted mixture with an activator-support to form a catalyst composition. When the catalyst composition is prepared in this manner, typically, though not necessarily, a portion of the organoaluminum compound is added to the precontacted mixture and another portion of the organoaluminum compound is added to the postcontacted mixture prepared when the precontacted mixture is contacted with the solid oxide activator-support. However, the entire organoaluminum compound can be used to prepare the catalyst composition in either the precontacting or postcontacting step. Alternatively, all the catalyst components are contacted in a single step.

Further, more than one organoaluminum compound can be used in either the precontacting or the postcontacting step. When an organoaluminum compound is added in multiple steps, the amounts of organoaluminum compound disclosed herein include the total amount of organoaluminum compound used in both the precontacted and postcontacted mixtures, and any additional organoaluminum compound added to the polymerization reactor. Therefore, total amounts of organoaluminum compounds are disclosed regardless of whether a single organoaluminum compound or more than one organoaluminum compound is used.

Aluminoxane Compounds

The present invention further provides a catalyst composition which can comprise an aluminoxane compound. As used herein, the term "aluminoxane" refers to aluminoxane compounds, compositions, mixtures, or discrete species, regardless of how such aluminoxanes are prepared, formed or otherwise provided. For example, a catalyst composition comprising an aluminoxane compound can be prepared in which aluminoxane is provided as the poly(hydrocarbyl aluminum oxide), or in which aluminoxane is provided as the combination of an aluminum alkyl compound and a source of active protons such as water. Aluminoxanes are also referred to as poly(hydrocarbyl aluminum oxides) or organoaluminoxanes.

The other catalyst components typically are contacted with the aluminoxane in a saturated hydrocarbon compound solvent, though any solvent that is substantially inert to the reactants, intermediates, and products of the activation step can be used. The catalyst composition formed in this manner is collected by any suitable method, for example, by filtration. Alternatively, the catalyst composition is introduced into the polymerization reactor without being isolated.

The aluminoxane compound of this invention can be an oligomeric aluminum compound comprising linear structures, cyclic structures, or cage structures, or mixtures of all three. Cyclic aluminoxane compounds having the formula:

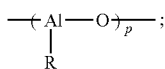

wherein R in this formula is a linear or branched alkyl having from 1 to 10 carbon atoms, and p is an integer from 3 to 20, are encompassed by this invention. The AlRO moiety shown here also constitutes the repeating unit in a linear aluminoxane. Thus, linear aluminoxanes having the formula:

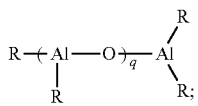

wherein R in this formula is a linear or branched alkyl having from 1 to 10 carbon atoms, and q is an integer from 1 to 50, are also encompassed by this invention.

Further, aluminoxanes can have cage structures of the formula $R_{5r+\alpha}^{1}R_{r-\alpha}^{b}Al_{4r}O_{3r}$, wherein $R^t$ is a terminal linear or branched alkyl group having from 1 to 10 carbon atoms; $R_b$ is a bridging linear or branched alkyl group having from 1 to 10 carbon atoms; r is 3 or 4; and $\alpha$ is equal to $n_{Al(3)}-n_{O(2)}+n_{O(4)}$, wherein $n_{Al(3)}$ is the number of three coordinate aluminum atoms, $n_{O(2)}$ is the number of two coordinate oxygen atoms, and $n_{O(4)}$ is the number of 4 coordinate oxygen atoms.

Thus, aluminoxanes which can be employed in the catalyst compositions of the present invention are represented generally by formulas such as $(R-Al-O)_p$, $R(R-Al-O)_qAlR_2$, and the like. In these formulas, the R group is typically a linear or branched $C_1$-$C_6$ alkyl, such as methyl, ethyl, propyl, butyl, pentyl, or hexyl. Examples of aluminoxane compounds that can be used in accordance with the present invention include, but are not limited to, methylaluminoxane, ethylaluminoxane, n-propylaluminoxane, iso-propylaluminoxane, n-butylaluminoxane, t-butylaluminoxane, sec-butylaluminoxane, iso-butylaluminoxane, 1-pentylaluminoxane, 2-pentylaluminoxane, 3-pentylaluminoxane, isopentylaluminoxane, neopentylaluminoxane, and the like, or any combination thereof. Methylaluminoxane, ethylaluminoxane, and iso-butylaluminoxane are prepared from trimethylaluminum, triethylaluminum, or triisobutylaluminum, respectively, and sometimes are referred to as poly(methyl aluminum oxide), poly(ethyl aluminum oxide), and poly(isobutyl aluminum oxide), respectively. It is also within the scope of the invention to use an aluminoxane in combination with a trialkylaluminum, such as that disclosed in U.S. Pat. No. 4,794,096, incorporated herein by reference in its entirety.

The present invention contemplates many values of p and q in the aluminoxane formulas $(R-Al-O)_p$ and $R(R-Al-O)_qAlR_2$, respectively. In some aspects, p and q are at least 3. However, depending upon how the organoaluminoxane is prepared, stored, and used, the value of p and q can vary within a single sample of aluminoxane, and such combinations of organoaluminoxanes are contemplated herein.

In preparing a catalyst composition containing an aluminoxane, the molar ratio of the total moles of aluminum in the aluminoxane (or aluminoxanes) to the total moles of imino carbene compound(s)/derivative(s) in the composition is generally between about 1:10 and about 100,000:1. In another aspect, the molar ratio is in a range from about 5:1 to about 15,000:1. Optionally, aluminoxane can be added to a polymerization zone in ranges from about 0.01 mg/L to about 1000 mg/L, from about 0.1 mg/L to about 100 mg/L, or from about 1 mg/L to about 50 mg/L.

Organoaluminoxanes can be prepared by various procedures. Examples of organoaluminoxane preparations are disclosed in U.S. Pat. Nos. 3,242,099 and 4,808,561, the disclosures of which are incorporated herein by reference in their entirety. For example, water in an inert organic solvent can be reacted with an aluminum alkyl compound, such as $(R^C)_3Al$, to form the desired organoaluminoxane compound. While not intending to be bound by this statement, it is believed that this synthetic method can afford a mixture of both linear and cyclic R—Al—O aluminoxane species, both of which are encompassed by this invention. Alternatively, organoaluminoxanes are prepared by reacting an aluminum alkyl compound, such as $(R^C)_3Al$, with a hydrated salt, such as hydrated copper sulfate, in an inert organic solvent.

Organoboron/Organoborate Compounds

According to another aspect of the present invention, the catalyst composition can comprise an organoboron or organoborate compound. Such compounds include neutral boron compounds, borate salts, and the like, or combinations thereof. For example, fluoroorgano boron compounds and fluoroorgano borate compounds are contemplated.

Any fluoroorgano boron or fluoroorgano borate compound can be utilized with the present invention. Examples of fluoroorgano borate compounds that can be used in the present invention include, but are not limited to, fluorinated aryl borates such as N,N-dimethylanilinium tetrakis(pentafluorophenyl)borate, triphenylcarbenium tetrakis(pentafluorophenyl)borate, lithium tetrakis(pentafluorophenyl)borate, N,N-dimethylanilinium tetrakis[3,5-bis(trifluoromethyl)phenyl]borate, triphenylcarbenium tetrakis[3,5-bis(trifluoromethyl)phenyl]borate, and the like, or mixtures thereof. Examples of fluoroorgano boron compounds that can be used as co-catalysts in the present invention include, but are not limited to, tris(pentafluorophenyl)boron, tris[3,5-bis(trifluoromethyl)phenyl]boron, and the like, or mixtures thereof. Although not intending to be bound by the following theory, these examples of fluoroorgano borate and fluoroorgano boron compounds, and related compounds, are thought to form "weakly-coordinating" anions when combined with organometal compounds, as disclosed in U.S. Pat. No. 5,919,983, the disclosure of which is incorporated herein by reference in its entirety. Applicants also contemplate the use of diboron, or bis-boron, compounds or other bifunctional compounds containing two or more boron atoms in the chemical structure, such as disclosed in J. Am. Chem. Soc., 2005, 127, pp. 14756-14768, the content of which is incorporated herein by reference in its entirety.

Generally, any amount of organoboron compound can be used. According to one aspect of this invention, the molar ratio of the total moles of organoboron or organoborate compound (or compounds) to the total moles of imino carbene compounds/derivatives in the catalyst composition is in a range from about 0.1:1 to about 15:1. Typically, the amount of the fluoroorgano boron or fluoroorgano borate compound used is from about 0.5 moles to about 10 moles of boron/borate compound per mole of imino carbene compounds/derivatives. According to another aspect of this invention, the amount of fluoroorgano boron or fluoroorgano borate compound is from about 0.8 moles to about 5 moles of boron/borate compound per mole of imino carbene compounds/derivatives.

Ionizing Ionic Compounds

The present invention further provides a catalyst composition which can comprise an ionizing ionic compound. An ionizing ionic compound is an ionic compound that can function as a co-catalyst to enhance the activity of the catalyst composition. While not intending to be bound by theory, it is believed that the ionizing ionic compound may be capable of reacting with an imino carbene compound/derivative and converting the imino carbene compound/derivative into one or more cationic complexes. Again, while not intending to be bound by theory, it is believed that the ionizing ionic compound can function as an ionizing compound by completely or partially extracting an anionic ligand, possibly a non-alkadienyl ligand, from the imino carbene compound/derivative. However, the ionizing ionic compound is an activator or co-catalyst regardless of whether it is ionizes the imino carbene compound/derivative, abstracts a ligand in a fashion as to form an ion pair, weakens a metal-ligand bond in the imino carbene compound/derivative, simply coordinates to a ligand, or activates the imino carbene compound/derivative by some other mechanism.

Further, it is not necessary that the ionizing ionic compound activate the imino carbene compound/derivative only. The activation function of the ionizing ionic compound can be evident in the enhanced activity of catalyst composition as a whole, as compared to a catalyst composition that does not contain an ionizing ionic compound.

Examples of ionizing ionic compounds include, but are not limited to, the following compounds: tri(n-butyl)ammonium tetrakis(p-tolyl)borate, tri(n-butyl) ammonium tetrakis(m-tolyl)borate, tri(n-butyl)ammonium tetrakis(2,4-dimethylphenyl)borate, tri(n-butyl)ammonium tetrakis(3,5-dimethylphenyl)borate, tri(n-butyl)ammonium tetrakis [3,5-bis(trifluoromethyl)phenyl]borate, tri(n-butyl)ammonium tetrakis(pentafluorophenyl)borate, N,N-dimethylanilinium tetrakis(p-tolyl)borate, N,N-dimethylanilinium tetrakis(m-tolyl)borate, N,N-dimethylanilinium tetrakis(2,4-dimethylphenyl)borate, N,N-dimethylanilinium tetrakis(3,5-dimethyl-phenyl)borate, N,N-dimethylanilinium tetrakis[3,5-bis(trifluoromethyl)phenyl]borate, N,N-dimethylanilinium tetrakis(pentafluorophenyl)borate, triphenylcarbenium tetrakis(p-tolyl)borate, triphenylcarbenium tetrakis(m-tolyl)borate, triphenylcarbenium tetrakis(2,4-dimethylphenyl)borate, triphenylcarbenium tetrakis(3,5-dimethylphenyl)borate, triphenylcarbenium tetrakis[3,5-bis(trifluoro-methyl)phenyl]borate, triphenylcarbenium tetrakis(pentafluorophenyl)borate, tropylium tetrakis(p-tolyl)borate, tropylium tetrakis(m-tolyl)borate, tropylium tetrakis(2,4-dimethylphenyl)borate, tropylium tetrakis(3,5-dimethylphenyl)borate, tropylium tetrakis[3,5-bis(trifluoromethyl)phenyl]borate, tropylium tetrakis(pentafluorophenyl)borate, lithium tetrakis(pentafluorophenyl)borate, lithium tetraphenylborate, lithium tetrakis(p-tolyl)borate, lithium tetrakis(m-tolyl)borate, lithium tetrakis(2,4-dimethylphenyl)borate, lithium tetrakis(3,5-dimethylphenyl)borate, lithium tetrafluoroborate, sodium tetrakis(pentafluorophenyl)borate, sodium tetraphenylborate, sodium tetrakis(p-tolyl)borate, sodium tetrakis(m-tolyl)borate, sodium tetrakis(2,4-dimethylphenyl)borate, sodium tetrakis(3,5-dimethylphenyl)borate, sodium tetrafluoroborate, potassium tetrakis(pentafluorophenyl)borate, potassium tetraphenylborate, potassium tetrakis(p-tolyl)borate, potassium tetrakis(m-tolyl)borate, potassium tetrakis(2,4-dimethylphenyl)borate, potassium tetrakis(3,5-dimethylphenyl)borate, potassium tetrafluoroborate, lithium tetrakis(pentafluorophenyl)aluminate, lithium tetraphenylaluminate, lithium tetrakis(p-tolyl)aluminate, lithium tetrakis(m-tolyl)aluminate, lithium tetrakis(2,4-dimethylphenyl)aluminate, lithium tetrakis(3,5-dimethylphenyl)aluminate, lithium tetrafluoroaluminate, sodium tetrakis(pentafluorophenyl)aluminate, sodium tetraphenylaluminate, sodium tetrakis(p-tolyl)aluminate, sodium tetrakis(m-tolyl)aluminate, sodium tetrakis(2,4-dimethylphenyl)aluminate, sodium tetrakis(3,5-dimethylphenyl)aluminate, sodium tetrafluoroaluminate, potassium tetrakis(pentafluorophenyl)aluminate, potassium tetraphenylaluminate, potassium tetrakis(p-tolyl)aluminate, potassium tetrakis(m-tolyl)aluminate, potassium tetrakis(2,4-dimethylphenyl)aluminate, potassium tetrakis (3,5-dimethylphenyl)aluminate, potassium tetrafluoroaluminate, and the like, or combinations thereof. Ionizing ionic compounds useful in this invention are not limited to these; other examples of ionizing ionic compounds are disclosed in U.S. Pat. Nos. 5,576,259 and 5,807,938, the disclosures of which are incorporated herein by reference in their entirety.

Olefin Monomers

Unsaturated reactants that can be employed with catalyst compositions and polymerization processes of this invention typically include olefin compounds having from 2 to 30 carbon atoms per molecule and having at least one olefinic double bond. This invention encompasses homopolymerization processes using a single olefin such as ethylene or propylene, as well as copolymerization, terpolymerization, etc., reactions using an olefin monomer with at least one different olefinic compound. For example, the resultant ethylene copolymers, terpolymers, etc., generally contain a major amount of ethylene (>50 mole percent) and a minor amount of comonomer (<50 mole percent), though this is not a requirement. Comonomers that can be copolymerized with ethylene often have from 3 to 20 carbon atoms in their molecular chain.

Acyclic, cyclic, polycyclic, terminal ($\alpha$), internal, linear, branched, substituted, unsubstituted, functionalized, and non-functionalized olefins can be employed in this invention. For example, typical unsaturated compounds that can be polymerized with the catalyst compositions of this invention include, but are not limited to, ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-hexene, 3-ethyl-1-hexene, 1-heptene, 2-heptene, 3-heptene, the four normal octenes (e.g., 1-octene), the four normal nonenes, the five normal decenes, and the like, or mixtures of two or more of these compounds. Cyclic and bicyclic olefins, including but not limited to, cyclopentene, cyclohexene, norbornylene, norbornadiene, and the like, also can be polymerized as described above. Styrene can also be employed as a monomer in the present invention. In an aspect, the olefin monomer is a $C_2$-$C_{10}$ olefin; alternatively, the olefin monomer is ethylene; or alternatively, the olefin monomer is propylene.

When a copolymer (or alternatively, a terpolymer) is desired, the olefin monomer can comprise, for example, ethylene or propylene, which is copolymerized with at least one comonomer. According to one aspect of this invention, the olefin monomer in the polymerization process comprises ethylene. In this aspect, examples of suitable olefin comonomers include, but are not limited to, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, styrene, and the like, or combinations thereof. According to one aspect of the present invention, the comonomer can comprise 1-butene, 1-pentene, 1-hexene, 1-octene, 1-decene, styrene, or any combination thereof.

Generally, the amount of comonomer introduced into a reactor zone to produce the copolymer is from about 0.01 to about 50 weight percent of the comonomer based on the total weight of the monomer and comonomer. According to another aspect of the present invention, the amount of comonomer introduced into a reactor zone is from about 0.01 to about 40 weight percent comonomer based on the total weight of the monomer and comonomer. In still another aspect, the amount of comonomer introduced into a reactor zone is from about 0.1 to about 35 weight percent comonomer based on the total weight of the monomer and comonomer. In yet another aspect, the amount of comonomer introduced into a reactor zone is from about 0.5 to about 20 weight percent comonomer based on the total weight of the monomer and comonomer.

While not intending to be bound by this theory, where branched, substituted, or functionalized olefins are used as reactants, it is believed that a steric hindrance can impede and/or slow the polymerization process. Thus, branched and/or cyclic portion(s) of the olefin removed somewhat from the carbon-carbon double bond would not be expected to hinder the reaction in the way that the same olefin substituents situated more proximate to the carbon-carbon double bond might. According to one aspect of the present invention, at least one monomer/reactant is ethylene, so the polymerizations are either a homopolymerization involving only ethylene, or copolymerizations with a different acyclic, cyclic, terminal, internal, linear, branched, substituted, or unsubstituted olefin. In addition, the catalyst compositions of this invention can be used in the polymerization of diolefin compounds including, but not limited to, 1,3-butadiene, isoprene, 1,4-pentadiene, and 1,5-hexadiene.

Catalyst Composition

The present invention can employ catalyst compositions containing at least one activator and at least one imino carbene compound/derivative (i.e., a compound having formula (I), or a compound having formula (II), or a compound having formula (III), or a compound having formula (IV), or a compound having formula (IV-A), or a compound having formula (IV-B), or a compound having formula (V), or a compound having formula (VII), or any combination thereof). These catalyst compositions can be utilized to produce polyolefins—homopolymers, copolymers, and the like—for a variety of end-use applications. In aspects of the present invention, it is contemplated that the catalyst composition can contain more than one imino carbene compound/derivative and/or the catalyst composition can contain one or more metallocene compound(s). Hence, in addition to an imino carbene compound/derivative, the catalyst composition can contain a metallocene compound. Additionally, more than one activator also may be utilized.

Generally, catalyst compositions of the present invention comprise an imino carbene compound/derivative and an activator. In aspects of the invention, the activator can comprise at least one activator-support. Activator-supports useful in the present invention were disclosed above. Such catalyst compositions can further comprise one or more than one organoaluminum compound or compounds (suitable organoaluminum compounds also were discussed above). Thus, a catalyst composition of this invention can comprise at least one imino carbene compound/derivative, at least one activator-support, and at least one organoaluminum compound. For instance, the activator-support can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, or combinations thereof. Additionally, the organoaluminum compound can comprise trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, and the like, or combinations thereof.

In another aspect of the present invention, a catalyst composition is provided which comprises an imino carbene compound/derivative, an activator-support, and an organoaluminum compound, wherein this catalyst composition is substantially free of aluminoxanes, organoboron or organoborate compounds, ionizing ionic compounds, and/or other similar materials; alternatively, substantially free of aluminoxanes; alternatively, substantially free or organoboron or organoborate compounds; or alternatively, substantially free of ionizing ionic compounds. In these aspects, the catalyst composition has catalyst activity, to be discussed below, in the absence of these additional materials. For example, a catalyst composition of the present invention can consist essentially of an imino carbene compound/derivative, an activator-support, and an organoaluminum compound, wherein no other materials are present in the catalyst composition which would increase/decrease the activity of the catalyst composition by more than about 10% from the catalyst activity of the catalyst composition in the absence of said materials.

However, in other aspects of this invention, these activators/co-catalysts can be employed. For example, a catalyst composition comprising an imino carbene compound/derivative and an activator-support can further comprise an optional co-catalyst. Suitable co-catalysts in this aspect include, but are not limited to, aluminoxane compounds, organoboron or organoborate compounds, ionizing ionic compounds, and the like, or any combination thereof. More than one co-catalyst can be present in the catalyst composition.

In a different aspect, a catalyst composition is provided which does not require an activator-support. Such a catalyst composition can comprise an imino carbene compound/derivative and at least one activator, wherein the at least one activator comprises at least one aluminoxane compound, at least one organoboron or organoborate compound, at least one ionizing ionic compound, or combinations thereof. According to one aspect of this invention, the at least one activator comprises at least one aluminoxane compound. According to another aspect, the at least one activator comprises at least one organoboron or organoborate compound. According to yet another aspect, the at least one activator comprises at least one ionizing ionic compound. According to still another aspect, the at least one activator comprises at least one activator-support comprising a clay mineral, a pillared clay, an exfoliated clay, an exfoliated clay gelled into another oxide matrix, a layered silicate mineral, a non-layered silicate mineral, a layered aluminosilicate mineral, a non-layered aluminosilicate mineral, or any combination thereof.

This invention further encompasses methods of making these catalyst compositions, such as, for example, contacting the respective catalyst components in any order or sequence.

The imino carbene compound/derivative can be precontacted with an olefinic monomer if desired, not necessarily the olefin monomer to be polymerized, and an organoaluminum compound for a first period of time prior to contacting this precontacted mixture with an activator-support. The first period of time for contact, the precontact time, between the imino carbene compound/derivative, the olefinic monomer, and the organoaluminum compound typically ranges from a time period of about 1 minute to about 24 hours, for example, from about 0.05 hours to about 1 hour. Precontact times from about 10 minutes to about 30 minutes are also employed. Alternatively, the precontacting process is carried out in multiple steps, rather than a single step, in which multiple mixtures are prepared, each comprising a different set of catalyst components. For example, at least two catalyst components are contacted forming a first mixture, followed by contacting the first mixture with at least one other catalyst component forming a second mixture, and so forth.

Multiple precontacting steps can be carried out in a single vessel or in multiple vessels. Further, multiple precontacting steps can be carried out in series (sequentially), in parallel, or a combination thereof. For example, a first mixture of two catalyst components can be formed in a first vessel, a second mixture comprising the first mixture plus one additional catalyst component can be formed in the first vessel or in a second vessel, which is typically placed downstream of the first vessel.

In another aspect, one or more of the catalyst components can be split and used in different precontacting treatments. For example, part of a catalyst component is fed into a first precontacting vessel for precontacting with at least one other catalyst component, while the remainder of that same catalyst component is fed into a second precontacting vessel for precontacting with at least one other catalyst component, or is fed directly into the reactor, or a combination thereof. The precontacting can be carried out in any suitable equipment, such as tanks, stirred mix tanks, various static mixing devices, a flask, a vessel of any type, or combinations of these apparatus.

In another aspect of this invention, the various catalyst components (for example, imino carbene compound/derivative, activator-support, organoaluminum co-catalyst, and optionally an unsaturated hydrocarbon) are contacted in the polymerization reactor simultaneously while the polymerization reaction is proceeding. Alternatively, any two or more of these catalyst components can be precontacted in a vessel prior to entering the reaction zone. This precontacting step can be continuous, in which the precontacted product is fed continuously to the reactor, or it can be a stepwise or batchwise process in which a batch of precontacted product is added to make a catalyst composition. This precontacting step can be carried out over a time period that can range from a few seconds to as much as several days, or longer. In this aspect, the continuous precontacting step generally lasts from about 1 second to about 1 hour. In another aspect, the continuous precontacting step lasts from about 10 seconds to about 45 minutes, or from about 1 minute to about 30 minutes.

Once the precontacted mixture of an imino carbene compound/derivative, olefin monomer, and organoaluminum co-catalyst is contacted with the activator-support, this composition (with the addition of the activator-support) is termed the "postcontacted mixture." The postcontacted mixture optionally remains in contact for a second period of time, the postcontact time, prior to initiating the polymerization process. Postcontact times between the precontacted mixture and the activator-support generally range from about 1 minute to about 24 hours. In a further aspect, the postcontact time is in a range from about 0.05 hours to about 1 hour. The precontacting step, the postcontacting step, or both, can increase the productivity of the polymer as compared to the same catalyst composition that is prepared without precontacting or postcontacting. However, neither a precontacting step nor a postcontacting step is required.

The postcontacted mixture can be heated at a temperature and for a time period sufficient to allow adsorption, impregnation, or interaction of precontacted mixture and the activator-support, such that a portion of the components of the precontacted mixture is immobilized, adsorbed, or deposited thereon. Where heating is employed, the postcontacted mixture generally is heated to a temperature of from between about 0° F. to about 150° F., or from about 40° F. to about 95° F.

When a precontacting step is used, the molar ratio of the total moles of olefin monomer to total moles of imino carbene compound/derivative (and metallocene compound present, if any) in the precontacted mixture is typically in a range from about 1:10 to about 100,000:1. Total moles of each component are used in this ratio to account for aspects of this invention where more than one olefin monomer and/or more than one imino carbene compound/derivative and/or metallocene compound is employed in a precontacting step. Further, this molar ratio can be in a range from about 10:1 to about 1,000:1 in another aspect of the invention.

Generally, the weight ratio of organoaluminum compound to activator-support is in a range from about 10:1 to about 1:1000. If more than one organoaluminum compound and/or more than one activator-support is employed, this ratio is based on the total weight of each respective component. In another aspect, the weight ratio of the organoaluminum compound to the activator-support is in a range from about 3:1 to about 1:100, or from about 1:1 to about 1:50.

In some aspects of this invention, the weight ratio of imino carbene compound/derivative (total of imino carbene compound(s)/derivative(s) and metallocene compound(s), if present) to activator-support is in a range from about 1:1 to about 1:1,000,000. If more than one activator-support is employed, this ratio is based on the total weight of the activator-support. In another aspect, this weight ratio is in a range from about 1:5 to about 1:100,000, or from about 1:10 to about 1:10,000. In yet another aspect, the weight ratio of the imino carbene compound/derivative to the activator-support is in a range from about 1:20 to about 1:1000.

Catalyst compositions of the present invention generally have a catalyst activity greater than about 100 grams of polyethylene (homopolymer, copolymer, etc., as the context requires) per gram of activator-support per hour (abbreviated gP/(gAS~hr)). In another aspect, the catalyst activity is greater than about 150, greater than about 250, or greater than about 500 gP/(gAS·hr). In still another aspect, catalyst compositions of this invention are characterized by having a catalyst activity greater than about 1000, greater than about 1500, or greater than about 2000 gP/(gAS·hr). In yet another aspect, the catalyst activity is greater than about 2500 gP/(gAS·hr). This activity is measured under slurry polymerization conditions using isobutane as the diluent, at a polymerization temperature of about 90° C. and a reactor pressure of about 450 psig.

In other aspects, catalyst compositions of the present invention can have a catalyst activity greater than about 500 grams of polyethylene (homopolymer, copolymer, etc., as the context requires) per gram of imino carbene compound/derivative per hour (abbreviated gP/(gIC·hr)). For instance, the catalyst activity can be greater than about 1000 gP/(gIC·hr); alternatively, greater than about 1500 gP/(gIC·hr); alternatively, greater than about 2000 gP/(gIC·hr); alternatively, greater than about 2500 gP/(gIC·hr); alternatively, greater than about 3000 gP/(gIC·hr); alternatively, greater than about 4000 gP/(gIC·hr); or alternatively, greater than about 5000 gP/(gIC·hr).

As discussed above, any combination of the imino carbene compound/derivative, the activator-support, the organoaluminum compound, and the olefin monomer, can be precontacted in some aspects of this invention. When any precontacting occurs with an olefinic monomer, it is not necessary that the olefin monomer used in the precontacting step be the same as the olefin to be polymerized. Further, when a precontacting step among any combination of the catalyst components is employed for a first period of time, this precontacted mixture can be used in a subsequent postcontacting step between any other combination of catalyst components for a second period of time. For example, one or more imino carbene compounds/derivatives, the organoaluminum compound, and 1-hexene can be used in a precontacting step for a first period of time, and this precontacted mixture then can be contacted with the activator-support to form a postcontacted mixture that is contacted for a second period of time prior to initiating the polymerization reaction. For example, the first period of time for contact, the precontact time, between any combination of the imino carbene compound/derivative, the olefinic monomer, the activator-support, and the organoaluminum compound can be from about 1 minute to about 24 hours, from about 3 minutes to about 1 hour, or from about 10 minutes to about 30 minutes. The postcontacted mixture optionally is allowed to remain in contact for a second period of time, the postcontact time, prior to initiating the polymerization process. According to one aspect of this invention, postcontact times between the precontacted mixture and any remaining catalyst components is from about 1 minute to about 24 hours, or from about 0.1 hour to about 1 hour.

Polymerization Process

Catalyst compositions of the present invention can be used to polymerize olefins to form homopolymers, copolymers, terpolymers, and the like. One such process for polymerizing olefins in the presence of a catalyst composition of the present invention comprises contacting the catalyst composition with an olefin monomer and optionally at least one olefin comonomer under polymerization conditions to produce an olefin polymer, wherein the catalyst composition comprises at least imino carbene compound/derivative and at least one activator.

In accordance with one aspect of the invention, the polymerization process employs a catalyst composition comprising an imino carbene compound/derivative and an activator, wherein the activator comprises an activator-support. This catalyst composition can further comprise an organoaluminum compound. Suitable organoaluminum compounds can include, but are not limited to, trimethylaluminum, triethylaluminum, tri-n-propylaluminum, tri-n-butylaluminum, tri-isobutylaluminum, tri-n-hexylaluminum, tri-n-octylaluminum, diisobutylaluminum hydride, diethylaluminum ethoxide, diethylaluminum chloride, and the like, or any combination thereof.

In accordance with yet another aspect of the invention, the polymerization process employs a catalyst composition comprising an imino carbene compound/derivative and an activator, wherein the activator comprises at least one aluminoxane compound, at least one organoboron or organoborate compound, at least one ionizing ionic compound, or combinations thereof.

The catalyst compositions of the present invention are intended for any olefin polymerization method using various types of polymerization reactors. As used herein, "polymerization reactor" includes any polymerization reactor capable of polymerizing olefin monomers and comonomers (one or more than one comonomer) to produce homopolymers, copolymers, terpolymers, and the like. The various types of reactors include those that may be referred to as a batch reactor, slurry reactor, gas-phase reactor, solution reactor, high pressure reactor, tubular reactor, autoclave reactor, and the like, or combinations thereof. The polymerization conditions for the various reactor types are well known to those of skill in the art. Gas phase reactors may comprise fluidized bed reactors or staged horizontal reactors. Slurry reactors may comprise vertical or horizontal loops. High pressure reactors may comprise autoclave or tubular reactors. Reactor types can include batch or continuous processes. Continuous processes could use intermittent or continuous product discharge. Processes may also include partial or full direct recycle of unreacted monomer, unreacted comonomer, and/or diluent.

Polymerization reactor systems of the present invention may comprise one type of reactor in a system or multiple reactors of the same or different type. Production of polymers in multiple reactors may include several stages in at least two separate polymerization reactors interconnected by a transfer device making it possible to transfer the polymers resulting from the first polymerization reactor into the second reactor. The desired polymerization conditions in one of the reactors may be different from the operating conditions of the other reactors. Alternatively, polymerization in multiple reactors may include the manual transfer of polymer from one reactor to subsequent reactors for continued polymerization. Multiple reactor systems may include any combination including, but not limited to, multiple loop reactors, multiple gas phase reactors, a combination of loop and gas phase reactors, multiple high pressure reactors, or a combination of high pressure with loop and/or gas phase reactors. The multiple reactors may be operated in series, in parallel, or both.

According to one aspect of the invention, the polymerization reactor system may comprise at least one loop slurry reactor comprising vertical or horizontal loops. Monomer, diluent, catalyst, and comonomer may be continuously fed to a loop reactor where polymerization occurs. Generally, continuous processes may comprise the continuous introduction of monomer/comonomer, a catalyst, and a diluent into a polymerization reactor and the continuous removal from this reactor of a suspension comprising polymer particles and the diluent. Reactor effluent may be flashed to remove the solid polymer from the liquids that comprise the diluent, monomer and/or comonomer. Various technologies may be used for this separation step including but not limited to, flashing that may include any combination of heat addition and pressure reduction; separation by cyclonic action in either a cyclone or hydrocyclone; or separation by centrifugation.

A typical slurry polymerization process (also known as the particle form process) is disclosed, for example, in U.S. Pat. Nos. 3,248,179, 4,501,885, 5,565,175, 5,575,979, 6,239,235, 6,262,191, and 6,833,415, each of which is incorporated herein by reference in its entirety.

Suitable diluents used in slurry polymerization include, but are not limited to, the monomer being polymerized and hydrocarbons that are liquids under reaction conditions.

Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used. An example is polymerization of propylene monomer as disclosed in U.S. Pat. No. 5,455,314, which is incorporated by reference herein in its entirety.

According to yet another aspect of this invention, the polymerization reactor may comprise at least one gas phase reactor. Such systems may employ a continuous recycle stream containing one or more monomers continuously cycled through a fluidized bed in the presence of the catalyst under polymerization conditions. A recycle stream may be withdrawn from the fluidized bed and recycled back into the reactor. Simultaneously, polymer product may be withdrawn from the reactor and new or fresh monomer may be added to replace the polymerized monomer. Such gas phase reactors may comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 5,352,749, 4,588,790, and 5,436,304, each of which is incorporated by reference in its entirety herein.

According to still another aspect of the invention, a high pressure polymerization reactor may comprise a tubular reactor or an autoclave reactor. Tubular reactors may have several zones where fresh monomer, initiators, or catalysts are added. Monomer may be entrained in an inert gaseous stream and introduced at one zone of the reactor. Initiators, catalysts, and/or catalyst components may be entrained in a gaseous stream and introduced at another zone of the reactor. The gas streams may be intermixed for polymerization. Heat and pressure may be employed appropriately to obtain optimal polymerization reaction conditions.

According to yet another aspect of the invention, the polymerization reactor may comprise a solution polymerization reactor wherein the monomer/comonomer are contacted with the catalyst composition by suitable stirring or other means. A carrier comprising an inert organic diluent or excess monomer may be employed. If desired, the monomer/comonomer may be brought in the vapor phase into contact with the catalytic reaction product, in the presence or absence of liquid material. The polymerization zone is maintained at temperatures and pressures that will result in the formation of a solution of the polymer in a reaction medium. Agitation may be employed to obtain better temperature control and to maintain uniform polymerization mixtures throughout the polymerization zone. Adequate means are utilized for dissipating the exothermic heat of polymerization.

Polymerization reactors suitable for the present invention may further comprise any combination of at least one raw material feed system, at least one feed system for catalyst or catalyst components, and/or at least one polymer recovery system. Suitable reactor systems for the present invention may further comprise systems for feedstock purification, catalyst storage and preparation, extrusion, reactor cooling, polymer recovery, fractionation, recycle, storage, loadout, laboratory analysis, and process control.

Polymerization conditions that are controlled for efficiency and to provide desired polymer properties can include temperature, pressure, and the concentrations of various reactants. Polymerization temperature can affect catalyst productivity, polymer molecular weight, and molecular weight distribution. A suitable polymerization temperature may be any temperature below the de-polymerization temperature according to the Gibbs Free energy equation. Typically, this includes from about 60° C. to about 280° C., for example, or from about 60° C. to about 110° C., depending upon the type of polymerization reactor. In some reactor systems, the polymerization temperature generally is within a range from about 70° C. to about 90° C., or from about 75° C. to about 85° C.

Suitable pressures will also vary according to the reactor and polymerization type. The pressure for liquid phase polymerizations in a loop reactor is typically less than 1000 psig. Pressure for gas phase polymerization is usually at about 200 to 500 psig. High pressure polymerization in tubular or autoclave reactors is generally run at about 20,000 to 75,000 psig. Polymerization reactors can also be operated in a supercritical region occurring at generally higher temperatures and pressures. Operation above the critical point of a pressure/temperature diagram (supercritical phase) may offer advantages.

Polymerization processes of this invention can be conducted in the presence of hydrogen, although this is not a requirement. According to one aspect of this invention, the ratio of hydrogen to the olefin monomer in the polymerization process is controlled. This weight ratio can range from δ ppm to about 10,000 ppm of hydrogen, based on the weight of the olefin monomer. For instance, the reactant or feed ratio of hydrogen to olefin monomer can be controlled at a weight ratio which falls within a range from δ ppm to about 7500 ppm, from about δ ppm to about 5000 ppm, or from about 10 ppm to about 1000 ppm.

However, in another aspect, it is contemplated that monomer, comonomer (or comonomers), and/or hydrogen can be periodically pulsed to the reactor, for instance, in a manner similar to that employed in U.S. Pat. No. 5,739,220 and U.S. Patent Publication No. 2004/0059070, the disclosures of which are incorporated herein by reference in their entirety.

The concentration of the reactants entering the polymerization reactor can be controlled to produce resins with certain physical and mechanical properties. The proposed end-use product that will be formed by the polymer resin and the method of forming that product ultimately can determine the desired polymer properties and attributes. Mechanical properties include tensile, flexural, impact, creep, stress relaxation, and hardness tests. Physical properties include density, molecular weight, molecular weight distribution, melting temperature, glass transition temperature, temperature melt of crystallization, density, stereoregularity, crack growth, long chain branching, and rheological measurements.

This invention is also directed to, and encompasses, the polymers produced by any of the polymerization processes disclosed herein. Articles of manufacture can be formed from, and/or can comprise, the polymers produced in accordance with this invention.

Polymers and Articles

If the resultant polymer produced in accordance with the present invention is, for example, a polymer or copolymer of ethylene, its properties can be characterized by various analytical techniques known and used in the polyolefin industry. Articles of manufacture can be formed from, and/or can comprise, the polymers of this invention, whose typical properties are provided below.

Polymers of ethylene (copolymers, terpolymers, etc.) produced in accordance with this invention generally have a melt index from about 0.001 to about 100 g/10 min. Melt indices in the range from about 0.001 to about 75 g/10 min, from about 0.01 to about 50 g/10 min, or from about 0.05 to about 30 g/10 min, are contemplated in some aspects of this invention. For example, a polymer of the present invention can have a melt index (MI) in a range from about 0.05 to about 25, or from about 0.1 to about 10 g/10 min.

Ethylene polymers produced in accordance with this invention can have a ratio of HLMI/MI in a range from about 5 to about 150, such as, for example, from about 10 to about 125, from about 10 to about 100, from about 15 to about 90, from about 15 to about 80, from about 20 to about 70, or from about 25 to about 65.

The density of ethylene-based polymers produced using the catalyst systems and processes disclosed herein typically falls within the range from about 0.88 to about 0.97 g/cm$^3$. In one aspect of this invention, the density of an ethylene polymer is in a range from about 0.90 to about 0.95 g/cm$^3$. In yet another aspect, the density is in a range from about 0.91 to about 0.945 g/cm$^3$, such as, for example, from about 0.92 to about 0.945 g/cm$^3$.

Polymers, whether homopolymers, copolymers, terpolymers, and so forth, can be formed into various articles of manufacture. Articles which can comprise polymers of this invention include, but are not limited to, an agricultural film, an automobile part, a bottle, a drum, a fiber or fabric, a food packaging film or container, a food service article, a fuel tank, a geomembrane, a household container, a liner, a molded product, a medical device or material, a pipe, a sheet or tape, a toy, and the like. Various processes can be employed to form these articles. Non-limiting examples of these processes can include injection molding, blow molding, rotational molding, film extrusion, sheet extrusion, profile extrusion, thermoforming, and the like. Additionally, additives and modifiers are often added to these polymers in order to provide beneficial polymer processing or end-use product attributes. Such processes and materials are described in *Modern Plastics Encyclopedia*, Mid-November 1995 Issue, Vol. 72, No. 12; and *Film Extrusion Manual—Process, Materials, Properties*, TAPPI Press, 1992; the disclosures of which are incorporated herein by reference in their entirety.

Applicants also contemplate a method for forming or preparing an article of manufacture comprising a polymer produced by any of the polymerization processes disclosed herein. For instance, a method can comprise (i) contacting a catalyst composition with an olefin monomer and optionally an olefin comonomer (one or more) under polymerization conditions to produce an olefin polymer, wherein the catalyst composition can comprise an imino carbene compound/derivative (i.e., a compound having formula (I), or a compound having formula (II), or a compound having formula (III), or a compound having formula (IV), or a compound having formula (IV-A), or a compound having formula (IV-B), or a compound having formula (V), or a compound having formula (VII), or any combination thereof), and an activator (e.g., an activator-support) and/or an organoaluminum compound; and (ii) forming an article of manufacture comprising the olefin polymer. The forming step can comprise blending, melt processing, extruding, molding, or thermoforming, and the like, including combinations thereof.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

NMR spectra were recorded on a Varian unity Inova 400 MHz spectrometer and residual solvent protons were used as internal standard. Elemental analyses were performed by Midwest Microlab LLC, of Indianapolis, Ind. X-ray crystal structures were determined from single crystal diffraction data obtained on a Bruker SMART Apex 11 diffractometer with Mo K-alpha radiation and a CCD area detector.

Example 1

α-Imino Imidazolium Cations, Used as Precursors for Compounds of Formula (I) with 5-Membered Chelate Rings The compounds synthesized in Scheme 1, below, are related to α-iminocarbene chelates reported by Tilset as ligands for palladium and platinum (see Frøseth, M., Netland, K. A., Rømming, C., Tilset, M., "Synthesis and characterization of novel Pd(II) and Pt(II) complexes with 5-ring chelating iminoylcarbene ligands," *J. Organomet. Chem.*, 2005, 690, 6125-6132, incorporated herein by reference in its entirety). The precursors for these compounds were prepared by reacting benzoyl chloride with anilines to obtain arylamides 1, followed by chlorination to obtain iminoyl chlorides 2 (Scheme 1). The first step of this reaction proceeded smoothly, but it was found that obtaining iminoyl chlorides 2 in pure form was much more difficult than indicated in the literature. Applicants found that it was beneficial to perform the reaction in an inert atmosphere at all stages, and to remove all traces of HCl and SOCl$_2$ via vacuum prior to purification. With this improved synthesis procedure, two derivatives containing bulky groups, 2a (previously reported by Tilset) and the new mesityl derivative 2b, were obtained in high purity and yield (85% and 86%, respectively). Applicants also discovered that 2a and 2b were sensitive to hydrolysis and can be stored cold in a glove box to maintain purity. Due to the instability of the products 2a and 2b, subsequent reactions generally were performed shortly after the production of these compounds.

Scheme 1

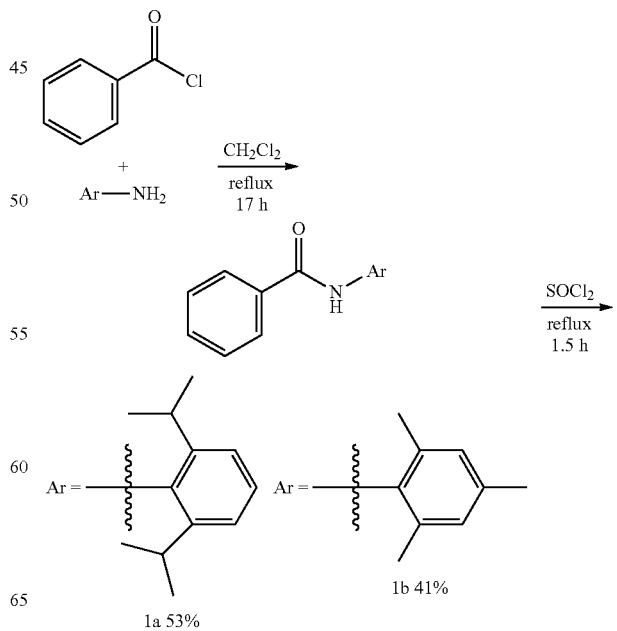

-continued

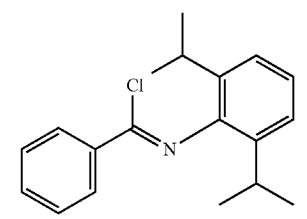

2a
85%

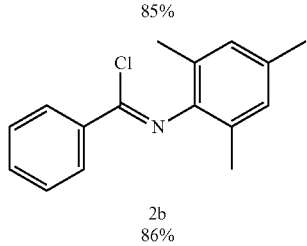

2b
86%

The α-imino imidazolium salts 3a and 3b, which can be precursors for the imino carbene compounds of formula (I), were prepared by reacting 2 with imidazoles (Scheme 2). Unexpectedly, attempts to place bulky aryl groups on the imidazoles did not lead to the desired products with iminoyl chloride 2a. Synthesis of compound 3a (R=Me) from 2a was performed as described by Tilset. The product was more sensitive than expected from Tilset, and careful glovebox techniques were employed. Surprisingly, samples of 3a prepared directly by the procedure described by Tilset were not adequately pure by $^1$H NMR. Applicants developed a method to achieve analytical purity using a recrystallization from CH$_2$Cl$_2$/hexanes; however, the yields suffered somewhat. Compound 3b (R=benzyl) was also prepared in pure form using the same recrystallization procedure.

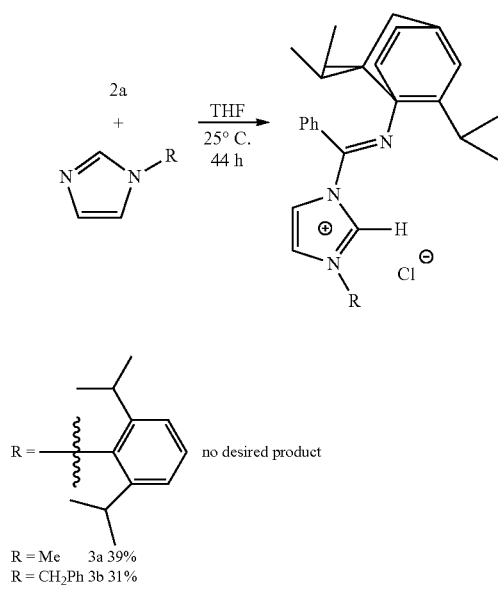

Using the procedure shown in Scheme 2, compound 3c (R=t-Bu) was prepared in 70% yield.

Example 2

Preparation of Carbene Ligand Precursors

The free carbene of the ligand precursor 3a (Scheme 4) was generated before attempting to form metal complexes. This was done in an attempt to avoid the formation of 2a, which may result from a benzyl group attacking the imidazolium carbon when Group 4 tetrabenzyl complexes are used as metalating agents. Bulky bases such as potassium tert-butoxide and potassium bis(trimethylsilyl)amide (also referred to as potassium hexamethyldisilazide) were employed. Small scale reactions were carried out with the ligand precursor 1a and either of the two bases in NMR tubes using C$_6$D$_6$ as solvent. In both cases, disappearance of the imidazolium hydrogen was evident, along with shifting of resonances when compared to spectra of the starting material. These results and the formation of KCl during the reaction indicated formation of the desired free carbene 3a. Interestingly, the spectra were broadened, which suggested that the carbene may be weakly coordinated to residual potassium chloride.

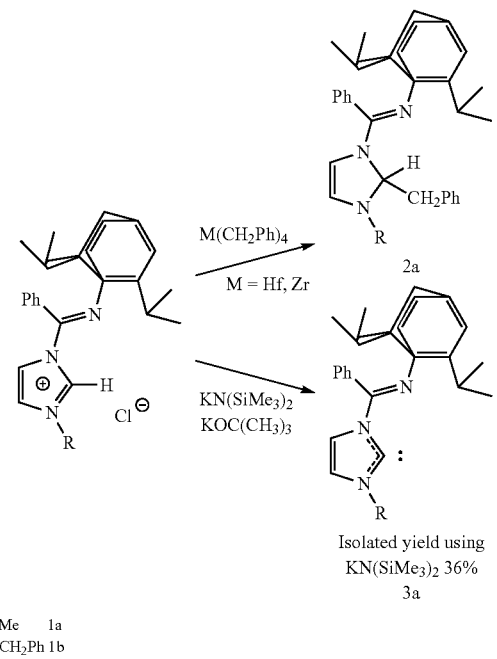

Attempts to isolate the free carbene when using KOC(CH$_3$)$_3$ were unsuccessful, as there was substantial decomposition during work up. When KN(SiMe$_3$)$_2$ was used, a product was isolated in low yield (36%). Metalation reactions of ZrCl$_4$(THF)$_2$ with compound 3a produced as shown in Scheme 4 were conducted, but removal of KCl was problematic. Some of the KCl that formed was a very fine precipitate, but it appeared that some may have been suspended in the solvent or tightly associated with the desired product. Filtering through celite was not sufficient to remove all traces.

A different silylamide salt, lithium hexamethyldisilazide, LiN(SiMe$_3$)$_2$ was used to produce the precursor ligand in many of the Examples that follow. Benzene was chosen as the solvent, instead of THF, traces of which may be difficult to remove from the final product. Additionally, LiCl was easier to remove from the final product than KCl.

Example 3

Synthesis of Compounds of Formula (I)

Hf(IV) and Zr(IV) iminocarbene complexes were synthesized via a carbene intermediate (Scheme 6). The lithium salt of hexamethyldisilazide [LiN(SiMe$_3$)$_2$] was utilized, which allowed the synthesis of pure organometallic products in higher yields.

Scheme 6

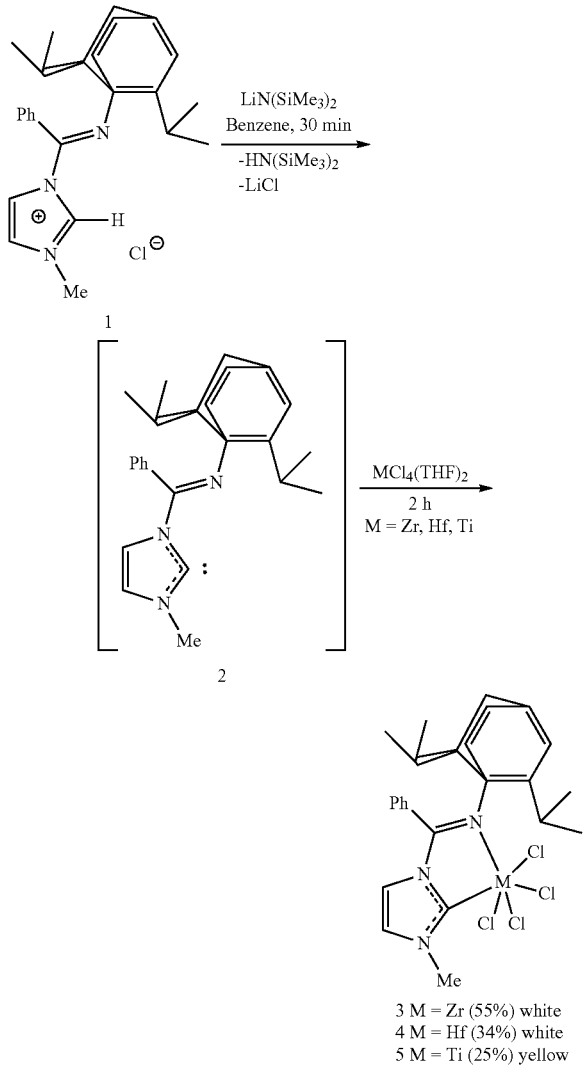

3 M = Zr (55%) white
4 M = Hf (34%) white
5 M = Ti (25%) yellow

Zr-complex 3 was synthesized as follows. The imidazolium chloride (0.40 g, 1.05 mmol) and lithium hexamethyldisilazide (0.19 g, 1.15 mmol) were stirred in 20 mL of benzene for 30 min. ZrCl$_4$(THF)$_2$ (0.40 g, 1.05 mmol) was then added to the solution in a single portion and the mixture allowed to stir for a further 2 hr at room temperature. The precipitate that formed was filtered and washed twice with benzene. All traces of benzene were then removed in vacuo and the residue was dissolved in dichloromethane and then passed through celite to remove LiCl. The filtrate was concentrated and pentane layered over the top. Solvent diffusion resulted in the appearance of a crystalline solid, which was filtered to produce compound 3 (0.33 g, 55% yield). $^1$H NMR (400 MHz, Dichloromethane-d$_2$) δ ppm 0.84 (d, J=6.64 Hz, 6 H, CHMe$_2$), 1.28 (d, J=6.64 Hz, 6 H, CHMe$_2$), 3.28 (septet, J=6.64 Hz, 2 H, CH), 4.16 (s, 3 H, CH$_3$), 6.94 (d, J=1.95 Hz, 1 H, CH), 7.05-7.12 (m, 3 H), 7.16-7.24 (m, 1 H), 7.27 (d, J=7.42 Hz, 2 H, CH), 7.40 (t, J=7.81 Hz, 2 H, CH), 7.50 (t, J=7.81 Hz, 1 H, CH). $^{13}$C NMR (101 MHz, Dichloromethane-d$_2$) δ ppm 24.0 (CHMe$_2$), 26.4 (CHMe$_2$), 28.5 (CHMe$_2$), 39.2 (imidazole CH$_3$), 121.0, 123.7, 124.9, 127.3, 128.0, 129.1, 129.7, 132.9, 141.5, 141.8, 162.8 (imine), 192.6 (carbene). Anal. Calculated for C$_{23}$H$_{27}$N$_3$Cl$_4$Zr: C, 47.75; H, 4.70; N, 7.26. Found C, 47.37; H, 4.71; N, 7.17. A $^1$H NMR spectrum of Zr-complex 3 is shown in FIG. 1.

Figure 2:
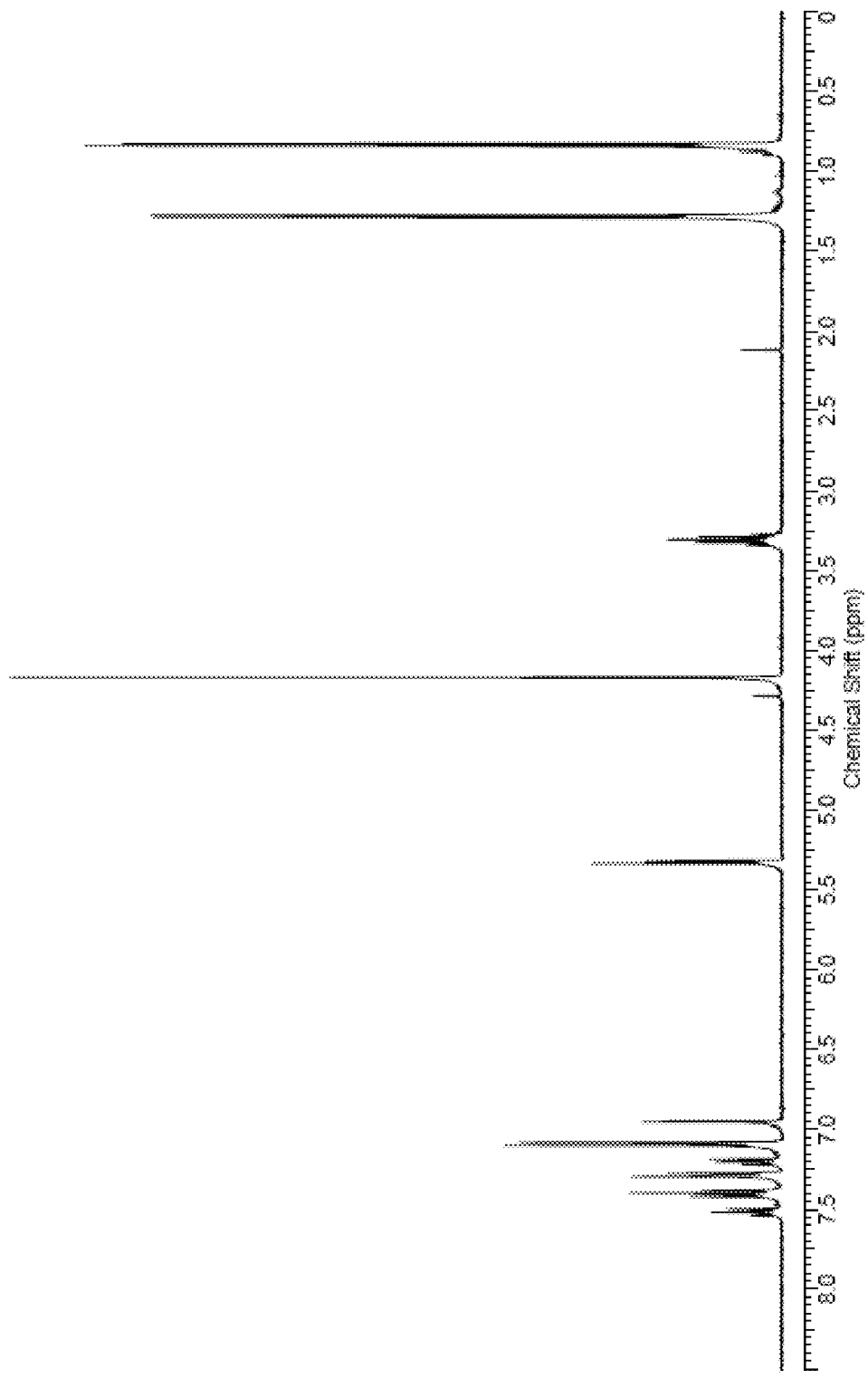
FIG. 2 presents a $^1$H NMR spectrum of Hf-complex 4 of Example 3.

Hf-complex 4 was synthesized in the same manner as Zr-complex 3, and was isolated as a white precipitate (0.10 g, 34% yield). $^1$H NMR (400 MHz, Dichloromethane-d$_2$) δ ppm 0.83 (d, J=6.64 Hz, 6 H, CHMe$_2$), 1.28 (d, J=6.64 Hz, 6 H, CHMe$_2$), 3.31 (septet, J=6.64 Hz, 2 H, CH), 4.17 (s, 3 H, CH$_3$), 6.95 (d, J=1.95 Hz, 1 H, CH), 7.05-7.13 (m, 3 H), 7.16-7.25 (m, 1 H), 7.28 (d, J=8.20 Hz, 2 H, CH), 7.40 (t, J=7.81 Hz, 2 H, CH), 7.51 (t, J=7.81 Hz, 1 H, CH). $^{13}$C NMR (101 MHz, Dichloromethane-d$_2$) δ ppm 24.1 (CHMe$_2$), 26.6 (CHMe$_2$), 28.5 (CHMe$_2$), 39.2 (imidazole CH$_3$), 121.2, 124.0, 125.0, 127.2, 128.1, 129.1, 129.8, 133.0, 141.4, 141.8, 163.3 (imine), 199.9 (carbene). Anal. Calculated for C$_{23}$H$_{27}$N$_3$Cl$_4$Hf: C, 41.49; H, 4.09; N, 6.31. Found C, 41.01; H, 4.02; N, 6.20. A $^1$H NMR spectrum of Hf-complex 4 is shown in FIG. 2.

Ti-complex 5 was synthesized in the same manner as Zr-complex 3, and was isolated as a yellow precipitate (25% yield). The precipitated LiCl was more difficult to remove. Several filtrations through packed celite were required, follow by glass microfiber, which contributed to the reduction in the yield. $^1$H NMR (400 MHz, Dichloromethane-d$_2$) δ ppm 0.85 (d, J=6.64 Hz, 6 H, CHMe$_2$), 1.30 (d, J=6.64 Hz, 6 H, CHMe$_2$), 3.29 (septet, J=6.64 Hz, 2 H, CH), 4.15 (s, 3 H, CH$_3$), 6.92 (d, J=2.34 Hz, 1 H, CH), 7.03-7.11 (m, 3 H), 7.15-7.22 (m, 1 H), 7.27 (d, J=7.8 Hz, 2 H, CH), 7.39 (t, J=7.81 Hz, 2 H, CH), 7.49 (t, J=7.81 Hz, 1 H, CH). $^{13}$C NMR (101 MHz, Dichloromethane-d$_2$) δ ppm 24.0 (CHMe$_2$), 26.5 (CHMe$_2$), 28.6 (CHMe$_2$), 39.0, 119.4, 123.5, 124.6, 127.3, 127.9, 129.1, 129.5, 132.7, 141.5, 143.7, 160.2 (imine), 194.6 (carbene). Anal. Calculated for C$_{23}$H$_{27}$N$_3$Cl$_4$Ti: C, 51.62; H, 5.08; N, 7.85. Found C, 51.22; H, 5.09; N, 7.59.

Figure 3:
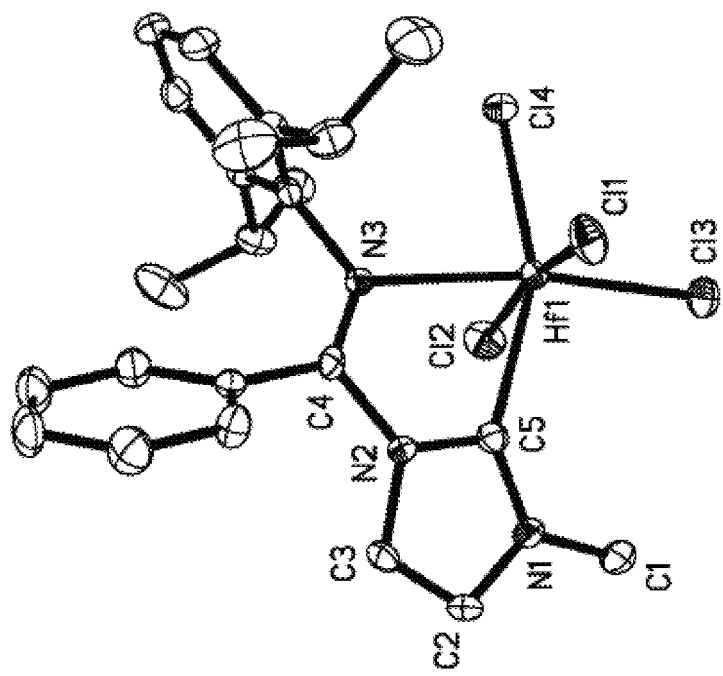
FIG. 3 illustrates the crystal structures of Zr-complex 3 (left) and Hf-complex 4 (right) of Example 3.
Figure 3:
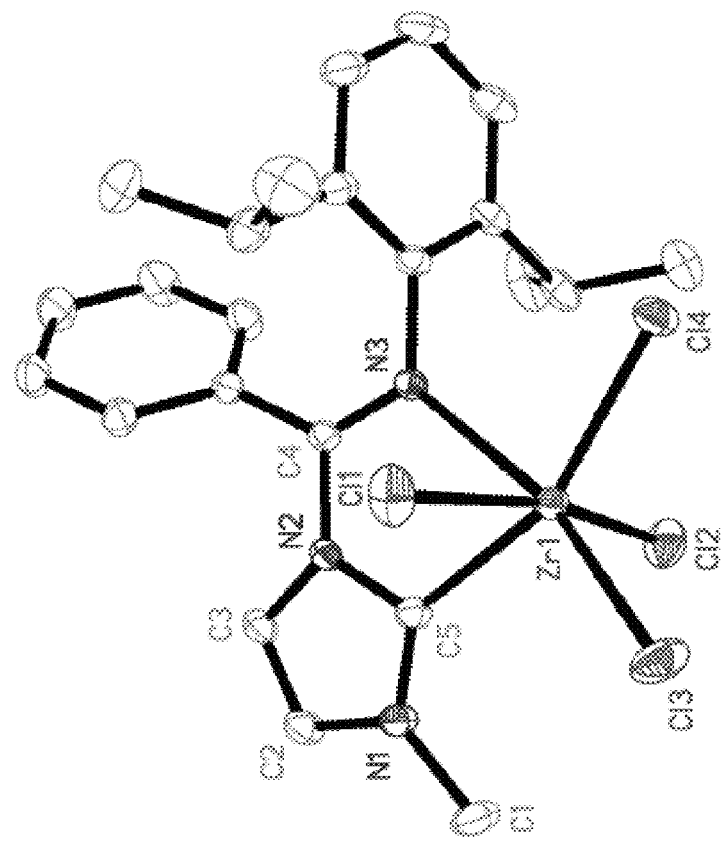

After successfully growing suitable crystals of complexes 3 and 4, their chemical structures were determined using X-ray crystallography. Both structures indicated metal tetrachloride complexes bound to the ligand via the carbene carbon and the imine nitrogen. The crystal structures are shown in FIG. 3. Crystals were grown by diffusing either n-hexane or pentane into methylene chloride solutions of 3 and 4, respectively.

Figure 4:
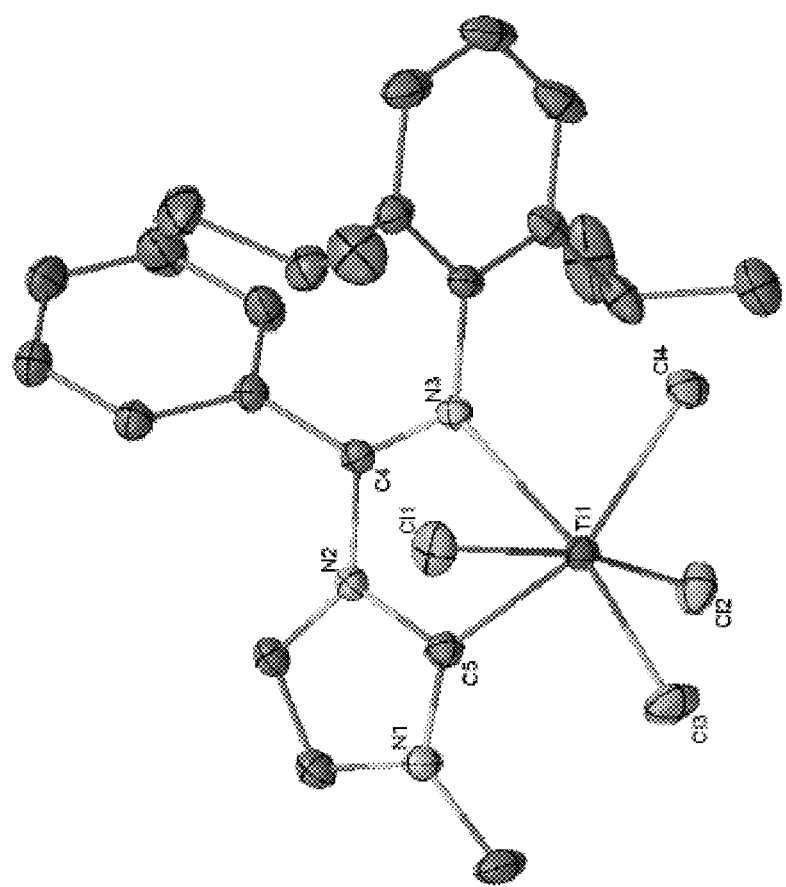
FIG. 4 illustrates the crystal structure of Ti-complex 5 of Example 3.

X-ray quality crystals of Ti-complex 5 were grown and the chemical structure, shown in FIG. 4, was obtained. The structure was as expected and analogous to the Hf and Zr counterparts. Crystals were grown by allowing pentane to slowly diffuse into a methylene chloride solution of the complex. Over the space of a week, suitable yellow crystals developed. $^{13}$C spectra were recorded, with the characteristic carbene carbon appearing in the 192.6-199.8 ppm range.

Example 4

Synthesis of Compounds of Formula (I)

Using procedures analogous to those described in Example 3, Zr-complex 8, Hf-complex 9, and Ti-complex 10 were produced. See Scheme 8 below.

Scheme 8

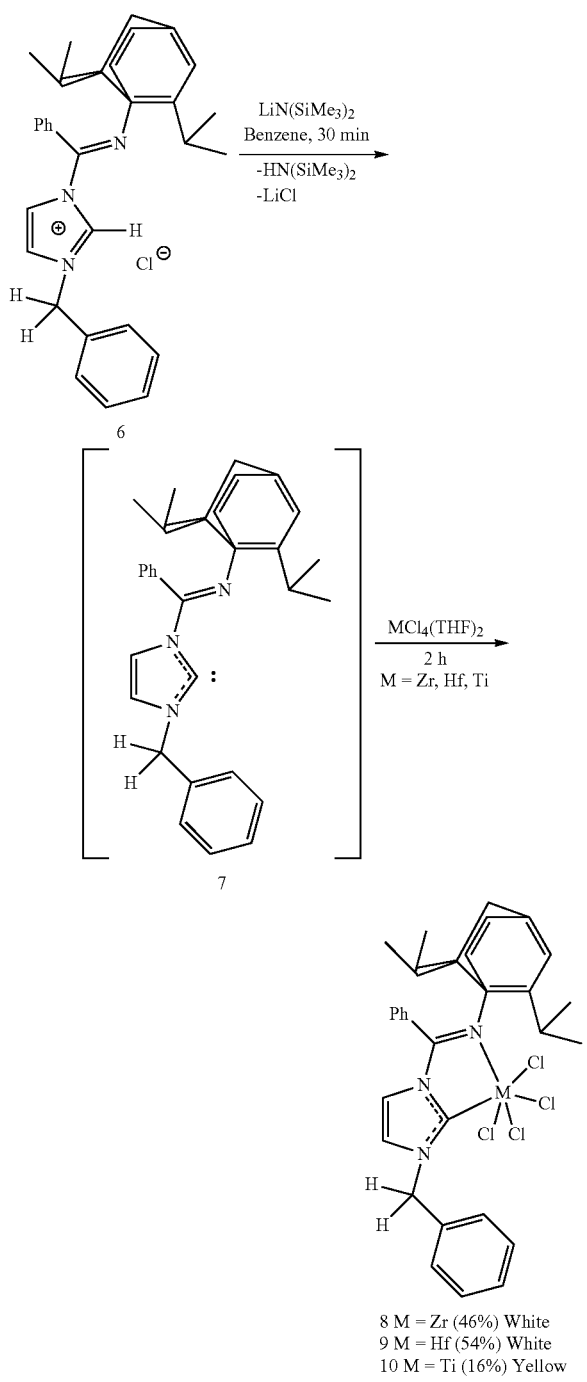

8 M = Zr (46%) White
9 M = Hf (54%) White
10 M = Ti (16%) Yellow

Figure 5:
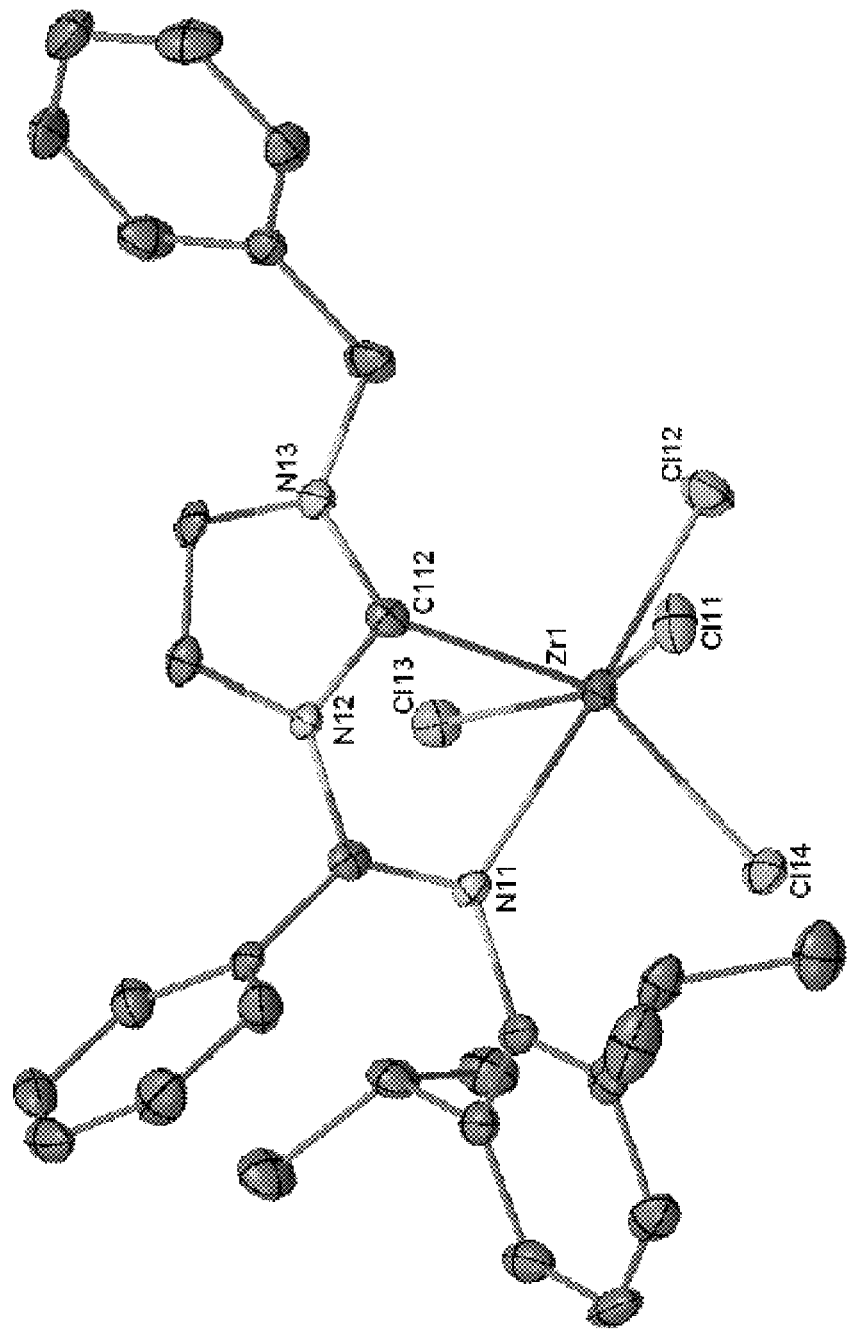
FIG. 5 illustrates the crystal structure of Zr-complex 8 of Example 4.

Zr-complex 8 was isolated as a white precipitate in 46% yield. $^1$H NMR (400 MHz, Dichloromethane-$d_2$) δ ppm 0.87 (d, J=6.64 Hz, 6 H, CHMe$_2$), 1.31 (d, J=6.64 Hz, 6 H, CHMe$_2$), 3.32 (septet, J=6.64 Hz, 2 H, CH), 5.69 (s, 2 H, CH$_2$), 6.92 (d, J=1.95 Hz, 1 H, CH), 6.96 (d, J=1.95 Hz, 1 H, CH), 7.06-7.13 (m, 2 H), 7.21 (t, J=7.80 Hz, 1 H, CH), 7.25-7.32 (m, 2 H), 7.39 (t, J=7.80 Hz, 2 H, CH) 7.42-7.53 (m, 4 H), 7.55-7.64 (m, 2 H). $^{13}$C NMR (101 MHz, Dichloromethane-$d_2$) δ ppm 24.1 (CHMe$_2$), 26.6 (CHMe$_2$), 28.5 (CHMe$_2$), 56.0, 121.6, 121.8, 124.9, 127.3, 128.0, 129.1, 129.5, 129.6, 129.7, 132.9, 134.3, 141.5, 141.9, 163.0 (imine), 192.2 (carbene). Anal. Calculated for C$_{29}$H$_{31}$N$_3$Cl$_4$Zr: C, 53.21; H, 4.77; N, 6.42. Found C, 52.89; H, 4.57; N, 6.26. Crystals suitable for X-ray analysis were grown from a methylene chloride solution of the complex, over which was layered pentane. The crystal structure, via x-ray analysis, of Zr-complex 8 is shown in FIG. 5.

Hf-complex 9 was isolated as a white precipitate in 54% yield. $^1$H NMR (400 MHz, Dichloromethane-$d_2$) δ ppm 0.87 (d, J=6.64 Hz, 6 H, CHMe$_2$), 1.31 (d, J=6.64 Hz, 6 H, CHMe$_2$), 3.35 (septet, J=6.64 Hz, 2 H, CH), 5.71 (s, 2 H, CH$_2$), 6.93 (d, J=1.95 Hz, 1 H, CH), 6.97 (d, J=1.95 Hz, 1 H, CH), 7.07-7.14 (m, 2 H), 7.21 (t, J=7.80 Hz, 1 H, CH), 7.27-7.33 (m, 2 H), 7.39 (t, J=7.80 Hz, 2 H, CH), 7.42-7.54 (m, 4 H), 7.55-7.63 (m, 2 H). $^{13}$C NMR (101 MHz, Dichloromethane-$d_2$) δ ppm 24.1 (CHMe$_2$), 26.7 (CHMe$_2$), 28.5 (CHMe$_2$), 55.9, 121.8, 122.1, 125.0, 127.3, 128.2, 129.1, 129.5, 129.6, 129.7, 133.0, 134.3, 141.5, 141.9, 163.7 (imine), 199.3 (carbene). Anal. Calculated for C$_{29}$H$_{31}$N$_3$Cl$_4$Hf: C, 46.95; H, 4.21; N, 5.66. Found C, 46.77; H, 4.25; N, 5.61.

Ti-complex 10 was isolated as a yellow precipitate after filtering first through celite, then glass microfiber (three times) to remove LiCl. The resulting yield was 16%. $^1$H NMR (400 MHz, Dichloromethane-$d_2$) δ ppm 0.86 (d, J=6.64 Hz, 6 H, CHMe$_2$), 1.33 (d, J=6.64 Hz, 6 H, CHMe$_2$), 3.32 (septet, J=6.64 Hz, 2 H, CH) 5.74 (s, 2 H, CH$_2$), 6.91 (d, J=2.34 Hz, 2 H, CH), 6.93 (d, J=2.34 Hz, 2 H, CH), 7.06-7.12 (m, 2 H), 7.19 (t, J=7.80 Hz, 1 H, CH), 7.26-7.32 (m, 2 H), 7.38 (t, J=8.20 Hz, 2 H, CH), 7.41-7.52 (m, 4 H), 7.55-7.62 (m, 2 H). $^{13}$C NMR (101 MHz, Dichloromethane-$d_2$) δ ppm 24.0 (CHMe$_2$), 26.6 (CHMe$_2$), 28.7 (CHMe$_2$), 55.4, 120.1, 121.5, 124.6, 127.9, 129.1, 129.4, 129.5, 129.6, 129.7, 132.7, 134.6, 141.6, 143.9, 160.5 (imine), 194.3 (carbene). Anal. Calculated for C$_{29}$H$_{31}$N$_3$Cl$_4$Ti: C, 56.98; H, 5.11; N, 7.84. Found C, 55.40; H, 5.13; N, 6.53.

For these three complexes, $^{13}$C NMR data were collected, and the characteristic carbene carbon for this series of complexes appeared in the range of 192.2-199.3 ppm.

Example 5

Synthesis of Compounds of Formula (I)

Using procedures analogous to those described above, Zr-complex 13 was produced. See Scheme 10 below.

Scheme 10

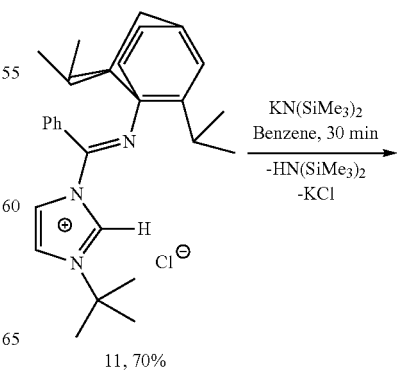

11, 70%

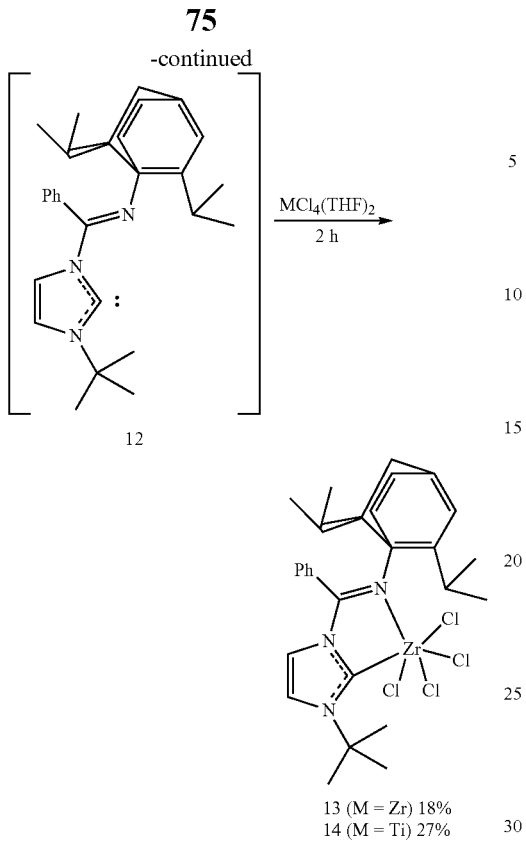

12

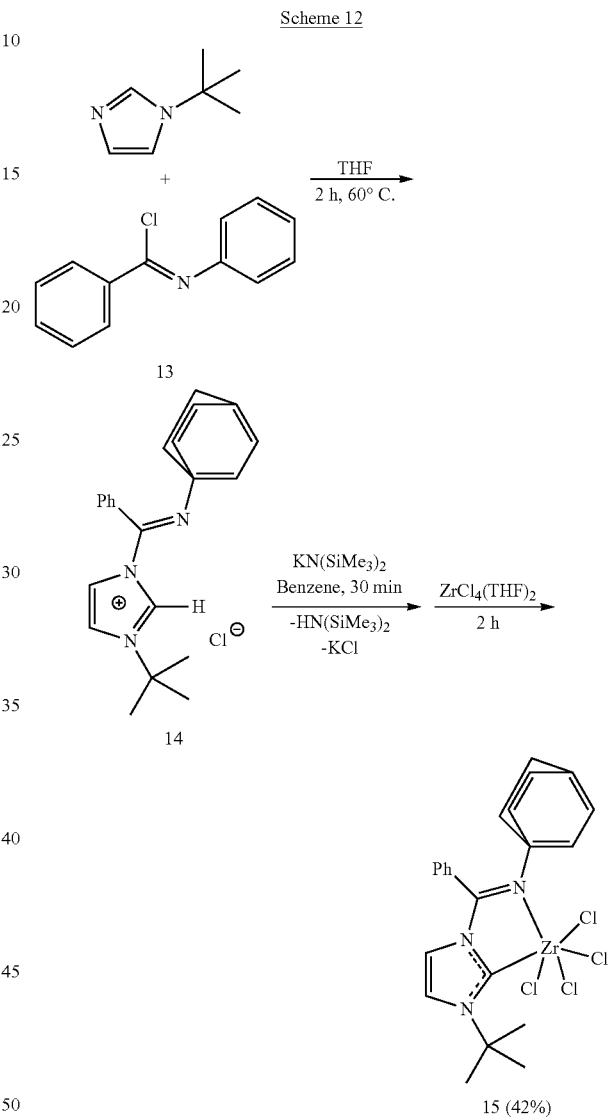

13 (M = Zr) 18%
14 (M = Ti) 27%

Figure 6:
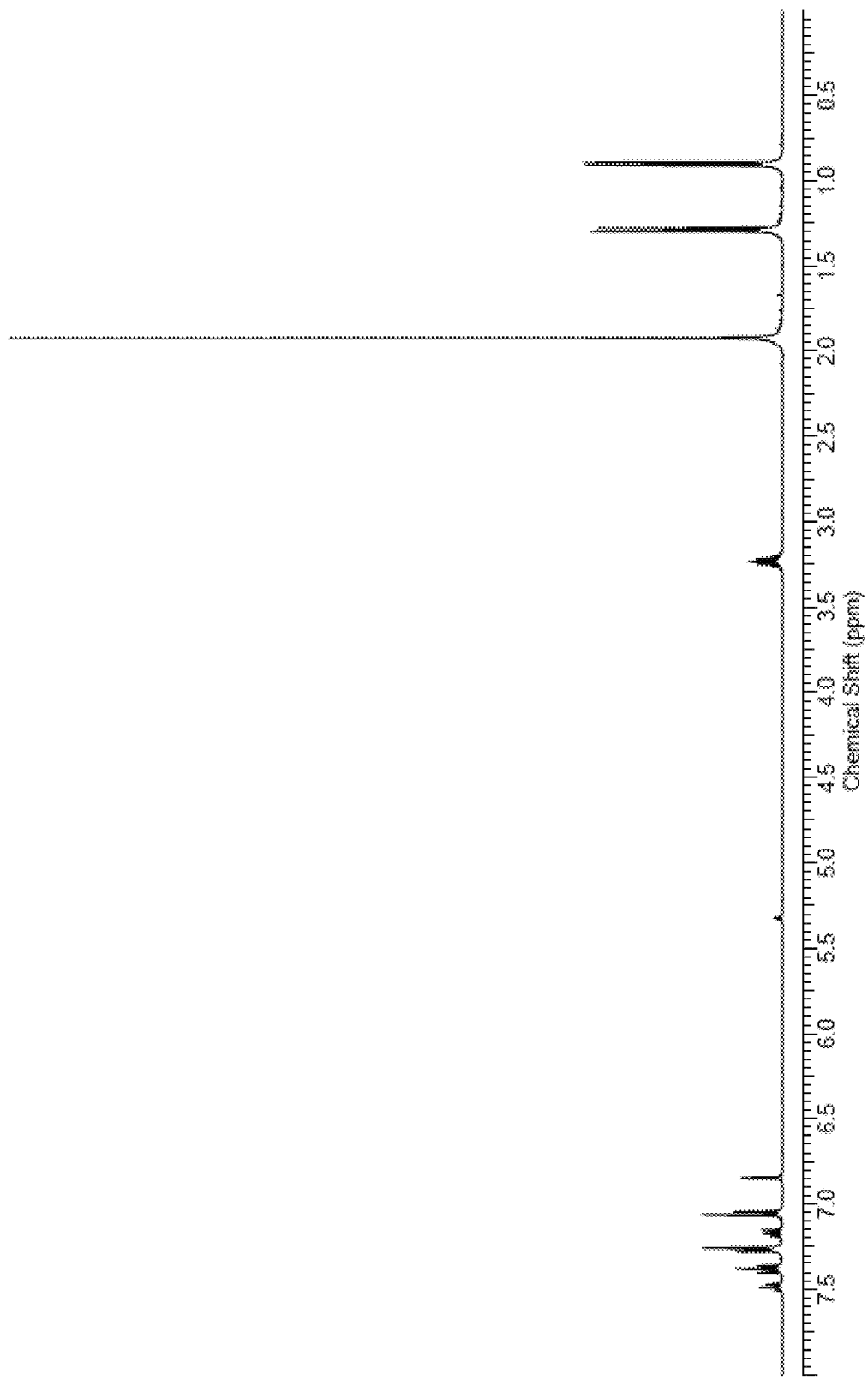
FIG. 6 presents a $^1$H NMR spectrum of Zr-complex 13 of Example 5.

Zr-complex 13 was isolated as a white precipitate in 18% yield, the low yield largely the result of the difficulty in removing KCl. Though the yield was low, the NMR spectrum indicated a product of high purity. The $^{13}$C spectrum was equally clean, and the carbene carbon resonance appeared at 192.0 ppm, a characteristic value for these complexes. $^1$H NMR (400 MHz, Dichloromethane-d$_2$) δ ppm 0.90 (d, J=6.64 Hz, 6 H, CHMe$_2$), 1.29 (d, J=6.64 Hz, 6 H, CHMe$_2$), 1.92 (s, 9 H, C$_3$H$_9$), 3.24 (septet, J=6.64 Hz, 2 H, CH), 6.85 (d, J=2.34 Hz, 1 H, CH), 7.06 (d, J=8.20 Hz, 2 H, CH), 7.17 (t, J=7.60 Hz, 1 H, CH), 7.24-7.30 (m, 3 H), 7.38 (t, J=7.80 Hz, 2 H, CH), 7.49 (t, J=7.40 Hz, 1 H, CH). $^{13}$C NMR (101 MHz, Dichloromethane-d$_2$) δ ppm 24.1 (CHMe$_2$), 26.4 (CHMe$_2$), 28.5 (CHMe$_2$), 31.6 (C(CH$_3$)$_3$), 61.2 (C(CH$_3$)$_3$), 120.1, 120.8, 124.7, 127.9, 128.3, 128.9, 129.5, 132.6, 141.5, 142.7, 163.7 (imine), 191.9 (carbene). Anal. Calculated for C$_{26}$H$_{33}$N$_3$Cl$_4$Zr: C, 50.32; H, 5.36; N, 6.77. Found C, 50.01; H, 5.28; N, 6.83. A $^1$H NMR spectrum of Zr-complex 13 is shown in FIG. 6.

Following the procedures discussed above and illustrated in Scheme 10, a Ti analog 14 to Zr-complex 13 was produced. Ti-complex 14 was isolated as a crystalline yellow solid in 27% yield. $^1$H NMR (400 MHz, Dichloromethane-d$_2$) δ ppm 0.91 (d, J=6.64 Hz, 6 H, CHMe$_2$), 1.32 (d, J=6.64 Hz, 6 H, CHMe$_2$), 1.96 (s, 9 H, C$_3$H$_9$), 3.30 (spt, J=6.64 Hz, 2 H, CH), 6.78 (d, J=2.34 Hz, 1 H, CH), 7.05 (d, J=7.80 Hz, 2 H, CH), 7.16 (t, J=7.60 Hz, 1 H, CH), 7.23-7.31 (m, 3 H) 7.38 (t, J=7.80 Hz, 2 H, CH), 7.48 (t, J=7.40 Hz, 1 H, CH). $^{13}$C NMR (101 MHz, Dichloromethane-d$_2$) δ ppm 24.1 (CHMe$_2$), 26.7 (CHMe$_2$), 28.7 (CHMe$_2$), 31.5 (C(CH$_3$)$_3$), 62.5 (C(CH$_3$)$_3$), 118.8, 120.0, 124.6, 128.0, 128.2, 128.9, 129.2, 132.4, 141.6, 144.8, 161.0, 194.9. Anal. Calculated for C$_{26}$H$_{33}$N$_3$Cl$_4$Ti: C, 54.10; H, 5.76; N, 7.28. Found C, 49.05; H, 5.28; N, 7.08.

Example 6

Synthesis of Compounds of Formula (I)

Using procedures analogous to those described above, Zr-complex 15 was produced. See Scheme 12 below.

Scheme 12

The ligand precursor 14 was synthesized by reaction of the iminoyl chloride 13 and tert-butyl imidazole. Unexpectedly, this synthesis required only 2 hours for completion at 60° C. The Zr complex 15 was isolated as an off white crystalline solid in 42% yield. $^1$H NMR (400 MHz, Dichloromethane-d$_2$) δ ppm 1.92 (s, 9 H, C$_3$H$_9$) 6.82 (d, J=2.34 Hz, 1 H, CH) 7.06-7.16 (m, 3 H) 7.19-7.32 (m, 5 H) 7.41 (s, 2 H, CH) 7.44-7.52 (m, 1 H). $^{13}$C NMR (101 MHz, Dichloromethane-d$_2$) δ ppm 31.8, 61.7, 119.4, 120.4, 124.6, 127.0, 127.9, 128.7, 128.9, 129.3, 132.1, 146.8, 163.3 (imine), 193.1 (carbene). Crystals suitable for X-ray analysis were grown by diffusing pentane into a concentrated dichloromethane solution of the compound. The crystal structure of Zr complex 15 was determined and found to have features similar to the analogous compounds shown in FIGS. 3-5.

Example 7

Synthesis of Compounds of Formula (VII)

Figure 7:
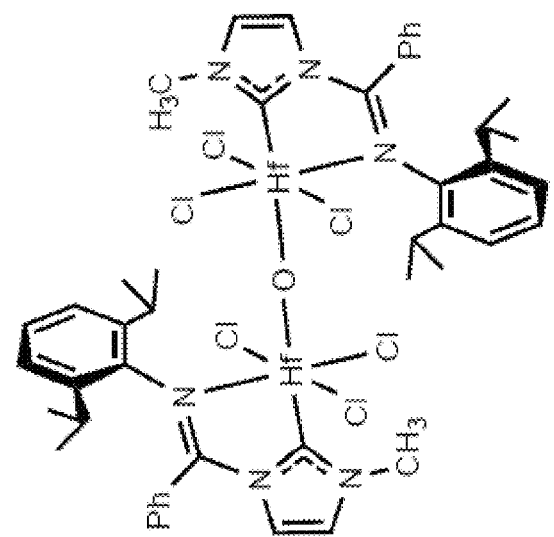
FIG. 7 illustrates the crystal structure of the Hf-oxo dimer compound 24 of Example 7.
Figure 7:
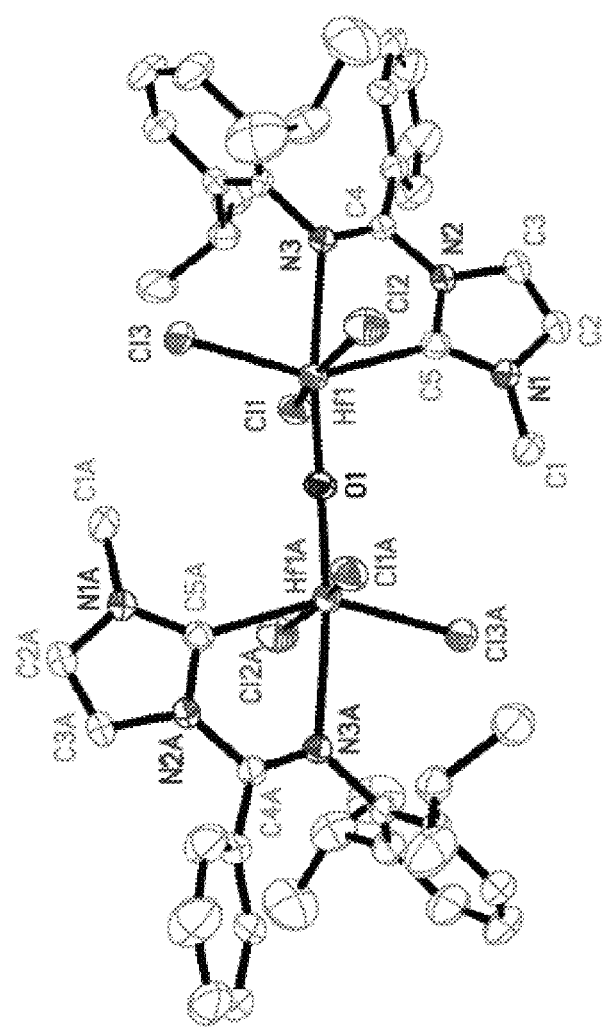

In the course of various attempts to crystallize Hf-complex 4 of Example 3, a surprising structure resulted: a hafnium-oxo dimer compound 24 having formula (VII). It is believed that the dimer may have been produced from a hydrolysis reaction that occurred during crystallization due to the presence of a small amount of water. The crystal structure for Hf-dimer compound 24 is illustrated in FIG. 7.

The Ti-complex 14 of Example 5 also was hydrolyzed to form an oxo-bridged dimer compound 34 having formula (VII). Again, Applicants believe that the Ti-dimer compound 34 may have been produced in a hydrolysis reaction due to the presence of small amounts of water.

Example 8

Synthesis of Compounds of Formula (IV)

Figure 8:
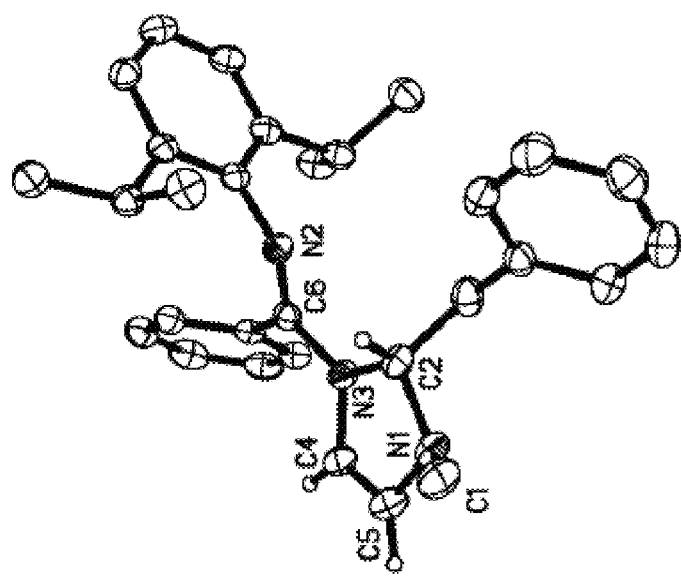
FIG. 8 illustrates the crystal structure of compound 3a of Example 8.

Precursor compounds 1a and 1b were reacted with $Hf(CH_2Ph)_4$ and $Zr(CH_2Ph)_4$ (see Scheme 16 below). Initial studies indicated reaction products having $^1H$ NMR data that appeared consistent with benzyl insertion and ligand coordination to give 2a and 2b. However, isolation of a product from the reaction of 1a and $Hf(CH_2Ph)_4$ in benzene and subsequent crystallographic analysis revealed an unexpected outcome (compound 3a). While not intending to be bound by theory, Applicants believe that, rather than benzyl insertion into the imine bond of the ligand precursor, there may have been an attack of a benzyl group at the imidazolium carbon; the imidazole hydrogen was not deprotonated to provide the carbene as anticipated, and there was no coordination to metal. The air stable, organic product 3a was purified, isolated, and characterized, and a high quality crystal structure was obtained, as illustrated in FIG. 8. NMR tube reactions indicated similar products when the analogous benzylimidazole ligand precursor 1b was used, as well as for reactions with $Zr(CH_2Ph)_4$. The $M(CH_2Ph)_xCl_{4-x}$ species remaining in solution may have provided the benzyl $^1H$ NMR resonances that erroneously indicated that 2a and 2b had been formed.

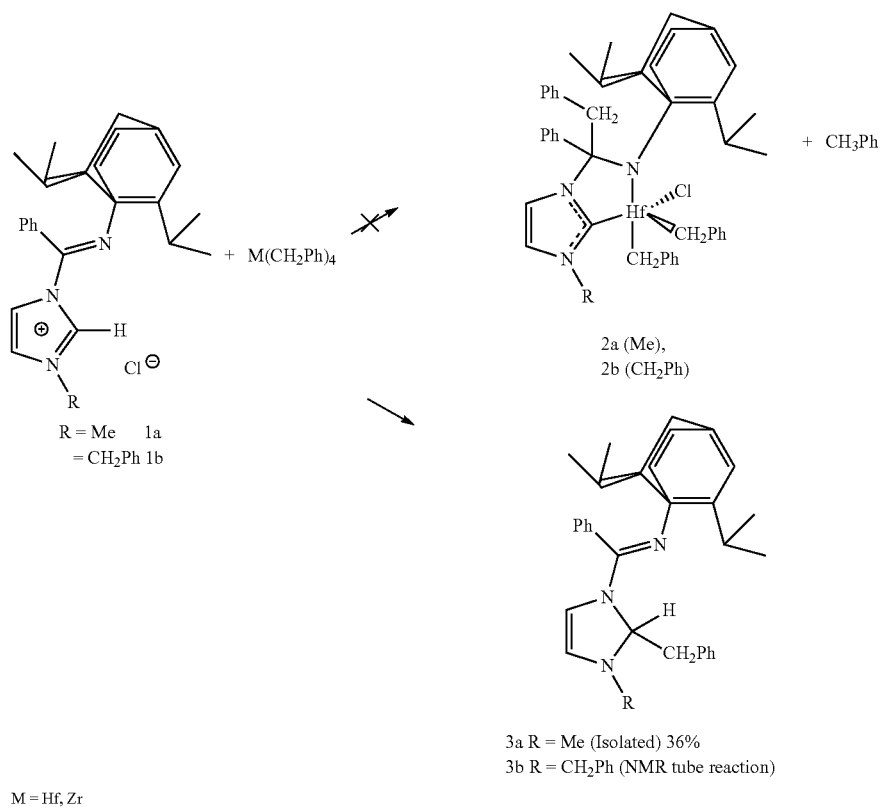

Scheme 16

Figure 9:
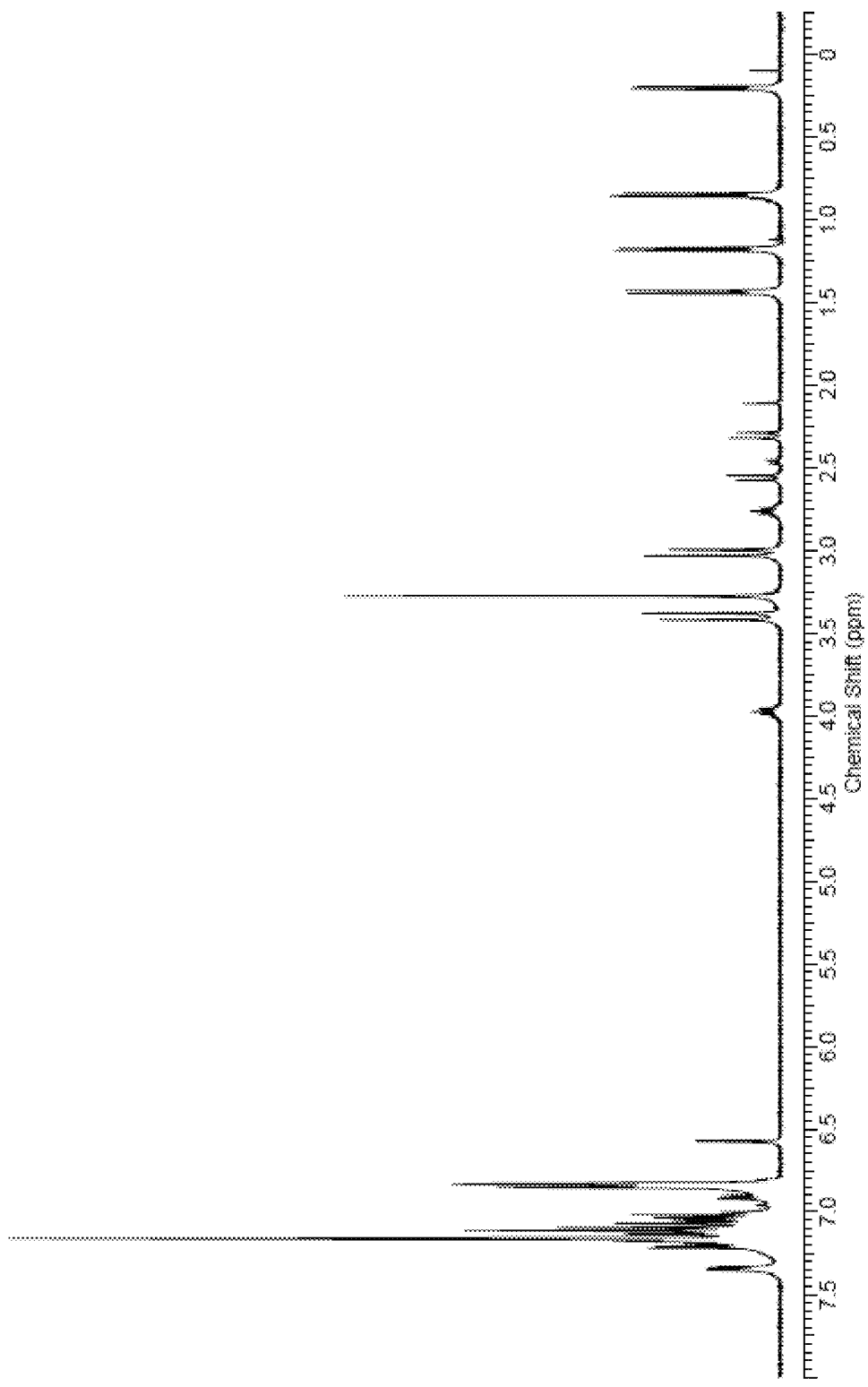
FIG. 9 presents a $^1$HNMR spectrum of Hf-complex 16a of Example 8.

As summarized in Scheme 17 below, compound 16a was synthesized as follows. The imidazolium chloride 1a (0.24 g, 0.63 mmol) and potassium hexamethyldisilazide (0.132 g, 0.66 mmol) were stirred in 20 mL of benzene for 30 min. Then, tetrabenzylhafnium (0.34 g, 0.63 mmol) was carefully added to this solution in one portion, and the mixture was stirred for 24 hr at room temperature. Next, benzene was removed in vacuo, and the crude material was dissolved in pentane and filtered through celite to remove KCl. The filtrate was concentrated, and the bright red precipitate was filtered, resulting in Hf-compound 16a (0.15 g, 27% yield). $^1H$ NMR (400 MHz, Benzene-$d_6$) δ ppm 0.20 (d, J=6.64 Hz, 3 H, $CH_3$), 0.85 (d, J=6.64 Hz, 3 H, $CH_3$), 1.18 (d, J=6.64 Hz, 3 H, $CH_3$), 1.43 (d, J=6.64 Hz, 3 H, $CH_3$), 2.30 (d, J=12.10 Hz, 1 H, $CH_2Ph$), 2.56 (d, J=12.10 Hz, 1 H, $CH_2Ph$), 2.76 (septet, J=6.64 Hz, 1 H, CH), 3.01 (d, J=14.44 Hz, 3 H, $CH_2Ph$), 3.27 (s, 3 H, $CH_3$-imidazole), 3.40 (d, J=14.44 Hz, 3 H, $CH_2Ph$), 3.97 (septet, J=6.64 Hz, 1 H, CH), 6.45-7.51 (m, 30 H). $^{13}C$ NMR (101 MHz, Benzene-d$_6$) δ ppm 24.3, 24.9, 25.1, 25.3, 28.0, 28.3, 37.9, 40.7, 76.4, 82.9, 106.9, 122.1, 124.9, 125.1, 126.1, 126.4, 127.3, 128.4, 128.5, 129.7, 130.2, 130.8, 140.1, 140.3, 142.5, 143.4, 144.0, 147.6, 164.1. Anal. Calculated for C$_{51}$H$_{55}$N$_3$Hf: C, 68.94; H, 6.24; N, 4.73. Found C, 66.13; H, 6.21; N, 2.99. A $^1$H NMR spectrum of Hf-complex 16a is shown in FIG. 9.

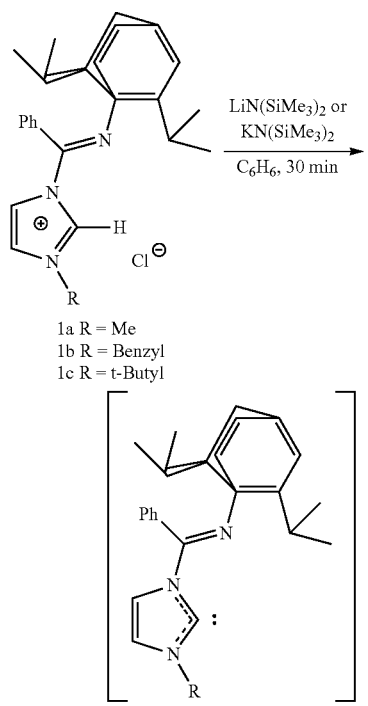

Scheme 17

Figure 10:
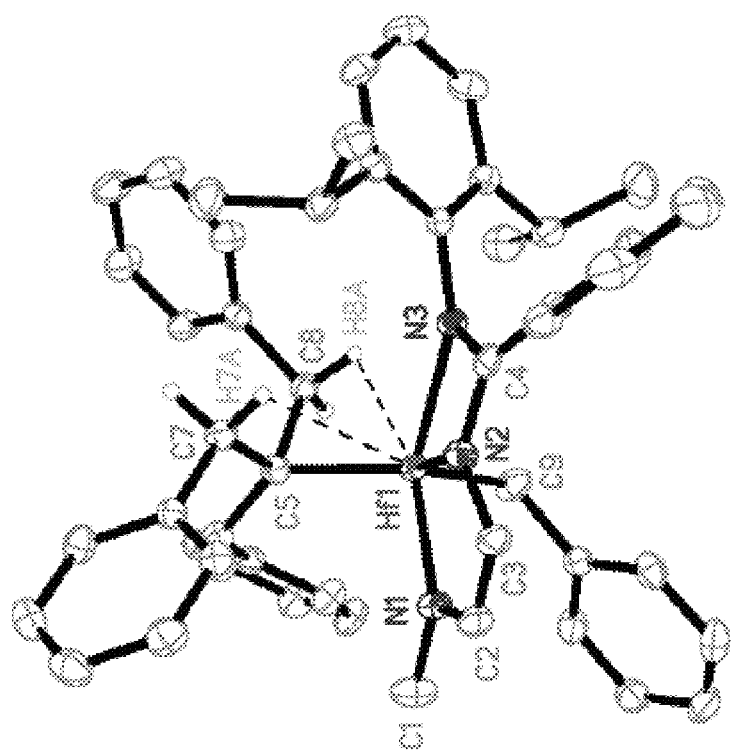
FIG. 10 illustrates the crystal structure of Hf-complex 16a of Example 8.

Surprisingly, structural confirmation by X-ray crystallography revealed an unexpected product, one that resulted from decarbonization of the carbene carbon to give the dianionic imino-enediamide chelate compound 16a of Formula (IV). This product formed by successive insertion of three benzyl ligands into the carbene moiety. There was no benzyl insertion into the imine, and the carbene carbon ended up in a newly formed tribenzyl methyl ligand. The crystal structure for compound 16a is shown in FIG. 10. X-ray quality crystals were grown by dissolving the product in pentane and cooling to –35° C.

Hf-compound 16a also was synthesized using lithium hexamethyldisilazide, instead of potassium hexamethyldisilazide. A bright red precipitate was isolated Further, crystals of Hf-compound 16a that were suitable for X-ray analysis were grown by cooling a concentrated pentane solution of the compound to –35° C.

Figure 11:
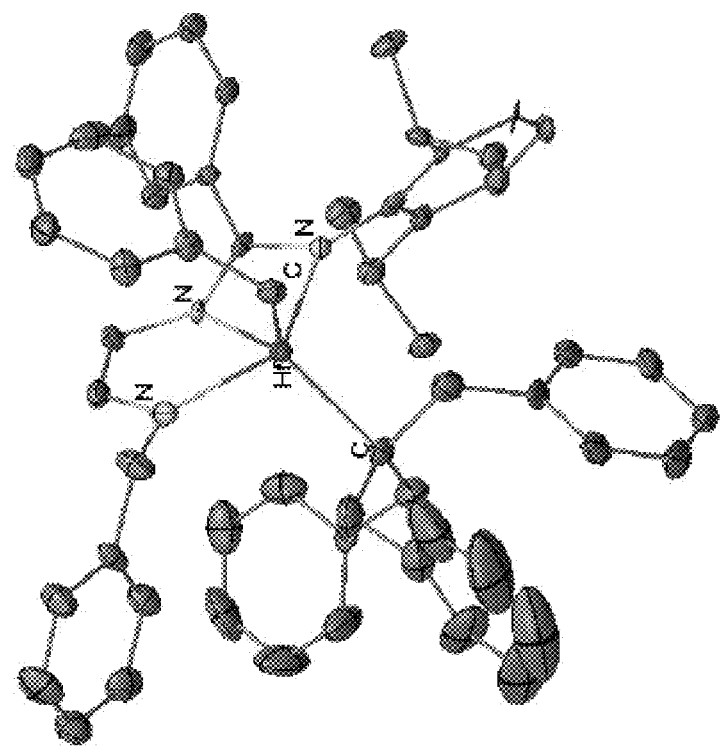
FIG. 11 illustrates the crystal structure of Hf-complex 16b of Example 8.

Analogous Hf-compound 16b, with a benzyl group instead of a methyl group, was produced in a manner to complex 16a, as shown in Scheme 17. The yield was 25%. Crystals of Hf-compound 16b were grown by cooling a concentrated pentane solution of the complex to –35° C. The crystal structure of 16b is shown in FIG. 11.

Analogous Hf-compound 16c, with a t-Bu group instead of a methyl or benzyl group, was produced in a manner to complex 16a, as shown in Scheme 17. Compound 16c was confirmed by $^1$H NMR. Interestingly, the reaction appeared to be complete within 2 hr for compound 16c, compared with 24 hr for the less bulky analogues 16a and 16b.

Example 9

Tridentate Chelates with Three Different Donors, Used as Precursors for Compounds of Formula (III)

One objective of Example 9 was to prepare a tridentate chelate with two anionic groups that would easily give rise to a (chelate)M(alkyl)$^+$ cation upon activation with methylaluminoxane (MAO), for instance, in parallel to many successful metallocene-based catalyst systems. Imino-keto-imidazolium salt 5, which can be a precursor for compounds of formula (III), was prepared as shown in Scheme 20. $^1$H NMR indicated that the product was not pure and formed in somewhat low yield. Compounds of formula (III) can be synthesized from precursor 5 by further conducting the metalation reaction illustrated in Examples 3-6 above.

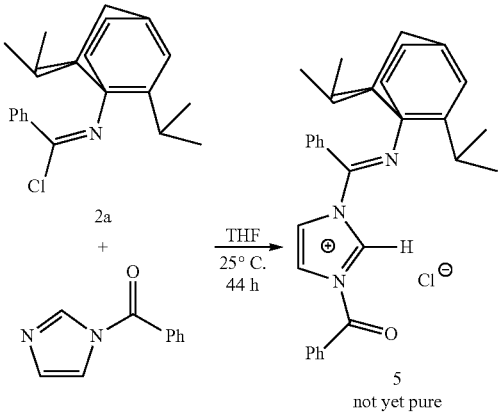

Scheme 20

Example 10

Synthesis of Compounds of Formula (V)

A bis-imidazole ligand precursor 11 was synthesized from mesitylimidazole in 91% yield following the procedure of Scheme 22 below.

Scheme 22

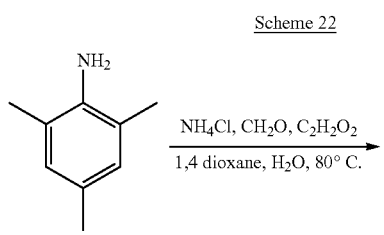

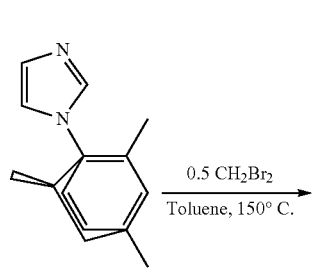

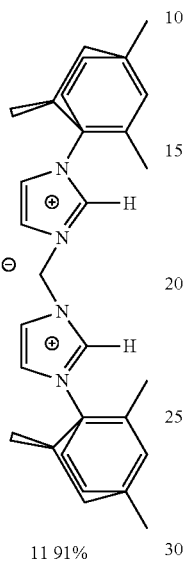

11 91%

A free bis-carbene 12 was synthesized after reaction with potassium t-butoxide in THF (see Scheme 23 below). Applicants found that this base gave a significantly higher yield and a cleaner reaction relative to other materials, such as silylamides or potassium hydride. Compound 12 appeared to be air/moisture sensitive; therefore, the reaction was conducted using swivel-frit techniques and stored in a glove box refrigerator. Moreover, Applicants found that removing all traces of THF was beneficial for obtaining a pure compound. The free carbene was then treated with $ZrCl_4(THF)$, in benzene. Only 30 min were required for complete consumption of starting materials. Compound 13 (having formula (V)) precipitated from solution during the reaction. $^1H$ NMR spectra were consistent with the formation of compound 13.

Scheme 23

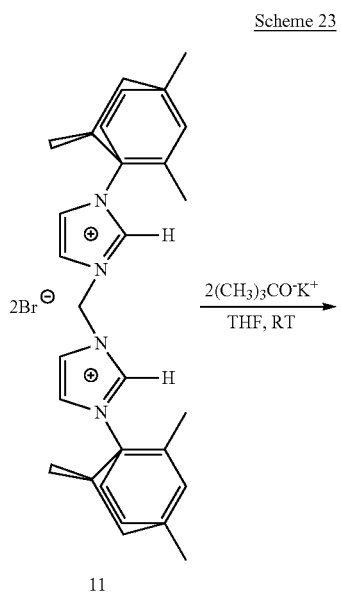

11

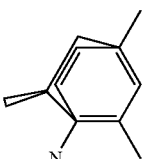

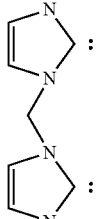

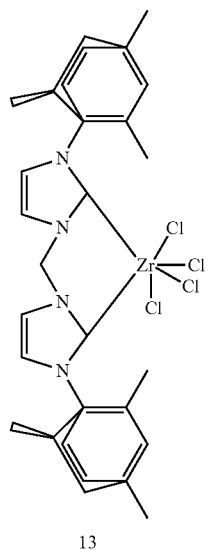

12 68%    13

The Zr-complex 13 was synthesized in a yield of about 67%. In like manner, a Hf-complex 14, synthesized similarly to that of the Zr-complex 13, was produced in a yield of about 53%.

Example 11

Imino Imidazolium Cations with Reduced Steric Bulk at $R^1$, Used as Precursors of Compounds of Formula (I)

An objective of Example 11 was to reduce the steric bulk at the imine carbon (e.g., $R^1$=Me, instead of $R^1$=Ph). It is believed that this may improve the tolerance of bulky groups on the carbene nitrogen substituents, and may reduce the kinetic barrier for insertion or attack at the imine carbon, thereby leading to derivatives with anionic ligands.

Amidocarbene chelate ligands were prepared following the synthesis shown in Scheme 26. Acetylation of diisopropylaniline 2 by direct reaction of diisopropylaniline with acetic anhydride gave acetamide product 3 in almost quantitative yield. Imidoyl chloride 4 was prepared from the reaction of acetamide 3 with PCl5. The α-iminoimidazolium salt 5 (a desired ligand precursor for compounds of formula (I)) was obtained from the reaction of the imidoyl chloride with 1-methylimidazole. Two analogues with greater steric bulk at the carbene N-substituent, 6 and 7, were prepared similarly from tert-butylimidazole and 2,6-diisopropylphenylimidazole, respectively.

Scheme 26

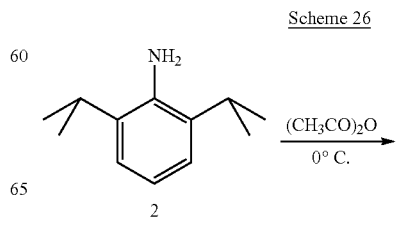

2

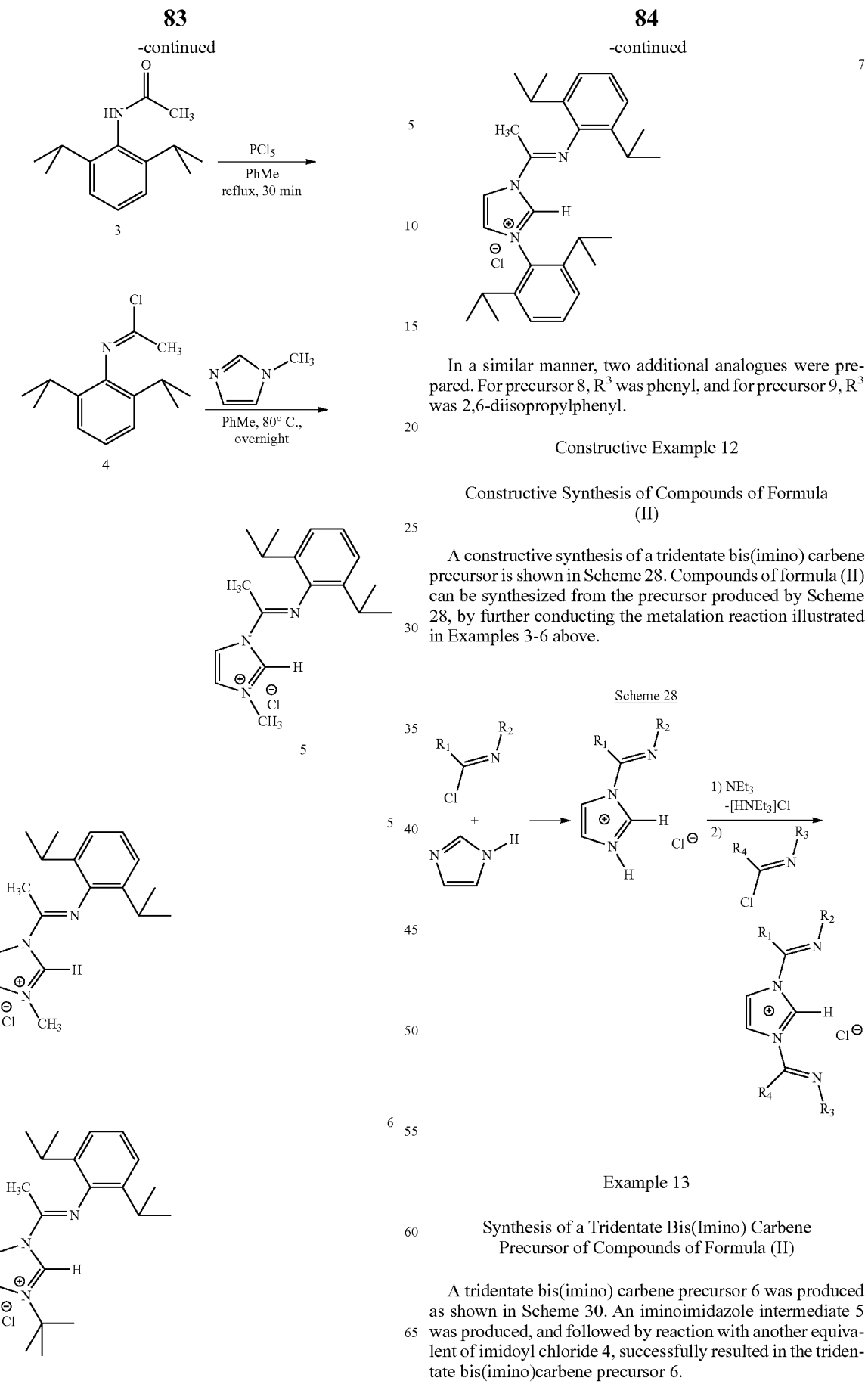

In a similar manner, two additional analogues were prepared. For precursor 8, $R^3$ was phenyl, and for precursor 9, $R^3$ was 2,6-diisopropylphenyl.

Constructive Example 12

Constructive Synthesis of Compounds of Formula (II)

A constructive synthesis of a tridentate bis(imino) carbene precursor is shown in Scheme 28. Compounds of formula (II) can be synthesized from the precursor produced by Scheme 28, by further conducting the metalation reaction illustrated in Examples 3-6 above.

Example 13

Synthesis of a Tridentate Bis(Imino) Carbene Precursor of Compounds of Formula (II)

A tridentate bis(imino) carbene precursor 6 was produced as shown in Scheme 30. An iminoimidazole intermediate 5 was produced, and followed by reaction with another equivalent of imidoyl chloride 4, successfully resulted in the tridentate bis(imino)carbene precursor 6.

Scheme 30

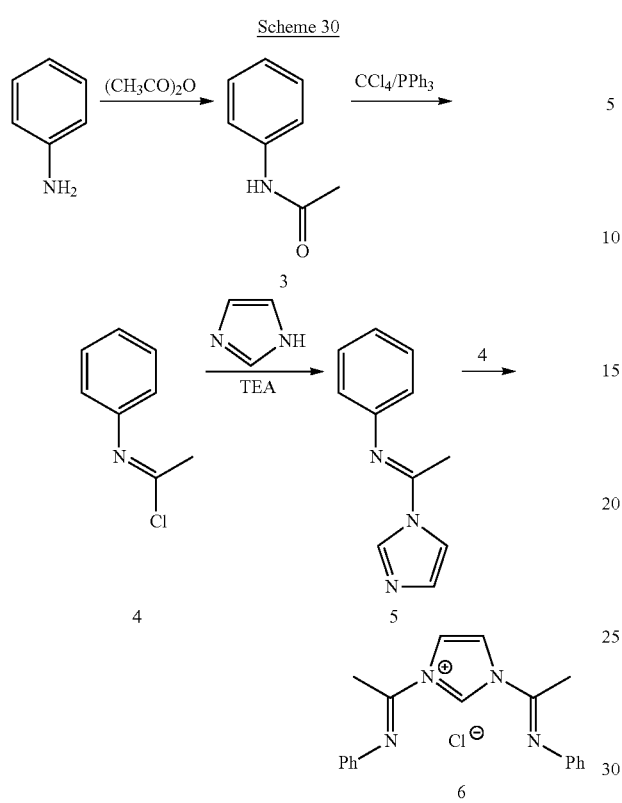

Example 14

Metalation of Bidentate Iminocarbene Precursors

In Scheme 32 (below), compounds 1a and 1b have methyl groups at the imine carbon, phenyl at the imine nitrogen, and either methyl (1a) or t-Bu (1b) on the imidazole nitrogen. Zr(CH$_2$Ph)$_4$ in THF was added at −78° C., then the mixture was allowed to slowly warm to room temperature with overnight stirring. Then, THF was removed under vacuum. For the reaction of 1b and Zr(CH$_2$Ph)$_4$, the resulting residue was a foamy solid, but $^1$H NMR spectra in C$_6$D$_6$ were consistent with the metalated product 2b. It was proposed that metalation of two ligands occurred on the basis of the reaction stoichiometry, although there were some unidentified side products. A significant amount of THF was detected in the spectra, suggesting coordination to the metal.

Scheme 32

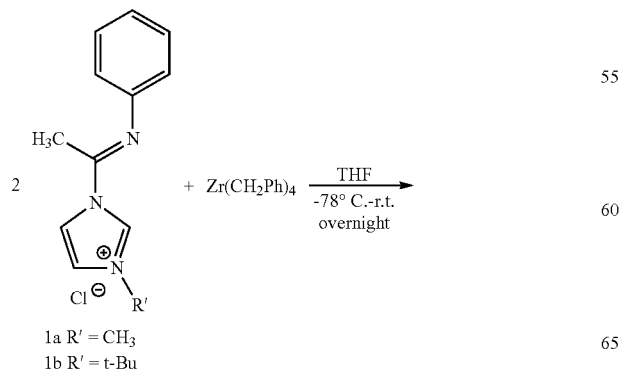

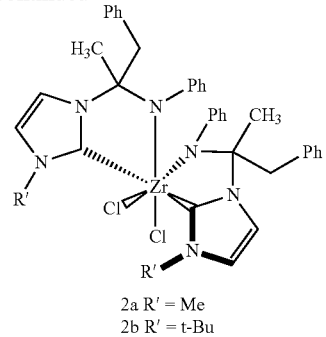

2a R' = Me
2b R' = t-Bu

Example 15

Polymerization Experiments with Compounds of Formula (I) and (IV)

In Example 15, imino carbene compounds/derivatives with the following structures were evaluated in olefin polymerizations:

A
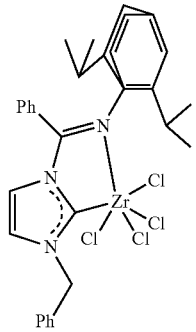

B
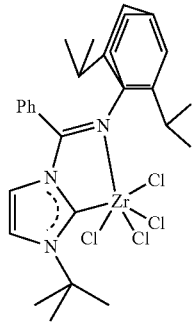

C
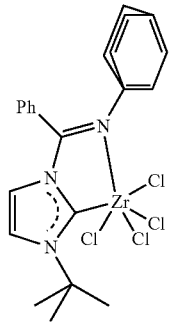

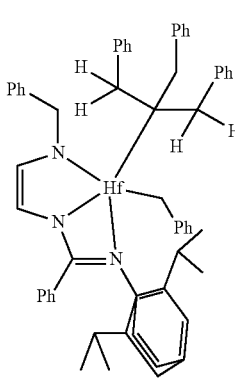

D

Figure 12:
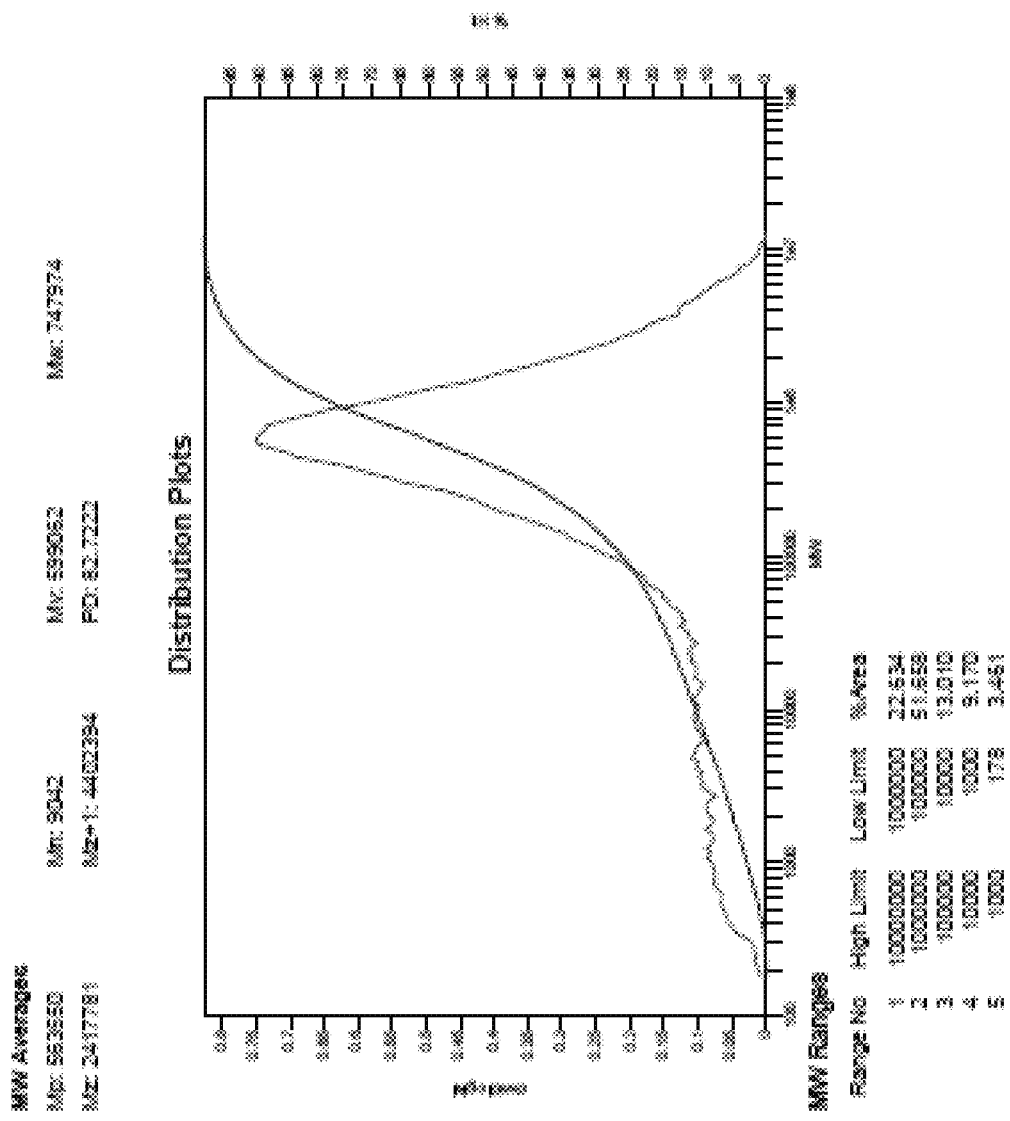
FIG. 12 presents a plot of the molecular weight distribution of the polymer of Example 15 produced using catalyst B.
Figure 13:
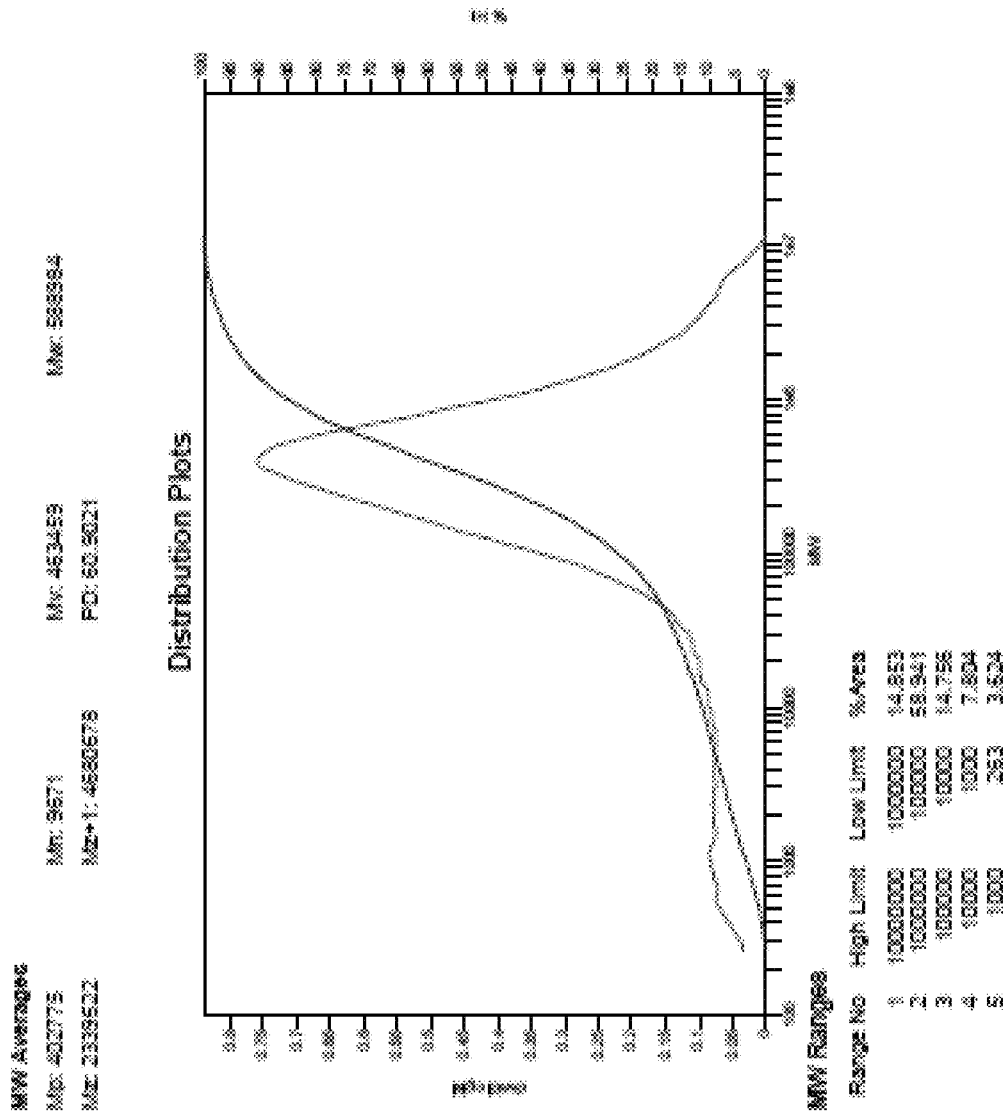
FIG. 13 presents a plot of the molecular weight distribution of the polymer of Example 15 produced using catalyst D.
Figure 14:
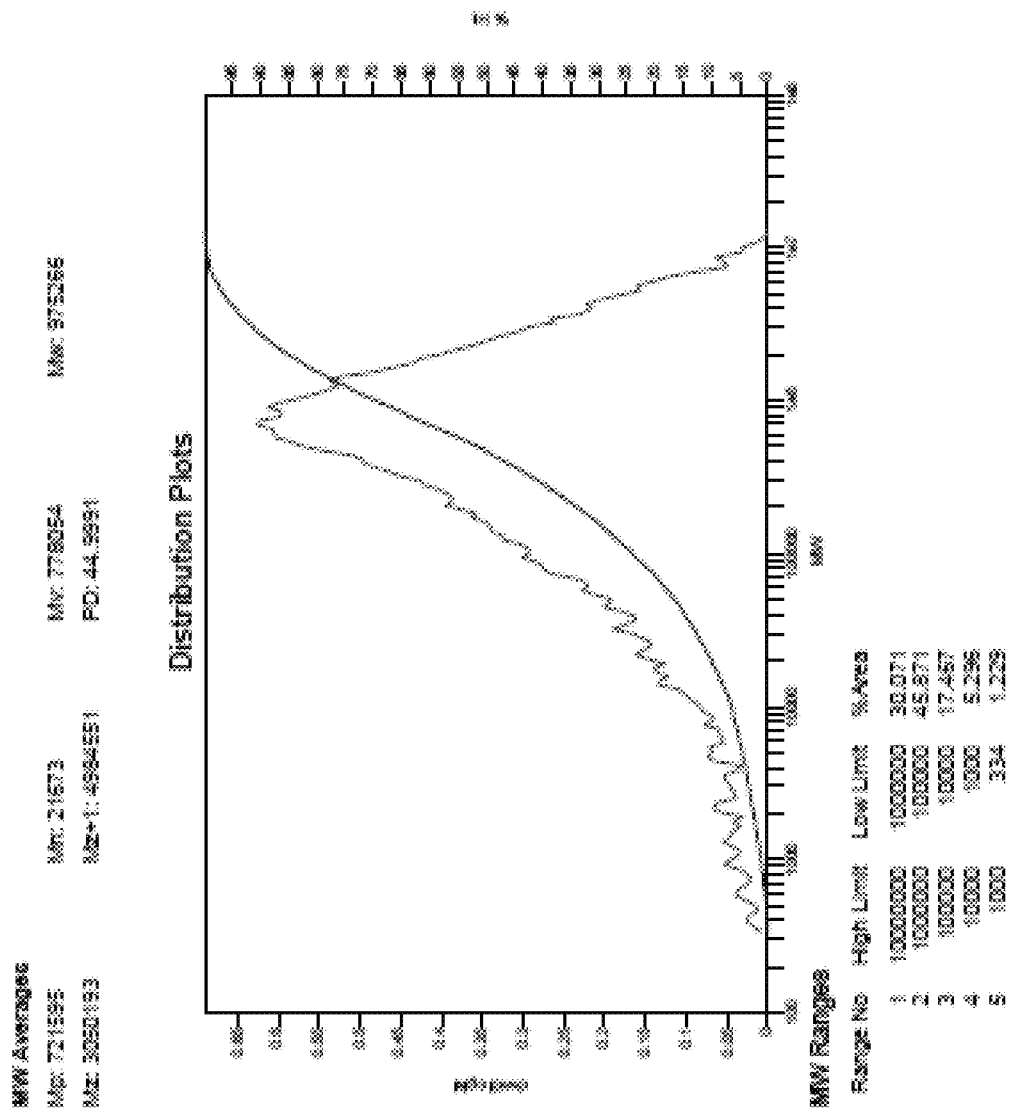
FIG. 14 presents a plot of the molecular weight distribution of the polymer of Example 15 produced using catalyst C.

As shown in Table 1, catalyst activities ranged over more than an order of magnitude. The polymerization conditions were 1 mg of catalyst charged to a Fischer-Porter-bottle, initiated with MAO under $C_2H_4$ pressure to form a pre-polymer, and then transferred to a reactor at 80° C. Replacement of the benzyl group of A with tert-butyl in B resulted in a large increase in activity. The variability seen for the four trials with B likely may reflect errors in weighing the toluene-insoluble material, or possibly inconsistencies in pre-polymerization. Surprisingly, reducing the steric bulk at the imine nitrogen gave the catalyst C the highest activity in terms of total g PE formed. Catalyst D showed comparably high activity to B and C; in fact, it had the highest activity when expressed in units of Kg PE/(mol catalyst·psi). Molecular weight distribution data is provided in Table 2. The molecular weight distribution plot for the polymer produced using catalyst B is shown in FIG. 12, the molecular weight distribution plot for the polymer produced using catalyst D is shown in FIG. 13, and the molecular weight distribution plot for the polymer produced using catalyst C is shown in FIG. 14. The polymers produced using catalysts B, C, and D had very broad molecular weight distributions, as measured by Mw/Mn, ranging from 45 to 83.

TABLE 1

| Catalyst | Trial | psi $C_2H_4$ | g PE | Activity, Kg PE/(mol catalyst · psi) |
|---|---|---|---|---|
| A | 1 | 450 | 0.5 | 0.7 |
| B | 1 | 450 | 4.2 | 5.8 |
| B | 2 | 450 | 7.4 | 10 |
| B | 3 | 450 | 8.2 | 11 |
| B | 4 | 450 | 3.3 | 4.5 |
| C | 1 | 550 | 10.9 | 10.6 |
| D | 1 | 550 | 6.6 | 12 |

TABLE 2

| Structure-trial | grams of PE | Mn/1000 | Mw/1000 | Mz/1000 | Mv/1000 | Mp/1000 | Mw/Mn |
|---|---|---|---|---|---|---|---|
| B-trial 3 | 8.2 | 9.0 | 748 | 2418 | 599 | 564 | 83 |
| D-trial 1 | 6.6 | 9.7 | 589 | 2340 | 463 | 403 | 61 |
| C-trial 1 | 10.9 | 21.7 | 975 | 3050 | 778 | 722 | 45 |

Imino carbine compounds/derivatives C and D were evaluated further in a catalyst composition with a sulfated alumina activator-support, which was prepared as follows. Bohemite was obtained from W.R. Grace Company under the designation "Alumina A" and having a surface area of about 300 m²/g and a pore volume of about 1.3 mL/g. This material was obtained as a powder having an average particle size of about 100 microns. This material was impregnated to incipient wetness with an aqueous solution of ammonium sulfate to equal about 15% sulfate. This mixture was then placed in a flat pan and allowed to dry under vacuum at approximately 110° C. for about 16 hours. To calcine the resultant powdered mixture, the material was fluidized in a stream of dry air at about 550° C. for about 6 hours. Afterward, the sulfated alumina was collected and stored under dry nitrogen, and was used without exposure to the atmosphere.

These polymerizations were conducted in a one-gallon stainless steel semi-batch reactor. Two liters of isobutane and alkyl aluminum co-catalyst were used in the polymerization experiments. The typical polymerization procedure was conducted as follows: alkyl aluminum, the activator-support, and the catalyst were added in order through a charge port while venting isobutane vapor. The charge port was closed and about two liters of isobutane were added. The contents of the reactor were stirred and heated to the desired run temperature, and ethylene was then introduced. Ethylene was fed on demand to maintain the specified pressure for the specified length of the polymerization run. The reactor was maintained and controlled at the desired run temperature throughout the polymerization. Upon completion, the ethylene flow was stopped and the reactor pressure slowly vented off. The reactor was opened and the polymer product was collected and dried under vacuum at approximately 50° C. for at least two hours.

The respective catalyst was charged to the reactor with 100 mg sulfated alumina and 0.5 mmol triisobutylaluminum (TIBA). The polymerization temperature was 80° C. Catalyst C was treated with 9-BBN (9-borabicyclononane) in toluene for 3 days, and the resultant turbid solution was added to the reactor with the sulfated alumina and TIBA. The results of these polymerization experiments are summarized in Table 3.

TABLE 3

| Catalyst | mg | psi $C_2H_4$ | g PE | Activity, Kg PE/(mol catalyst · psi) |
|---|---|---|---|---|
| C | 1.0 | 550 | 5.7 | 5.5 |
| C | 2.0 | 550 | 6.5 | 3.1 |
| C | 1.8 | 450 | 4.2 | 2.7 |
| D | 2.0 | 550 | 0.5 | 0.9 |

Example 16

Precursors for Compounds of Formula (I) with Fluorinated Aryl Groups

Scheme 34 summarizes the procedure used to produce precursor 6. First, 4-(trifluoromethyl)benzoic acid was reacted with excess $SOCl_2$, followed by vacuum distillation, forming the pure acid chloride 3 as a colorless liquid in 93% yield. The acid chloride 3 was then reacted with 2,6-diisopropyl aniline in the presence of triethylamine in dry dichloromethane (DCM) to obtain the anilide compound 4, which was recrystallized in toluene to form a white crystalline solid (55% yield). The corresponding imidoyl chloride 5 was then produced by reacting the anilide compound 4 with excess SOCl₂. The imidoyl chloride 5 was obtained after recrystallization from pentane as a pale yellow solid in 85% yield. The precursor with the fluorinated aryl group 6 was produced by reacting the imidoyl chloride 5 with 1.1 equivalents of 1-methyl imidazole in dry THF under N₂ for 2 days, then recrystallizing with DCM/Et₂O to produce the pale yellow solid precursor 6 in 70% yield.

Scheme 34

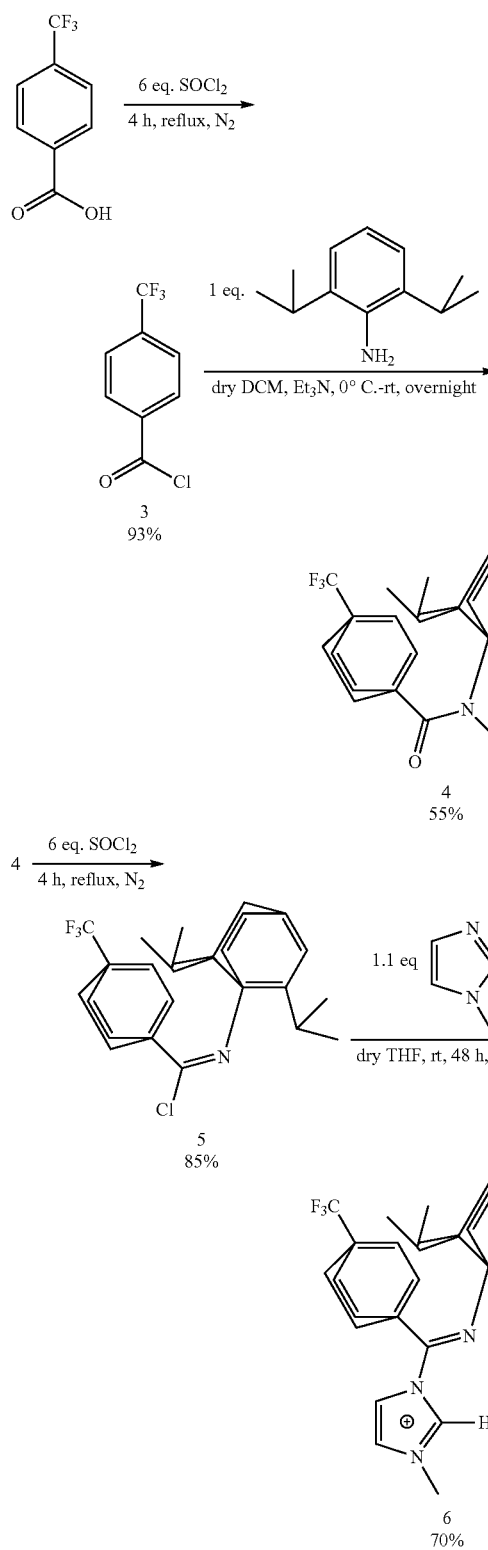

Example 17

Synthesis of Compounds of Formula (I) with Fluorinated Aryl Groups

Using the procedure shown in Scheme 36, pale yellow compound 8 was prepared in 37% yield. The ligand precursor 6 was reacted with KN(SiMe₃)₂ (abbreviated KHMDS in Scheme 36) in C₆H₆, forming a brownish turbid mixture. ZrCl₄-THF was then added in a single portion, and stirred for 2 hours at room temperature, forming a precipitate. The yellowish white precipitate was filtered, reduced in volume under vacuum, and washed twice with benzene and once with pentane. To remove residual solvent, the precipitate was dried for another 4 hours under vacuum. The precipitate was then dissolved in dry dichloromethane and filtered twice through Celite® 540 followed by a glass microfiber filter to remove KCl. Finally, the filtrate was concentrated under vacuum, and the desired compound 8 was obtained by slow diffusion of layered pentane into the dichloromethane solution.

Figure 15:
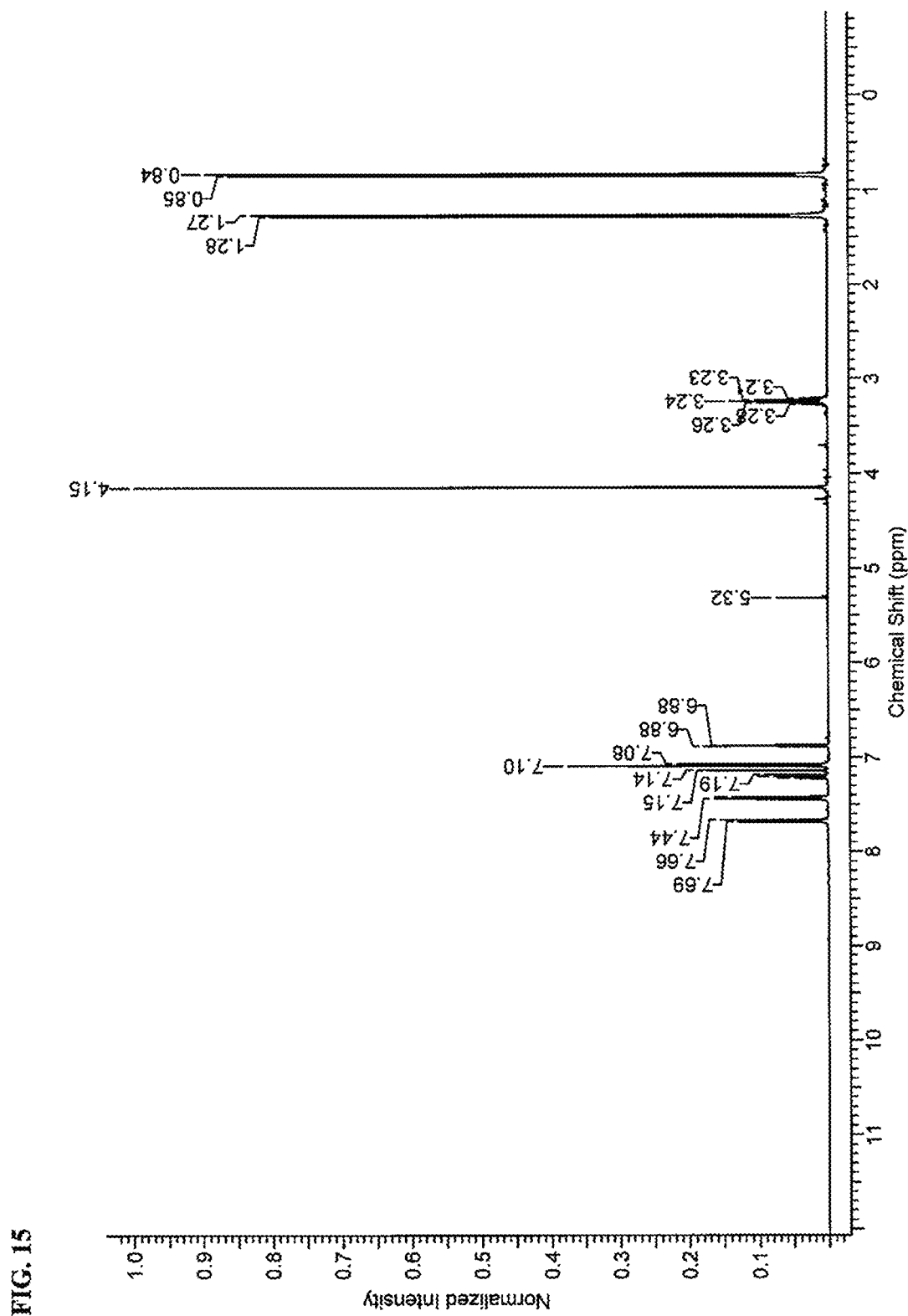
FIG. 15 presents a $^1$H NMR spectrum of Zr-complex 8 of Example 17.
Figure 16:
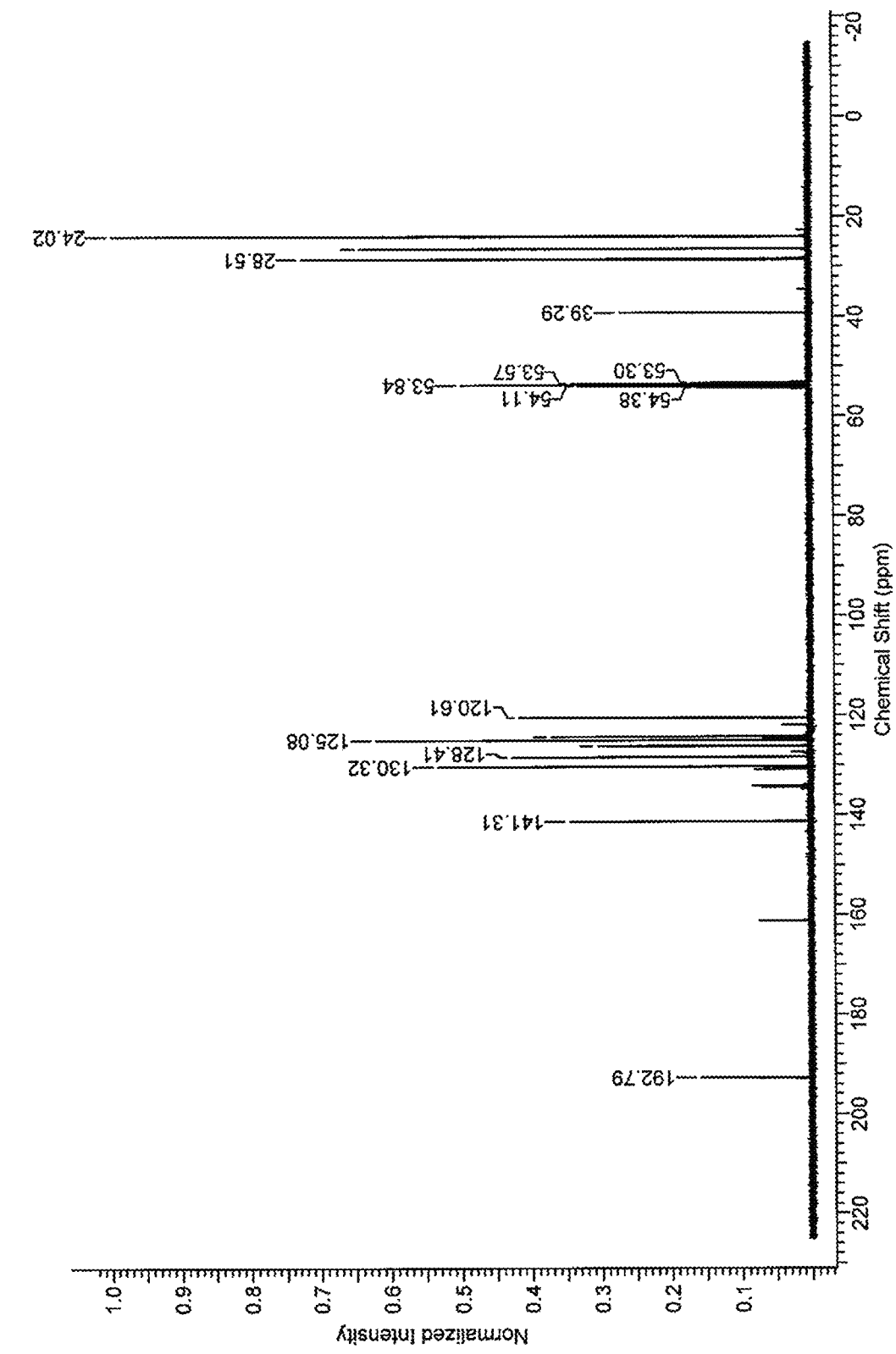
FIG. 16 presents a $^{13}$C NMR spectrum of Zr-complex 8 of Example 17.

A ¹NMR and a ¹³C NMR spectrum (in CD₂Cl₂) of Zr-complex 8 are shown in FIG. 15 and FIG. 16, respectively.

Scheme 36

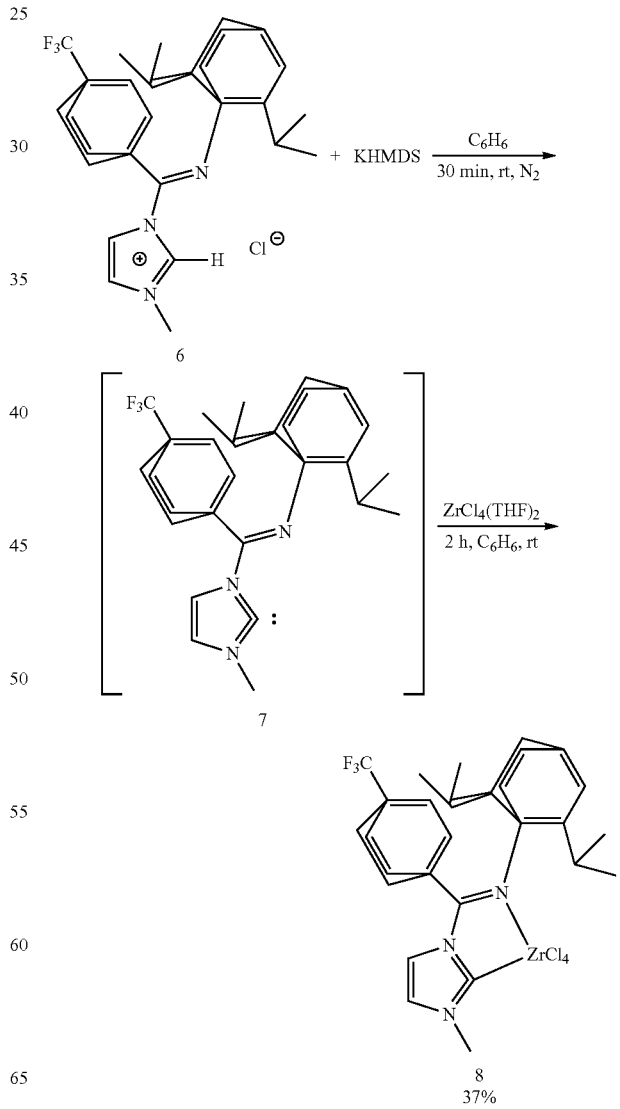

Example 18

Polymerization Experiments with Compounds of Formula (I)

In Example 18, the imino carbene compound 8 from Example 17 was evaluated in olefin polymerizations. These experiments were conducted in a manner similar to the experiments summarized in Table 3 of Example 15, using a one gallon reactor, a polymerization temperature of 90° C., and a reaction time of 1 hr. Triisobutylaluminum was first charged to the reactor, followed by the sulfated alumina activator-support, and then 1 mg of the imino carbine compound 8. The results of these polymerization experiments are summarized in Table 4. An increase in the amount of sulfated alumina and an increase in the ethylene pressure resulted in a twofold increase in the activity of the catalyst system.

TABLE 4

| Catalyst | mg support | psi C$_2$H$_4$ | g PE | Activity, Kg PE/(mol catalyst · psi) |
|---|---|---|---|---|
| 8 | 158 | 389 | 0.25 | 0.42 |
| 8 | 605 | 550 | 0.89 | 1.04 |

We claim:

1. A compound having the formula:

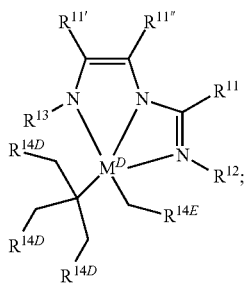

(IV-B)

or a partially saturated or saturated version thereof; wherein:
M$^D$ is Ti, Zr, or Hf;
R$^{11}$, R$^{11'}$, R$^{11''}$, R$^{12}$, and R$^{13}$ are independently H or a hydrocarbyl, hydrocarbyloxide, hydrocarbylamino, hydrocarbylsilyl, or halogenated hydrocarbyl group, any of which having up to 18 carbon atoms; and
R$^{14D}$ and R$^{14E}$ are phenyl groups.

2. The compound of claim 1, wherein:
R$^{11'}$ and R$^{11''}$ are H; and
R$^{11}$, R$^{12}$, and R$^{13}$ are independently H, Me, t-Bu, Ph, CH$_2$-Ph, 2,4,6-trimethylphenyl, 2,6-dimethylphenyl, 2,6-diisopropylphenyl, trifluoromethyl, pentafluorophenyl, or 4-trifluoromethylphenyl.

3. The compound of claim 1, wherein:
M$^D$ is Zr or Hf; and
R$^{11}$, R$^{11'}$, R$^{11''}$, R$^{12}$, and R$^{13}$ are independently H, Me, t-Bu, Ph, CH$_2$-Ph, 2,4,6-trimethylphenyl, 2,6-dimethylphenyl, 2,6-diisopropylphenyl, trifluoromethyl, pentafluorophenyl, or 4-trifluoromethylphenyl.

4. The compound of claim 3, wherein R$^{11'}$ and R$^{11''}$ are H.

5. The compound of claim 1, wherein the compound is:

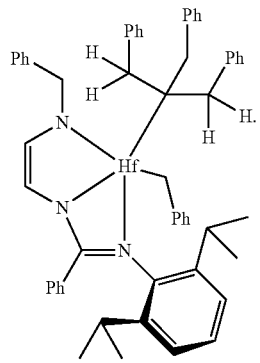

6. A catalyst composition comprising at least one activator and a compound having the formula:

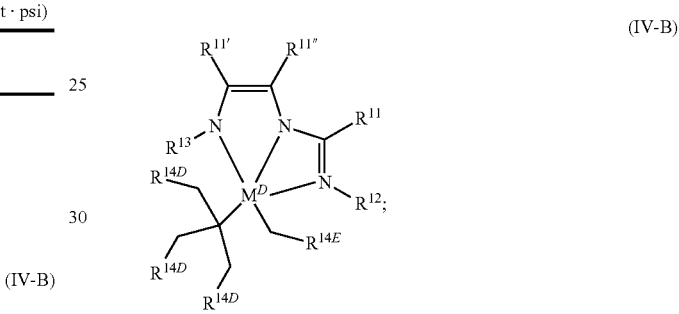

(IV-B)

or a partially saturated or saturated version thereof; wherein:
M$^D$ is Ti, Zr, or Hf;
R$^{11}$, R$^{11'}$, R$^{11''}$, R$^{12}$, and R$^{13}$ are independently H or a hydrocarbyl, hydrocarbyloxide, hydrocarbylamino, hydrocarbylsilyl, or halogenated hydrocarbyl group, any of which having up to 18 carbon atoms; and
R$^{14D}$ and R$^{14E}$ are phenyl groups.

7. The catalyst composition of claim 6, wherein the at least one activator comprises at least one aluminoxane compound, at least one organoboron or organoborate compound, at least one ionizing ionic compound, at least one activator-support, or any combination thereof.

8. The catalyst composition of claim 6, wherein the catalyst composition further comprises at least one organoaluminum compound.

9. The catalyst composition of claim 8, wherein the catalyst composition comprises at least one activator-support comprising a solid oxide treated with an electron-withdrawing anion.

10. The catalyst composition of claim 9, wherein the at least one activator-support comprises a fluorided solid oxide and/or a sulfated solid oxide.

11. The catalyst composition of claim 6, wherein:
R$^{11'}$ and R$^{11''}$ are H; and
R$^{11}$, R$^{12}$, and R$^{13}$ are independently H, Me, t-Bu, Ph, CH$_2$-Ph, 2,4,6-trimethylphenyl, 2,6-dimethylphenyl, 2,6-diisopropylphenyl, trifluoromethyl, pentafluorophenyl, or 4-trifluoromethylphenyl.

12. A method for preparing an article of manufacture comprising an olefin polymer, the method comprising:
(i) contacting the catalyst composition of claim 6 with an olefin monomer and optionally at least one olefin comonomer under polymerization conditions to produce the olefin polymer; and (ii) forming the article of manufacture comprising the olefin polymer.

13. An olefin polymerization process, the process comprising:

contacting a catalyst composition with an olefin monomer and optionally at least one olefin comonomer under polymerization conditions to produce an olefin polymer, wherein the catalyst composition comprises at least one activator and a compound having the formula:

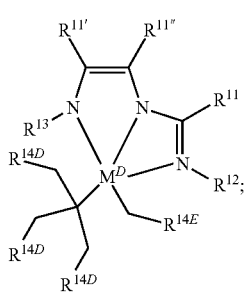

(IV-B)

or a partially saturated or saturated version thereof;
wherein:

$M^D$ is Ti, Zr, or Hf;

$R^{11}$, $R^{11'}$, $R^{11''}$, $R^{12}$, and $R^{13}$ are independently H or a hydrocarbyl, hydrocarbyloxide, hydrocarbylamino, hydrocarbylsilyl, or halogenated hydrocarbyl group, any of which having up to 18 carbon atoms; and $R^{14D'}$ and $R^{14E}$ are phenyl groups.

14. The process of claim 13, wherein the olefin monomer is ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, or styrene.

15. The process of claim 13, wherein the process is conducted in a slurry reactor, a solution reactor, a gas phase reaction, or combinations thereof.

16. The process of claim 13, wherein the at least one activator comprises at least one aluminoxane compound.

17. The process of claim 13, wherein the catalyst composition comprises at least one activator-support comprising a solid oxide treated with an electron-withdrawing anion.

18. The process of claim 17, wherein the at least one activator-support comprises a fluorided solid oxide and/or a sulfated solid oxide.

19. The process of claim 13, wherein the catalyst composition is contacted with ethylene and at least one olefin comonomer comprising 1-butene, 1-hexene, 1-octene, or a mixture thereof.

20. The process of claim 19, wherein:

$R^{11'}$ and $R^{11''}$ are H; and $R^{11}$, $R^{12}$, and $R^{13}$ are independently H, Me, t-Bu, Ph, $CH_2$-Ph, 2,4,6-trimethylphenyl, 2,6-dimethylphenyl, 2,6-diisopropylphenyl, trifluoromethyl, pentafluorophenyl, or 4-trifluoromethylphenyl.

* * * * *